United States Patent
Zhang et al.

(10) Patent No.: US 7,534,775 B2
(45) Date of Patent: May 19, 2009

(54) METHODS AND COMPOSITIONS FOR MODULATING CARDIAC CONTRACTILITY

(75) Inventors: H. Steve Zhang, Richmond, CA (US); Lei Zhang, Davis, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 482 days.

(21) Appl. No.: 11/101,095

(22) Filed: Apr. 7, 2005

(65) Prior Publication Data

US 2006/0079475 A1 Apr. 13, 2006

Related U.S. Application Data

(60) Provisional application No. 60/560,529, filed on Apr. 8, 2004, provisional application No. 60/574,039, filed on May 25, 2004.

(51) Int. Cl.
*A61K 48/00* (2006.01)
*C07H 21/02* (2006.01)
*C07H 21/04* (2006.01)

(52) U.S. Cl. ........................................ 514/44; 536/23.1

(58) Field of Classification Search ............... 435/320.1, 435/252.3; 536/23.1; 514/44
See application file for complete search history.

(56) References Cited

U.S. PATENT DOCUMENTS

| | | | |
|---|---|---|---|
| 4,186,183 A | 1/1980 | Steck et al. | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,603,044 A | 7/1986 | Geho et al. | |
| 4,774,085 A | 9/1988 | Fidler | |
| 4,797,368 A | 1/1989 | Carter et al. | |
| 4,837,028 A | 6/1989 | Allen | |
| 4,857,773 A | 8/1989 | Takata | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,173,414 A | 12/1992 | Lebkowski et al. | |
| 5,176,996 A | 1/1993 | Hogan et al. | |
| 5,210,015 A | 5/1993 | Gelfand et al. | |
| 5,328,470 A | 7/1994 | Nabel et al. | |
| 5,422,251 A | 6/1995 | Fresco | |
| 5,538,848 A | 7/1996 | Livak et al. | |
| 5,585,245 A | 12/1996 | Johnsson | |
| 5,674,722 A | 10/1997 | Mulligan et al. | |
| 5,693,622 A | 12/1997 | Wolff et al. | |
| 5,698,531 A | 12/1997 | Nabel et al. | |
| 5,707,969 A | 1/1998 | Nabel et al. | |
| 5,786,538 A | 7/1998 | Barone | |
| 5,789,538 A | 8/1998 | Rebar et al. | |
| 5,797,870 A | 8/1998 | March et al. | |
| 5,817,491 A | 10/1998 | Yee et al. | |
| 5,863,736 A | 1/1999 | Haaland | |
| 5,893,839 A | 4/1999 | Jounson | |
| 5,924,424 A | 7/1999 | Stevens et al. | |
| 5,925,012 A | 7/1999 | Murphy-Chutorian et al. | |
| 5,928,638 A | 7/1999 | Uchida et al. | |
| 5,931,810 A | 8/1999 | Grabek | |
| 5,941,868 A | 8/1999 | Kaplan et al. | |
| 5,944,754 A | 8/1999 | Vacanti | |
| 5,968,010 A | 10/1999 | Waxman et al. | |
| 5,972,013 A | 10/1999 | Schmidt | |
| 5,976,164 A | 11/1999 | Bencini et al. | |
| 5,993,443 A | 11/1999 | Murphy-Chutorian et al. | |
| 5,997,509 A | 12/1999 | Rosengart et al. | |
| 5,997,525 A | 12/1999 | March et al. | |
| 5,999,678 A | 12/1999 | Murphy-Chutorian et al. | |
| 6,001,350 A | 12/1999 | Mulligan et al. | |
| 6,007,408 A | 12/1999 | Sandhu | |
| 6,007,988 A | 12/1999 | Choo et al. | |
| 6,013,453 A | 1/2000 | Choo et al. | |
| 6,045,565 A | 4/2000 | Ellis et al. | |
| 6,048,332 A | 4/2000 | Duffy et al. | |
| 6,050,986 A | 4/2000 | Hektner | |
| 6,066,123 A | 5/2000 | Li et al. | |
| 6,067,988 A | 5/2000 | Mueller | |
| 6,086,582 A | 7/2000 | Altman et al. | |
| 6,140,081 A | 10/2000 | Barbas | |
| 6,140,466 A | 10/2000 | Barbas et al. | |
| 6,312,682 B1 | 11/2001 | Kingsman et al. | |
| 6,453,242 B1 | 9/2002 | Eisenberg et al. | |
| 6,534,261 B1 | 3/2003 | Cox et al. | |
| 6,607,882 B1 | 8/2003 | Cox et al. | |
| 6,669,936 B2 | 12/2003 | Kingsman et al. | |
| 6,746,838 B1 | 6/2004 | Choo et al. | |
| 6,866,977 B2 | 3/2005 | Sorriero et al. | |
| 2002/0160940 A1 | 10/2002 | Case et al. | |
| 2002/0173030 A1 | 11/2002 | Naldini et al. | |
| 2003/0021776 A1 | 1/2003 | Rebar et al. | |
| 2003/0050259 A1* | 3/2003 | Blatt et al. | ..................... 514/44 |
| 2003/0108880 A1 | 6/2003 | Rebar | |
| 2003/0119023 A1 | 6/2003 | Choo et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |

FOREIGN PATENT DOCUMENTS

WO    WO 91/16024 A1    10/1991

(Continued)

OTHER PUBLICATIONS

Verma and Somia (1997) Nature 239-242.*

(Continued)

*Primary Examiner*—Valarie Bertoglio
*Assistant Examiner*—Anoop Singh
(74) *Attorney, Agent, or Firm*—Robins & Pasternak LLP

(57) ABSTRACT

Methods and compositions are provided for modulating cardiac contractility by regulating transcription of the phsopholamban gene using engineered zinc finger proteins.

6 Claims, 7 Drawing Sheets

FOREIGN PATENT DOCUMENTS

| | | |
|---|---|---|
| WO | WO 91/17424 A1 | 11/1991 |
| WO | WO 93/24641 A2 | 9/1993 |
| WO | WO 94/05700 A2 | 3/1994 |
| WO | WO 95/19431 A1 | 7/1995 |
| WO | WO 96/06166 A1 | 2/1996 |
| WO | WO 98/44350 A1 | 10/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/29251 A1 | 6/1999 |
| WO | WO 99/31982 A1 | 7/1999 |
| WO | WO 99/33500 A2 | 7/1999 |
| WO | WO 99/38559 A1 | 8/1999 |
| WO | WO 99/49773 A2 | 10/1999 |
| WO | WO 99/49926 A2 | 10/1999 |
| WO | WO 99/59666 A1 | 11/1999 |
| WO | WO 00/04928 A1 | 2/2000 |
| WO | WO 00/15285 A1 | 3/2000 |
| WO | WO 00/23464 A2 | 4/2000 |
| WO | WO 00/24452 A1 | 5/2000 |
| WO | WO 00/25850 A1 | 5/2000 |
| WO | WO 00/27878 A1 | 5/2000 |
| WO | WO 00/41566 A1 | 7/2000 |
| WO | WO 00/42219 A1 | 7/2000 |
| WO | WO 01/16848 A2 | 3/2001 |
| WO | WO 01/18462 A1 | 3/2001 |
| WO | WO01/25417 * | 4/2001 |
| WO | WO 01/53480 A1 | 7/2001 |
| WO | WO 01/83732 A2 | 11/2001 |
| WO | WO 01/83793 A2 | 11/2001 |
| WO | WO02/057293 * | 7/2002 |
| WO | WO 02/057293 A2 | 7/2002 |
| WO | WO 02/077227 A2 | 10/2002 |
| WO | WO 03/087341 A2 | 10/2003 |

OTHER PUBLICATIONS

Pfeifer and Verma (2001) Annual Review of Genomics and Human Genetics.2: 177-211.*
Hajjar et al Proc. Natl. Acad. Sci., USA, 95, 5251-5256, 1998.*
Miyamoto et al Proc Natl Acad Sci U S A. 2000; 97(2): 793-798.*
Tada et al Annals of the New York Academy of Sciences 853:116-129, 1998.*
Yaghmai et al Molecular Therapy, 2002, 5(6) 685694.*
GenBank accession No. AF177763 dated.*
Jamison et al Nat Rev Drug Dicover, 203, 2(5), 361-368.*
del Monte et al Circulation. 2002; 105(8): 904-7.*
Ahmad, et al., "Antibody-Mediated Specific Binding and Cytotoxicity of Liposome-Entrapped Doxorubicin to Lung Cancer Cells in Vitro," *Cancer Res.* 52:4817-4820 (1992).
Altschul, et al., "Basic Local Alignment Search Tool," *J. Mol. Biol.* 215:403-410 (1990).
Alvarez, et al., "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Human Gene Therapy* 8(5):597-613 (1997).
Anderson, "Human Gene Therapy," *Science* 256:808-813 (1992).
Arora, et al., "Residues 1-254 of Anthrax Toxin Lethal Factor are Sufficient to Cause Cellular Uptake of Fused Polypeptides," *J. Biol. Chem.* 268:3334-3341 (1993).
Ausubel, et al., "Current Protocols in Molecular Biology," John Wiley & Sons, New York, (1987), *Table of Contents only*.
Beaucage & Caruthers, "Deoxynucleoside Phosphoramidites: A New Class of Key Intermediates for Deoxypolynucleotide Synthesis," *Tetrahedron Lett.* 22:1859-1862 (1981).
Behr, et al., "Gene Transfer With Synthetic Cationic Amphiphiles: Prospects for Gene Therapy," *Bioconjugate Chem.* 5:382-389 (1994).

Berg, et al., "The Galvanization of Biology: A Growing Appreciation for the Roles of Zinc," *Science* 271:1081-1085 (1996).
Bird, et al., "Methylation-Induced Repression—Belts, Braces, and Chromatin," *Cell* 99:451-454 (1990).
Bitko and Barik, "Persistent Activation of Rela by Respiratory Syncytial Virus Involves Protein Kinase C, Underphosphorylated Ikappa Bbeta, and Sequestration of Protein Phosphatase 2A by the Viral Phosphoprotein," *J. Virol.* 72:5610-5618 (1998).
Blaese, et al., "Vectors in Cancer Therapy: How Will They Deliver?" *Cancer Gene Therapy* 2(4): 291-297 (1995).
Braz, et al., "PKC-A Regulates Cardiac Contractility and Prepensity Toward Heart Failure," *Nature Med* 10(3):248-254 (2004).
Buchsacher, et al., "Human Immunodeficiency Virus Vectors for Inducible Expression of Foreign Genes," *J. Virol.* 66:2731-2739 (1992).
Buratowski and Chodosh, "Short Protocols in Molecular Biology" Ausubel ed., pp. 12.2.1-12.2.7 (1996).
Burton, et al., "Multiple Applications for Replication-Defective Herpes Simplex Virus Vectors," *Stem Cells* 19:358-377 (2001).
Carbonetti, et al., "Use of Pertussis Toxin Vaccine Molecule PT9K/129G to Deliver Peptide Epitopes for Simulation of a Cytotoxic T Lymphocyte Response," *Abstr. Annu. Meet. Am. Soc. Microbiol.* 95:295 (1995).
Chern, et al., "The Regulator of MAT2 (ROM2) Protein Binds to Early Maturation Promoters and Represses PVALF-Activated Transcription," *Plant Cell* 8:305-321(1996).
Cho, et al., "Analysis of the C-Terminal Region of *Arabidopsis thaliana* APETALA1 as a Transcription Activation Domain," *Plant Mol. Biol.* 40:419-429 (1999).
Choo, et al., "Toward a Code for the Interactions of Zinc Fingers With DNA: Selection of Randomized Fingers Displayed on Phage," *PNAS* 91:11163-11167 (1994).
Choo, et al., "Selection of DNA Binding Sites for Zinc Fingers Using Randomized DNAs Reveals Coded Interactions," *PNAS* 91:11168-11172 (1994).
Chossat, et al., "Adenoviral SERC1a Gene Transfer to Adult Rat Ventricular Myocytes Induces Physiological Changes in Calcium Handling," *Cardiovasc Res* 49(2):288-297 (2001).
Cirillo, et al., "Binding of the Winged-Helix Transcription Factor HNF3 to a Linker Histone Site on the Nucleosome," *EMBO J.* 17:244-254 (1998).
Colley, et al., "Conversion of a Golgi Apparatus Sialyltransferase to a Secretory Protein by Replacement of the NH2-Terminal Signal Anchor With a Signal Peptide," *J. Biol. Chem.* 264:17619-17622 (1989).
Cordingley, et al., "Steroid-Dependent Interaction of Transcription Factors With the Inducible Promoter of Mouse Mammary Tumor Virus in Vivo," *Cell* 48:261-270 (1987).
Crystal, "Transfer of Genes to Humans: Early Lessons and Obstacles to Success," *Science* 270:404-410 (1995).
Damm, et al., "Protein Encoded by V-Erba Functions as a Thyroid-Hormone Receptor Antagonist," *Nature* 339:593-597 (1989).
Deamer & Bangham, "Large Volume Liposomes by an Ether Vaporization Method," *Biochim. Biophys. Acta* 443:629-634 (1976).
Delenda, "Lentiviral Vectors: Optimization of Packaging, Transduction and Gene Expression," *J. Gene Med* 6:S125-S138 (2004).
del Monte, et al., "Targeting Phospholamban by Gene Transfer in Human Heart Failure," *Circulation* 105(8):904-907 (2002).
Desjarlais, et al., "Use of a Zinc-Finger Consensus Sequences Framework and Specificity Rules to Design Specific DNA Binding, Proteins" *PNAS* 90:2256-2260 (1993).
Desjarlais, et al., "Toward Rules Relating Zinc Finger Protein Sequences and DNA Binding Site Preferences," *PNAS* 89:7345-7349 (1992).
Desjarlais, et al., "Length-Encoded Multiplex Binding Site Determination: Application to Zinc Finger Proteins," *PNAS* 91:11099-11103 (1994).
Dillon, "Regulating Gene Expression in Gene Therapy," *Trends in Biotechnology* 11:167-175 (1993).
Donnelly, et al., "Targeted Delivery of Peptide Epitopes to Class I Major Histocompatibility Molecules by a Modified Pseudomonas Exotoxin," *PNAS* 90:3530-3534 (1993).

Doyle & Hunt, "Reduced Nuclear Factor Kappa B Expression in Rat Primary Sensory Neurons After Peripheral Nerve Injury," *Neuro Report* 8:2937-2942 (1997).

Dranoff, et al., "Phase I Study of Vaccination With Autologous, Irradiated Melanoma Cells Engineered to Secrete Human Granulocyte-Macrophage Colony Stimulating Factor," *Hum. Gene. Ther.* 1:111-123 (1997).

Dull, et al., "A Third-Generation Lentivirus Vector With a Conditional Packaging System," *J. Virol.* 72:8463-8471 (1998).

Dunbar, et al., "Retrovirally Marked CD34-Enriched Peripheral Blood and Bone Marrow Cells Contribute to Long-Term Engraftment After Autologous Transplantation," *Blood* 85:3048-3357 (1995).

Eisenberg & Mcknight, "Promoter Domains Required for Expression of Plasmid-Borne Copies of the Herpes Simplex Virus Thymidine Kinase Gene in Virus-Infected Mouse Fibroblasts and Microinfected Frog Oocytes," *Mol. Cell. Biol.* 5:1940-1947 (1985).

Eizema, et al., "Adenovirus-Based Phospholamban Antisense Expression as a Novel Approach to Improve Cardiac Contractile Dysfunction," *Circulation* 101(18):2193-2199 (2000).

Ellem, et al., "A Case Report: Immune Responses and Clinical Course of the First Human Use of Granulocyte Macrophage-Colony-Stimulating-Factor-Transduced Autologous Melanoma Cells for Immunotherapy" *Cancer Immunol. Immunother.* 44(1):10-20 (1997).

Fahraeus, et al., "Inhibition of PRB Phosphorylation and Cell-Cycle Progression by a 20-Residue Peptide Derived From $P16^{CDKN2/INK4A}$," *Current Biology* 6:84-91 (1996).

Fields, et al., "A Novel Genetic System to Detect Protein—Protein Interactions," *Nature* 340:245-246 (1989).

Follenzi, et al., "Gene Transfer by Lentiviral Vectors is Limited by Nuclear Translocation and Rescued by HIV-1 POL Sequences," *Nature Genetics* 25:217-222 (2000).

Fraley, et al., "Entrapment of a Bacterial Plasmid in Phospholipid Vesicles: Potential for Gene Transfer," *PNAS USA* 76:3348-3352 (1979).

Fuji, et al., "Co-Expression of Slow-Twitch/Cardiac Muscle $Ca^2$—ATPase (SERCA2) and Phospholamban," *FEBS Let* 273(1-2):232-234 (1990).

Gao, et al., "Cationic Liposome-Mediated Gene Transfer," *Gene Therapy* 2:710-722 (1995).

GenBank accession No. AF177763.
GenBank accession No. AH002227.
GenBank accession No. AH003051.
GenBank accession No. AH001235.
GenBank accession No. NM_023129.
GenBank accession No. NT_033944.
GenBank accession No. NW_043442.
GenBank accession No. AF037348.

Gibson, et al., "A Novel Method for Real Time Quantitative RT-PCR," *Genome Research* 6:995-1001 (1996).

Goff, et al., "Identification of Functional Domains in the Maize Transcriptional Activator C1: Comparison of Wild-Type and Dominant Inhibitor Proteins," *Genes Dev.* 5:298-309 (1991).

Gong, et al., "A Constitutively Expressed MYC-Like Gene Involved in Anthocyanin Biosynthesis From Perilla Frutescens: Molecular Characterization, Heterologous Expression in Transgenic Plants and Transactivation in Yeast Cells," *Plant Mol. Biol.* 41:33-44 (1999).

Gossen, et al., "Tight Control of Gene Expression in Mammalian Cells by Tetracycline-Responsive Promoter," *PNAS* 89:5547-5551 (1992).

Greisman, et al., "A General Strategy for Selecting High-Affinity Zinc Finger Proteins for Diverse DNA Target Sites," *Science* 275:657-661 (1997).

Haas, et al., "Critical Factors Influencing Stable Transduction of Human CD34(+) Cells With HIV-1-Derived Lentiviral Vectors," *Mol. Therapy* 2:71-80 (2000).

Hagmann, et al., "The VP16 Paradox: Herpes Simplex Virus VP16 Contains a Long-Range Activation Domain but Within the Natural Multiprotein Complex Activates Only From Promoter-Proximal Positions," *J. Virol.* 72:5952-5962 (1997).

Han, et al., "Ligand-Directed Retroviral Targeting of Human Breast Cancer Cells," *PNAS USA* 92:9747-9751 (1995).

Heid, et al., "Real Time Quantitative PCR," *Genome Research* 6:986-994 (1996).

Henikoff & Henikoff, "Amino Acid Substitution Matrices From Protein Blocks," *Proc. Natl. Acad. Sci. USA* 89:10915-10919 (1992).

Hermonat & Musiczka, "Use of Adeno-Associated Virus as a Mammalian DNA Cloning Vector: Transduction of Neomycin Resistance Into Mammalian Tissue Culture Cells," *PNAS USA* 81:6466-6470 (1984).

Hobo, et al., "A BZIP Factor, TRAB1, Interacts With VP1 and Mediates ABSCISIC Acid-Induced Transcription," *Proc. Natl. Acad. Sci. USA* 96:15,348-15,353 (1999).

Holland, et al., "Detection of Specific Polymerase Chain Reaction Product by Utilizing the 5' {RightArrow} 3' Exonuclease Activity of Thermus Aquaticus DNA Polymerase," *Proc. Natl. Acad. Sci. USA* 88:7276-7280 (1991.

Hope, et al., "Production of Large Unilamellar Vesicles by a Rapid Extrusion Procedure. Characterization of Size Distribution, Trapped Volume and Ability to Maintain a Membrane Potential," *Biochim. Biophys. Acta.* 812:55-65 (1985).

Hope, et al., "Generation of Multilamellar and Unilamellar Phospholipid Vesicles," *Chem. Phys. Lipids* 40:89-108 (1986).

Humeau, et al., "Efficient Lentiviral Vector-Mediated Control of HIV-1 Replication in CD4 Lymphocytes From Diverse HIV+ Infected Patients Grouped According to CD4 Count and Viral Load," *Mol. Therapy* 9:902-913 (2004).

Inaba, et al., "Generation of Large Numbers of Dendritic Cells From Mouse Bone Marrow Cultures Supplemented With Granulocyte/Macrophage Colony-Stimulating Factor," *J. Exp. Med.* 176:1693-1702 (1992).

Jamieson, et al., "In Vitro Selection of Zinc Fingers With Altered DNA-Binding Specificity," *Biochemistry* 33:5689-5695 (1994).

Jamieson, et al., "Drug Discovery With Engineered Zinc-Finger Proteins," *Nature Reviews Drug Discovery* 2(5):361-368 (2003).

Johann, et al., "GLVR1, A Receptor for Gibbon Ape Leukemia Virus, is Homologous to a Phosphate Permease of Neurospora Crassa and is Expressed at High Levels in the Brain and Thymus," *J. Virol.* 66:1635-1640 (1992).

Karlin & Altschul, "Applications and Statistics for Multiple High-Scoring Segments in Molecular Sequences," *Proc. Natl. Acad. Sci. USA* 90:5873-5787 (1993).

Kearns, et al., "Recombinant Adeno-Associated Virus (AAV-CFTR) Vectors do not Integrate in a Site-Specific Fashion in an Immortalized Epithelial Cell Line," *Gene Ther.* 9:748-755 (1996).

Kim, et al., "Getting a Handhold on DNA: Design of Poly-Zinc Finger Proteins With Femtomolar Dissociation Constents," *Proc. Natl. Acad. Sci. USA* 93:1156-1160 (1996).

Kim, et al., "Getting a Handhold on DNA: Design of Poly-Zinc Finger Proteins With Femtomolar Dissociation Constants," *PNAS USA* 95:2812-2817 (1998).

Klimpel, et al., "Anthrax Toxin Protective Antigen is Activated by a Cell Surface Protease With the Sequence Specificity and Catalytic Properties of Furin," *PNAS USA* 89:10277-10281 (1992).

Knoepfler, et al., "Sin Meets Nurd and Other Tails of Repression," *Cell* 99: 447-450 (1999).

Kochanek, et al., "A New Adenoviral Vector: Replacement of All Viral Coding Sequences With 28 KB of DNA Independently Expressing Both Full-Length Dystrophin and B-Galactosidase," *Proc. Natl. Acad. Sci. USA* 93:5731-5736 (1996).

Kohn, et al., "Engraftment of Gene-Modified Umbilical Cord Blood Cells in Neonates With Adenosine Deaminase Deficiency," *Nat. Med.* 1:1017-1023 (1995).

Koss, et al., "The Relative Phospholamban and SERCA2 Ratio: A Critical Determinant of Myocardial Contractility," *Basic Res. Cardiol.* 92(1):17-24 (1997).

Kotin, "Prospects for the Use of Adeno—Associated Virus as a Vector for Human Gene Therapy," *Human Gene Therapy* 5:793-801 (1994).

Kremer & Perricaudet, "Adenovirus and Adeno-Associated Virus Mediated Gene Transfer," *Br Med Bull* 51(1):31-44 (1995).

Krisky, et al., "Development of Herpes Simplex Virus Replication Defective Multigene Vectors for Combination Gene Therapy Applications," *Gene Therapy* 5(11):1517-1530 (1998).

Krisky, et al., "Deletion of Multiple Immediate Early Genes From Herpes Simplex Virus Reduces Cytotoxicity and Permits Long-Term Gene Expression in Neurons," *Gene Therapy* 5(12):1593-1603 (1998).

Lemon, et al., "Nuclear Receptor Cofactors as Chromatin Remodelers," *Curr Opin Genet Dev.* 9(5):499-504 (1999).

Leo, et al., "The SRC Family of Nuclear Receptor Coactivators," *Gene* 245:1-11 (2000).

Leonetti, et al., "Antibody-Targeted Lipsomes Containing Oligodeoxyribonucleotides Complementary to Viral RNA Selectively Inhibit Viral Replication," *PNAS USA* 87:2448-2451 (1990).

Lilley, et al., "Multiple Immediate-Early Gene-Deficient Herpes Simplex Virus Vectors Allowing Efficient Gene Delivery to Neurons in Culture and Widespread Gene Delivery to the Central Nervous System in Vivo," *J. Virology* 75:4343-4356 (2001).

Lin, et al.; "Inhibition of Nuclear Translocation of Transcription Factor NF-B by a Synthetic Peptide Containing a Cell Membrane-Permeable Motif and Nuclear Localization Sequence," *J. Biol. Chem.* 270:14255-14258 (1995).

Liu, et al., "Suppression of Growth and Transformation and Induction of Apoptosis by EGR-1," *Cancer Gene Ther.* 5:3-28 (1998).

Liu et al., "Design of Polydactyl Zinc-Finger Proteins for Unique Addressing Within Complex Genomes," *PNAS USA* 94:5525-5530 (1997).

Livak, et al., "Oligonucleotides With Fluorescent Dyes at Opposite Ends Provide a Quenched Probe System Useful for Detecting PCR Product and Nucleic Acid Hybridization," *PCR Methods and Applications* 4(6):357-362 (1995).

Maclennan, et al. "Phospholamban: A Crucial Regulator of Cardiac Contractility," *Nat Rev Mol Cell Biol.* 4(7):566-577 (2003).

Malech, et al., "Prolonged Production of NADPH Oxidase-Corrected Granulocytes After Gene Therapy of Chronic Granulomatous Disease," *PNAS USA* 94:12133-12138 (1997).

Malik, et al., "Transcriptional Regulation Through Mediator-Like Coactivators in Yeast and Metazoan Cells," *Trends Biochem. Sci.* 25:277-283 (2000).

Manteuffel-Cymborowska, "Nuclear Receptors, Their Coactivators and Modulation of Transcription," *Acta Biochim. Pol.* 46:77-89 (1999).

Mapp, et al., "Activation of Gene Expression by Small Molecule Transcription Factors," *PNAS USA* 97:3930-3935 (2000).

Margolin, et al., "Kruppel-Associated Boxes Are Potent Transcriptional Repression Domains," *PNAS USA* 91:4509-4513 (1994).

Mayer, et al., "Vesicles of Variable Sizes Produced by a Rapid Extrusion Procedure," *Biochim. Biophys. Acta* 858:161-168 (1986).

McKenna, et al., "Nuclear Receptor Coactivators: Multiple Enzymes, Multiple Complexex, Multiple Functions," *J. Steroid Biochem. Mol. Biol.* 69:3-12 (1999).

Miller, "Human Gene Therapy Comes of Age," *Nature* 357:455-460 (1992).

Miller, et al., "Construction and Properties of Retrovirus Packaging Cells Based on Gibbon Ape Leukemia Virus," *J. Virol.* 65:2220-2224 (1991).

Minamisawa, et al., "Chronic Phospholamban-Sarcoplasmic Reticulem Calcium ATPase Interaction is the Critical Calcium Cycling Defect in Dilated Cardiomyopathy," *Cell* 99(3):313-322 (1999).

Mistili & Spector, "Applications of the Green Flourescent Protein in Cell Biology and Biotechnology," *Nature Biotechnology* 15:961-964 (1997).

Mitani & Caskey, "Delivering Therapeutic Genes: Matching Approach and Application," *Trends Biotechnol.* 11:162-166 (1993).

Miyoshi, et al., "Development of a Self-Inactivating Lentivirus Vector," *J. Virology* 72:8150-8157 (1998).

Muzyczka, "Adeno-Associated Virus (AAV) Vectors: Will They Work?" *J. Clin. Invest.* 94:1351 (1994).

Nabel & Felgner, "Direct Gene Transfer for Immunotherapy and Immunization," *Trends Biotechnol* 11:211-215 (1993).

Nakayama, et al., "Cardiac-Specific Overexpression of a High $CA^{2+}$ Affinity Mutant of SERCA2a Attenuates in Vivo Pressure Overload Cardiac Hypertrophy," *FASEB J* 17(1):61-63 (2002).

Naldini, et al., "Efficient Transfer, Integration, and Sustained Long-Term Expression of the Transgene in Adult Rat Brains Injected With a Lentiviral Vector," *Proc. Natl. Acad. Sci. USA* 93:11382-11388 (1996).

Needleman & Wunsch, "A General Method Applicable to the Search for Similarities in the Amino Acid Sequences of Two Proteins," *J. Mol. Biol.* 48:443-453 (1970).

Neering, et al., "Transduction of Primitive Human Hematopoietic Cells With Recombinant Adenovirus Vectors," *Blood* 88:1147-1155 (1996).

Novak, et al., "Functional Characterization of Protease-Treated *Bacillus anthracis* Protective Antigen," *J. Biol. Chem.* 267:17186-17193 (1992).

Ogawa, et al., "Rice Gibberellin-Insensitive Gene Homolog, OSGA1, Encodes a Nuclear-Localized Protein Capable of Gene Activation at Transcriptional Level," *Gene* 245:21-29 (2000).

Okanami, et al., Half-1 a BZIP-Type Protein, Interacting With the Wheat Transcription Factor HBP-1A Contains a Novel Transcriptional Activation Domain, *Genes Cells* 1:87-99 (1996).

Oligino, et al., "Drug Inducible Transgene Expression in Brain Using a Herpes Simplex Virus Vector," *Gene Ther.* 5:491-496 (1998).

Pain, et al., "The Carbonic Anhydrase II Gene, A Gene Regulated by Thyroid Hormone and Erythropoietin, is Repressed by V-ERBA Oncogene in Erythrocytic Cells," *New Biol.* 2:284-294 (1990).

Palva, et al., "Secretion of Interferon by *Bacillus subtilis*," *Gene* 22:229-235 (1983).

Pearson & Lipman, "Improved Tools for Biological Sequence Comparison," *PNAS USA* 85:2444-2448 (1988).

Pengue et al., "Repression of Transcriptional Activity at a Distance by the Evolutionarily Conserved Krab Domain Present in a Subfamily of Zinc Finger Proteins," *Nuc. Acids Res.* 22(15):2908-2914 (1994).

Perelle, et al., "Characterization of Clostridium Perfringens Iota-Toxin Genes and Expression in *Escherichia coli*," *Infect. Immun.* 61:5147-5156 (1993).

Pina, et al., "Nucleosome Positioning Modulates Accessibility of Regulatory Proteins to the Mouse Mammary Tumor Virus Promoter," *Cell* 60:719-731 (1990).

Pomerantz, et al., "Structure-Based Design of Transcription Factors," *Science* 267: 93-96 (1995).

Pomerantz et al., "Analysis of Homeodomain Function by Structure-Based Design of a Transcription Factor," *PNAS USA* 92: 9752-9756 (1995).

Poon, et al., "Human Immunodeficiency Virus Type 1 (HIV-1) VPR Enhances Expression From Unintegrated HIV-1 DNA," *J. Virology* 77:3962-3972 (2003).

Prochiantz, "Getting Hydrophilic Compounds Into Cells; Lessons From Homeopeptides," *Current Opinion in Neurobiology* 6:629-634 (1996).

Rebar, et al, "Zinc Finger Phage: Affinity Selection of Fingers With New DNA-Binding Specifities," *Science* 263: 671-673 (1994).

Remy, et al., "Gene Transfer With a Series of Lipophilic DNA-Binding Molecules," *Bioconjugate Chem.* 5:647-654 (1994).

Rendahl, et al., "Regulation of Gene Expression in Vivo Following Transduction by Two Separate RAAV Vectors," *Nat. Biotechnol.* 16:757-761 (1998).

Renneisen, et al., "Inhibition of Expression of Human Immunodeficiency Virus-1 in Vitro by Antibody-Targeted Liposomes Containing Antisense RNA to the ENV Region," *J. Biol. Chem.*, 265:16337-16342 (1990).

Rhodes et al., "Zinc Fingers: They Play a Key Part in Regulating the Activity of Genes in Many Species, From Yeast to Humans. Fewer Than 10 Years Ago no on Knew They Existed." *Scientific American* 268:56-65 (1993).

Robertson, et al., "DNMT1 Forms a Complex With RB, E2F1 and HDAC1 and Represses Transcription From E2F-Responsive Promoters," *Nature Genet.* 25:338-342 (2000).

Robyr, et al., "Nuclear Hormone Receptor Coregulators in Action: Diversity for Shared Tasks," *Mol. Endocrinol.* 14:329-347 (2000).

Rosenecker, et al., "Adenovirus Infection in Cystic Fibrosis Patients: Implications for the Use of Adenoviral Vectors for Gene Transfer," *Infection* 24(1):5-8 (1996).

Samulski, et al., "Helper-Free Stocks of Recombinant Adeno-Associated Viruses: Normal Integration Does Not Require Viral Gene Expression," *J. Virol.* 63:3822-3828 (1989).
Santana, et al., "Amount of Calcium in the Sorcoplasmic Reticulum: Influence on Excitation-Contraction Coupling in Heart Muscle," *Heart Vessels*, Suppl 12:44-49 (1997).
Sap, et al., "Repression of Transcription Mediated at a Thyroid Hormone Response Element by the V-ERB-A Oncogene Product," *Nature* 340:242-244 (1989).
Seipal, et al., "Different Activation Domains Stimulates Transcription From Remote ('Enhancer') and Proximal ('Promoter') Positions," *EMBO J.* 11:4961-4968 (1992).
Smith & Waterman, "Comparison of Biosequences," *Adv. Appl. Math.* 2:482-489 (1981).
Sommerfelt, et al., "Receptor Interference Groups of 20 Retroviruses Plating on Human Cells," *Virol.* 176:58-69 (1990).
Sprenger-Haussels, et al., "Transactivation Properties of Parsley Proline-Rich BZIP Transcription Factors," *Plant J.* 22:1-8 (2000).
Stenmark, et al., "Peptides Fused to the Amino-Terminal End of Diphtheria Toxin Are Translocated to the Cytosol," *J. Cell. Biol.* 113:1025-1032 (1991).
Sterman, et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," *Hum. Gene Ther.* 7:1083-1092 (1998).
Szoka, et al., "Comparative Properties and Methods of Preparation of Lipid Vesicles (Liposomes)," *Ann. Rev. Biophys. Bioeng.* 9:467-508 (1980).
Thiesen, et al., "Multiple Genes Encoding Zinc Finger Domains Are Expressed in Human T Cells," *New Biologist* 2(4):363-374 (1990).
Topf, et al., "Regional 'Pro-Drug' Gene Therapy: Intravenous Administration of an Adenoviral Vector Expressing the *E. coli* cytosine Deaminase Gene and Systemic Administration of 5-Fluorocytosine Suppresses Growth of Hepatic Metastasis of Colon Carcinoma," *Gene Ther.* 5:507-513 (1998).
Torchia, et al., "Co-Activators and Co-Repressors in the Integration of Transcriptional Responses," *Curr. Opin. Cell. Biol.* 10:373-383 (1998).
Tratschin, et al., "Adeno-Associated Virus Vector for High-Frequency Integration, Expression, and Rescue of Genes in Mammalian Cells," *Mol. Cell. Biol.* 5:3251-3260 (1985).
Tratschin, et al., "A Human Parvovirus, Adeno-Associated Virus, as a Eucaryotic Vector: Transient Expression and Encapsidation of the Procaryotic Gene for Chloramphenicol Acetyltransferase," *Mol. Cell. Biol.* 4:2072-2081 (1984).
Tyler, et al., "The 'Dark Side' of Chromatin Remodeling: Repressive Effects on Transcription," *Cell* 99:443-446 (1999).
Ulmasov, et al., "Activation and Repression of Transcription by Auxin-Response Factors," *Proc. Natl. Acad. Sci. USA* 96:5844-5849 (1999).
Utley, et al., "Transcriptional Activators Direct Histone Acetyltransferase Complexes to Nucleosomes," *Nature* 394:498-502 (1998).
Van Brunt, "Molecular Farming: Transgenetic Animals as Bioreactors," *Biotechnology* 6(10):1149-1154 (1988).
Van Devanter, et al., "Characterization of an Adduct Between CC-1065 and a Defined Oligonucleotide Duplex," *Nucleic Acids Res.* 12:6159-6168 (1984).
Vigne, "Third-Generation Adenovectors for Gene Therapy," *Restorative Neurology and Neuroscience* 8:35-36 (1995).

Wagner, et al., "Efficient and Persistent Gene Transfer of AAV-CFTR in Maxillary Sinus," *Lancet* 351:1702-1703 (1998).
Wallace, et al., "A Set of Synthetic Oligodeoxyribonucleotide Primers for DNA Sequencing in the Plasmid Vector PBR322," *Gene* 16:21-26 (1981).
Wang, et al., "Postive and Negative Regulation of Gene Expression in Eukaryotic Cells With an Inducible Transcritional Regulator," *Gene Ther.* 4:432-441 (1997).
Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).
West, et al., "Gene Expression in Adeno-Associated Virus Vectors: The Effects of Chimeric MRNA Structure, Helper Virus, and Adenovirus VA1 RNA," *Virology* 160:38-47 (1987).
Williams, et al., "Low Density Lipoprotein Receptor-Independent Hepatic Uptake of a Synthetic, Cholesterol-Scavenging Lipoprotein: Implications for the Treatment of Receptor-Deficient Atherosclerosis," *PNAS USA* 85:242-246 (1988).
Wilson, et al., "Formation of Infectious Hybrid Virions With Gibbon Ape Leukemia Virus and Human T-Cell Leukemia Virus Retroviral Envelope Glycoproteins and the GAG and POL Proteins of Moloney Murine Leukemia Virus," *J. Virol.* 63:2374-2378 (1989).
Witzgall et al., "The Kruppel-Associated Box-A (KRAB-A) Domain of Zinc Finger Proteins Mediates Transcriptional Repression," *PNAS USA* 91:4514-4518 (1994).
Wu, et al., "Functional Analysis of HD2 Histone Deacetylase Homologues in *Arabidopsis thaliana*," *Plant J.* 22:19-27 (2000).
Wu, et al., "Building Zinc Fingers by Selection: Toward a Therapeutic Application," *PNAS USA* 92:344-348 (1995).
Yeh, et al., "Peptide-Mediated Delivery of an Artificial Transcription Factor to Upregulate Specific Endogenous Gene Expression: A Novel Approach to Gene Therapy," *Molecular Therapy* 7(5):S461, Abstract #1191.
Yu, et al., "Progress Towards Gene Therapy for HIV Infection," *Gene Therapy*, 1:13-26 (1994).
Zenke, et al., "V-ERBA Specifically Suppresses Transcription of the Avian Erythrocute Anion Transporter (Band 3) Gene," *Cell* 52:107-119 (1988).
Zenke, et al., "V-ERBA Oncogene Activation Entails the Loss of Hormone-Dependant Regulator Activity of C-ERBA," *Cell* 61:1035-1049 (1990)).
Zhang et al., "Enhanced Cardiac Muscle Contractility Achieved by Engineered Zinc Finger Transcriptional Repressors of Phospholamban," *Molecular Therapy* 9:S356 (2004).
Zhao, et al., "Combined Phospholamban Ablation and SERCA1a Overexpression Result in a New Hyperdynamic Cardiac State," *Cardiovasc. Res.* 57(1):71-81 (2003).
Zufferey, et al., "Self-Inactivating Lentivirus Vector for Safe and Efficient in Vivo Gene Delivery," *J. Virol.* 72:9873-9880 (1998).
Rebar et al., "Induction of angiogenesis in a mouse model using engineered transcription factors," Nat. Med. 8(12):1427-1432 (2002).
Watanabe, et al., "Phospholamban Ablation by RNA Interference Increases $CA^{2+}$ Uptake Into Rat Cardiac Myocyte Sarcoplasmic Reticulium," Journal of Molecular and Cellular Cardiology 37:691-698 (2004).
US 6,056,969, 05/2000, Crittenden (withdrawn)

* cited by examiner

FIG. 1

A. Fusion Protein Comprising SBS-6439 (SEQ ID NO:68)

MAPKKKRKVGIHGVPAAMAERPYACPVESCDRRFSTSADLTEHIRIHTGQKPFQCRICM
RNFSASANLSRHIRTHTGGERPFQCRICMRNFSRSDALSTHIRTHTGEKPFACDICGRK
FADRSTRTKHTKIHTGSQKPFQCRICMRNFSRSDVLSAHIRTHTGEKPFACDICGKKFA
DRSNRIKHTKIHLRQKDAARGSGMDAKSLTAWSRTLVTFKDVFVDFTREEWKLLDTAQQ
IVYRNVMLENYKNLVSLGYQLTKPDVILRLEKGEEPWLVEREIHQETHPDSETAFEIKS
SVDYKDDDDK

B. Fusion Protein Comprising SBS-6576 (SEQ ID NO:69)

MAPKKKRKVGIHGVPAAMAERPFQCRICMRNFSRSDHLSQHIRTHTGEKPFACDICGKK
FARSDVRKNHTKIHTGGGGSQRPFQCRICMRNFSRSDALSVHIRTHTGEKPFACDICGR
KFADNANRTKHTKIHTGSQKPFQCRICMRNFSRSDHLSTHIRTHTGEKPFACDICGRKF
ATSSNRTKHTKIHLRQKDAARGSGMDAKSLTAWSRTLVTFKDVFVDFTREEWKLLDTAQ
QIVYRNVMLENYKNLVSLGYQLTKPDVILRLEKGEEPWLVEREIHQETHPDSETAFEIK
SSVDYKDDDDK

FIG. 3
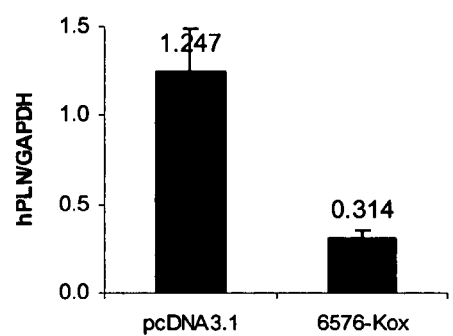
A UtSMC cells
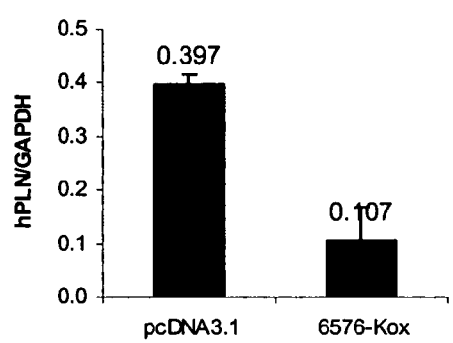
B JRH30 cells
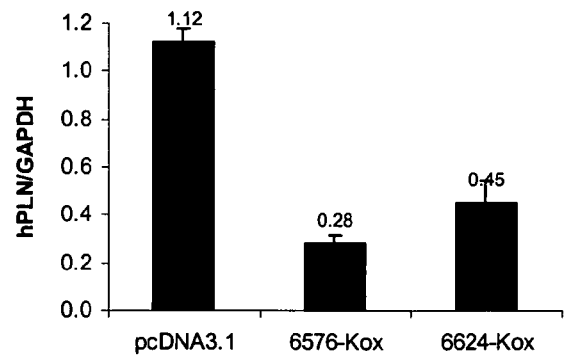
C UtSMC cells
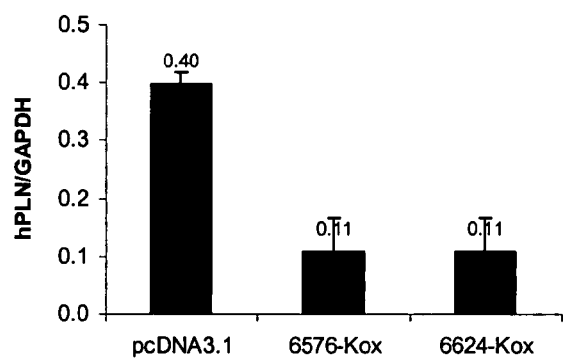
D SJRH30 cells

SEQUENCE LISTING

```
<160> NUMBER OF SEQ ID NOS: 104

<210> SEQ ID NO 1
<211> LENGTH: 25
<212> TYPE: PRT
<213> ORGANISM: Artificial
<220> FEATURE:
<223> OTHER INFORMATION: ZFP motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
```

```
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (23)..(24)
<223> OTHER INFORMATION: Xaa may be any amino acid, Xaa may be present
      or absent

<400> SEQUENCE: 1

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 2
<211> LENGTH: 9
<212> TYPE: DNA
<213> ORGANISM: Artificial
<220> FEATURE:
<223> OTHER INFORMATION: target DNA

<400> SEQUENCE: 2 ggcgtagac                                                              9

<210> SEQ ID NO 3
<211> LENGTH: 9
<212> TYPE: DNA
<213> ORGANISM: Artificial
<220> FEATURE:
<223> OTHER INFORMATION: target DNA

<400> SEQUENCE: 3 ggcgacgta                                                              9

<210> SEQ ID NO 4
<211> LENGTH: 5
<212> TYPE: PRT
<213> ORGANISM: Artificial
<220> FEATURE:
<223> OTHER INFORMATION: peptide linker

<400> SEQUENCE: 4

Thr Gly Glu Lys Pro
1               5

<210> SEQ ID NO 5
<211> LENGTH: 5
<212> TYPE: PRT
<213> ORGANISM: Artificial
<220> FEATURE:
<223> OTHER INFORMATION: peptide linker

<400> SEQUENCE: 5

Gly Gly Gly Gly Ser
1               5

<210> SEQ ID NO 6
<211> LENGTH: 8
<212> TYPE: PRT
```

```
<213> ORGANISM: Artificial
<220> FEATURE:
<223> OTHER INFORMATION: peptide linker

<400> SEQUENCE: 6

Gly Gly Arg Arg Gly Gly Gly Ser
1               5

<210> SEQ ID NO 7
<211> LENGTH: 9
<212> TYPE: PRT
<213> ORGANISM: Artificial
<220> FEATURE:
<223> OTHER INFORMATION: peptide linker

<400> SEQUENCE: 7

Leu Arg Gln Arg Asp Gly Glu Arg Pro
1               5

<210> SEQ ID NO 8
<211> LENGTH: 12
<212> TYPE: PRT
<213> ORGANISM: Artificial
<220> FEATURE:
<223> OTHER INFORMATION: peptide linker

<400> SEQUENCE: 8

Leu Arg Gln Lys Asp Gly Gly Gly Ser Glu Arg Pro
1               5                   10

<210> SEQ ID NO 9
<211> LENGTH: 16
<212> TYPE: PRT
<213> ORGANISM: Artificial
<220> FEATURE:
<223> OTHER INFORMATION: peptide linker

<400> SEQUENCE: 9

Leu Arg Gln Lys Asp Gly Gly Gly Ser Gly Gly Gly Ser Glu Arg Pro
1               5                   10                  15

<210> SEQ ID NO 10
<211> LENGTH: 30
<212> TYPE: PRT
<213> ORGANISM: Artificial
<220> FEATURE:
<223> OTHER INFORMATION: DNA binding domain of the mouse transcription
      factor Zif268 F1

<400> SEQUENCE: 10

Tyr Ala Cys Pro Val Glu Ser Cys Asp Arg Arg Phe Ser Arg Ser Asp
1               5                   10                  15

Glu Leu Thr Arg His Ile Arg Ile His Thr Gly Gln Lys Pro
            20                  25                  30

<210> SEQ ID NO 11
<211> LENGTH: 28
<212> TYPE: PRT
<213> ORGANISM: Artificial
<220> FEATURE:
<223> OTHER INFORMATION: DNA binding domain of the mouse transcription
      factor Zif268 F2

<400> SEQUENCE: 11

Phe Gln Cys Arg Ile Cys Met Arg Asn Phe Ser Arg Ser Asp His Leu
1               5                   10                  15
```

```
Thr Thr His Ile Arg Thr His Thr Gly Glu Lys Pro
            20                  25
```

```
<210> SEQ ID NO 12
<211> LENGTH: 27
<212> TYPE: PRT
<213> ORGANISM: Artificial
<220> FEATURE:
<223> OTHER INFORMATION: DNA binding domain of the mouse transcription
      factor Zif268 F3

<400> SEQUENCE: 12

Phe Ala Cys Asp Ile Cys Gly Arg Lys Phe Ala Arg Ser Asp Glu Arg
1               5                   10                  15

Lys Arg His Thr Lys Ile His Leu Arg Gln Lys
            20                  25

<210> SEQ ID NO 13
<211> LENGTH: 9
<212> TYPE: DNA
<213> ORGANISM: Artificial
<220> FEATURE:
<223> OTHER INFORMATION: target DNA

<400> SEQUENCE: 13 gcgtgggcg                                                              9

<210> SEQ ID NO 14
<211> LENGTH: 9
<212> TYPE: DNA
<213> ORGANISM: Artificial
<220> FEATURE:
<223> OTHER INFORMATION: target DNA

<400> SEQUENCE: 14 ggggcgggg                                                              9

<210> SEQ ID NO 15
<211> LENGTH: 18
<212> TYPE: DNA
<213> ORGANISM: Artificial
<220> FEATURE:
<223> OTHER INFORMATION: SBS-6439 target DNA

<400> SEQUENCE: 15
gacatggcca tggatagc                                                   18

<210> SEQ ID NO 16
<211> LENGTH: 19
<212> TYPE: DNA
<213> ORGANISM: Artificial
<220> FEATURE:
<223> OTHER INFORMATION: SBS-6576 target DNA

<400> SEQUENCE: 16
gattggtaca agagtgggg                                                  19

<210> SEQ ID NO 17
<211> LENGTH: 19
<212> TYPE: DNA
<213> ORGANISM: Artificial
<220> FEATURE:
<223> OTHER INFORMATION: SBS-6435 target DNA

<400> SEQUENCE: 17
tcactggagg cggctttgg                                                  19
```

<210> SEQ ID NO 18
<211> LENGTH: 19
<212> TYPE: DNA
<213> ORGANISM: Artificial
<220> FEATURE:
<223> OTHER INFORMATION: SBS-6437 target DNA

<400> SEQUENCE: 18
ttcaaggatc tgagctgcg                                              19

<210> SEQ ID NO 19
<211> LENGTH: 19
<212> TYPE: DNA
<213> ORGANISM: Artificial
<220> FEATURE:
<223> OTHER INFORMATION: SBS-6624 target DNA

<400> SEQUENCE: 19
agacaggatt caaatccag                                              19

<210> SEQ ID NO 20
<211> LENGTH: 7
<212> TYPE: PRT
<213> ORGANISM: Artificial
<220> FEATURE:
<223> OTHER INFORMATION: SBS-6439 F1

<400> SEQUENCE: 20

Thr Ser Ala Asp Leu Thr Glu
1               5

<210> SEQ ID NO 21
<211> LENGTH: 7
<212> TYPE: PRT
<213> ORGANISM: Artificial
<220> FEATURE:
<223> OTHER INFORMATION: SBS-6439 F2

<400> SEQUENCE: 21

Ala Ser Ala Asn Leu Ser Arg
1               5

<210> SEQ ID NO 22
<211> LENGTH: 7
<212> TYPE: PRT
<213> ORGANISM: Artificial
<220> FEATURE:
<223> OTHER INFORMATION: SBS-6439 F3

<400> SEQUENCE: 22

Arg Ser Asp Ala Leu Ser Thr
1               5

<210> SEQ ID NO 23
<211> LENGTH: 7
<212> TYPE: PRT
<213> ORGANISM: Artificial
<220> FEATURE:
<223> OTHER INFORMATION: SBS-6439 F4

<400> SEQUENCE: 23

Asp Arg Ser Thr Arg Thr Lys
1               5

<210> SEQ ID NO 24

```
<211> LENGTH: 7
<212> TYPE: PRT
<213> ORGANISM: Artificial
<220> FEATURE:
<223> OTHER INFORMATION: SBS-6439 F5

<400> SEQUENCE: 24

Arg Ser Asp Val Leu Ser Ala
1               5

<210> SEQ ID NO 25
<211> LENGTH: 7
<212> TYPE: PRT
<213> ORGANISM: Artificial
<220> FEATURE:
<223> OTHER INFORMATION: SBS-6439 F6

<400> SEQUENCE: 25

Asp Arg Ser Asn Arg Ile Lys
1               5

<210> SEQ ID NO 26
<211> LENGTH: 7
<212> TYPE: PRT
<213> ORGANISM: Artificial
<220> FEATURE:
<223> OTHER INFORMATION: SBS-6435 F1

<400> SEQUENCE: 26

Arg Ser Asp Ser Leu Ser Thr
1               5

<210> SEQ ID NO 27
<211> LENGTH: 7
<212> TYPE: PRT
<213> ORGANISM: Artificial
<220> FEATURE:
<223> OTHER INFORMATION: SBS-6435 F2

<400> SEQUENCE: 27

Ala Ser Ala Asn Leu Ser Arg
1               5

<210> SEQ ID NO 28
<211> LENGTH: 7
<212> TYPE: PRT
<213> ORGANISM: Artificial
<220> FEATURE:
<223> OTHER INFORMATION: SBS-6435 F3

<400> SEQUENCE: 28

Arg Ser Asp Asp Leu Ser Arg
1               5

<210> SEQ ID NO 29
<211> LENGTH: 7
<212> TYPE: PRT
<213> ORGANISM: Artificial
<220> FEATURE:
<223> OTHER INFORMATION: SBS-6435 F4

<400> SEQUENCE: 29

Arg Asn Asp Asn Arg Thr Lys
1               5

<210> SEQ ID NO 30
<211> LENGTH: 7
```

```
<212> TYPE: PRT
<213> ORGANISM: Artificial
<220> FEATURE:
<223> OTHER INFORMATION: SBS-6435 F5

<400> SEQUENCE: 30

Arg Ser Asp Ala Leu Ser Glu
1               5

<210> SEQ ID NO 31
<211> LENGTH: 7
<212> TYPE: PRT
<213> ORGANISM: Artificial
<220> FEATURE:
<223> OTHER INFORMATION: SBS-6435 F6

<400> SEQUENCE: 31

Arg Ser Ser Asp Arg Thr Lys
1               5

<210> SEQ ID NO 32
<211> LENGTH: 7
<212> TYPE: PRT
<213> ORGANISM: Artificial
<220> FEATURE:
<223> OTHER INFORMATION: SBS-6437

<400> SEQUENCE: 32

Arg Ser Asp Thr Leu Ser Thr
1               5

<210> SEQ ID NO 33
<211> LENGTH: 7
<212> TYPE: PRT
<213> ORGANISM: Artificial
<220> FEATURE:
<223> OTHER INFORMATION: SBS-6437 F2

<400> SEQUENCE: 33

Arg Ser Ala Asp Arg Lys Arg
1               5

<210> SEQ ID NO 34
<211> LENGTH: 7
<212> TYPE: PRT
<213> ORGANISM: Artificial
<220> FEATURE:
<223> OTHER INFORMATION: SBS-6437 F3

<400> SEQUENCE: 34

Arg Ser Lys Thr Leu Ser Glu
1               5

<210> SEQ ID NO 35
<211> LENGTH: 7
<212> TYPE: PRT
<213> ORGANISM: Artificial
<220> FEATURE:
<223> OTHER INFORMATION: SBS-6437 F4

<400> SEQUENCE: 35

Ala Asn Ser Asn Arg Ile Lys
1               5

<210> SEQ ID NO 36
<211> LENGTH: 7
<212> TYPE: PRT
```

```
<213> ORGANISM: Artificial
<220> FEATURE:
<223> OTHER INFORMATION: SBS-6437 F5

<400> SEQUENCE: 36

Arg Ser Asp Asn Leu Ser Thr
1               5

<210> SEQ ID NO 37
<211> LENGTH: 7
<212> TYPE: PRT
<213> ORGANISM: Artificial
<220> FEATURE:
<223> OTHER INFORMATION: SBS-6437 F6

<400> SEQUENCE: 37

Asp Ser Ser Ser Arg Ile Lys
1               5

<210> SEQ ID NO 38
<211> LENGTH: 7
<212> TYPE: PRT
<213> ORGANISM: Artificial
<220> FEATURE:
<223> OTHER INFORMATION: SBS-6576 F1

<400> SEQUENCE: 38

Arg Ser Asp His Leu Ser Gln
1               5

<210> SEQ ID NO 39
<211> LENGTH: 7
<212> TYPE: PRT
<213> ORGANISM: Artificial
<220> FEATURE:
<223> OTHER INFORMATION: SBS-6576 F2

<400> SEQUENCE: 39

Arg Ser Asp Val Arg Lys Asn
1               5

<210> SEQ ID NO 40
<211> LENGTH: 7
<212> TYPE: PRT
<213> ORGANISM: Artificial
<220> FEATURE:
<223> OTHER INFORMATION: SBS-6576 F3

<400> SEQUENCE: 40

Arg Ser Asp Ala Leu Ser Val
1               5

<210> SEQ ID NO 41
<211> LENGTH: 7
<212> TYPE: PRT
<213> ORGANISM: Artificial
<220> FEATURE:
<223> OTHER INFORMATION: SBS-6576 F4

<400> SEQUENCE: 41

Asp Asn Ala Asn Arg Thr Lys
1               5

<210> SEQ ID NO 42
<211> LENGTH: 7
<212> TYPE: PRT
<213> ORGANISM: Artificial
```

```
<220> FEATURE:
<223> OTHER INFORMATION: SBS-6576 F5

<400> SEQUENCE: 42

Arg Ser Asp His Leu Ser Thr
1               5

<210> SEQ ID NO 43
<211> LENGTH: 7
<212> TYPE: PRT
<213> ORGANISM: Artificial
<220> FEATURE:
<223> OTHER INFORMATION: SBS-6576 F6

<400> SEQUENCE: 43

Thr Ser Ser Asn Arg Thr Lys
1               5

<210> SEQ ID NO 44
<211> LENGTH: 7
<212> TYPE: PRT
<213> ORGANISM: Artificial
<220> FEATURE:
<223> OTHER INFORMATION: SBS-6624 F1

<400> SEQUENCE: 44

Arg Ser Asp Asn Leu Ser Glu
1               5

<210> SEQ ID NO 45
<211> LENGTH: 7
<212> TYPE: PRT
<213> ORGANISM: Artificial
<220> FEATURE:
<223> OTHER INFORMATION: SBS-6624 F2

<400> SEQUENCE: 45

His Ser Arg Ser Arg Lys Thr
1               5

<210> SEQ ID NO 46
<211> LENGTH: 7
<212> TYPE: PRT
<213> ORGANISM: Artificial
<220> FEATURE:
<223> OTHER INFORMATION: SBS-6624 F3

<400> SEQUENCE: 46

Asp Ser Glu Ser Leu Asn Ala
1               5

<210> SEQ ID NO 47
<211> LENGTH: 7
<212> TYPE: PRT
<213> ORGANISM: Artificial
<220> FEATURE:
<223> OTHER INFORMATION: SBS-6624 F4

<400> SEQUENCE: 47

Thr Ser Ser Asn Leu Ser Arg
1               5

<210> SEQ ID NO 48
<211> LENGTH: 7
<212> TYPE: PRT
<213> ORGANISM: Artificial
<220> FEATURE:
```

```
<223> OTHER INFORMATION: SBS-6624 F5

<400> SEQUENCE: 48

Arg Ser Asp Asn Leu Ser Gln
1               5

<210> SEQ ID NO 49
<211> LENGTH: 7
<212> TYPE: PRT
<213> ORGANISM: Artificial
<220> FEATURE:
<223> OTHER INFORMATION: SBS-6624 F6

<400> SEQUENCE: 49

Gln Arg Gln His Arg Lys Thr
1               5

<210> SEQ ID NO 50
<211> LENGTH: 23
<212> TYPE: DNA
<213> ORGANISM: Artificial
<220> FEATURE:
<223> OTHER INFORMATION: oligo rPLN-57F

<400> SEQUENCE: 50
agtctgcatt gtgacgatca cag                                               23

<210> SEQ ID NO 51
<211> LENGTH: 16
<212> TYPE: DNA
<213> ORGANISM: Artificial
<220> FEATURE:
<223> OTHER INFORMATION: oligo rPLN-125R

<400> SEQUENCE: 51
gcaggcagcc aaacgc                                                       16

<210> SEQ ID NO 52
<211> LENGTH: 28
<212> TYPE: DNA
<213> ORGANISM: Artificial
<220> FEATURE:
<223> OTHER INFORMATION: oligo rPLN-81T

<400> SEQUENCE: 52
agccaaggcc tcctaaaagg agacagct                                          28

<210> SEQ ID NO 53
<211> LENGTH: 21
<212> TYPE: DNA
<213> ORGANISM: Artificial
<220> FEATURE:
<223> OTHER INFORMATION: oligo mGAPDH-F1

<400> SEQUENCE: 53
cccatgtttg tgatgggtgt g                                                 21

<210> SEQ ID NO 54
<211> LENGTH: 18
<212> TYPE: DNA
<213> ORGANISM: Artificial
<220> FEATURE:
<223> OTHER INFORMATION: oligo mGAPDH-R1

<400> SEQUENCE: 54
catggactgt ggtcatga                                                     18
```

<210> SEQ ID NO 55
<211> LENGTH: 24
<212> TYPE: DNA
<213> ORGANISM: Artificial
<220> FEATURE:
<223> OTHER INFORMATION: oligo mGAPDH-P1

<400> SEQUENCE: 55
atcctgcacc accaactgct tagc                                          24

<210> SEQ ID NO 56
<211> LENGTH: 23
<212> TYPE: DNA
<213> ORGANISM: Artificial
<220> FEATURE:
<223> OTHER INFORMATION: oligo hPLN-F56

<400> SEQUENCE: 56
tctatactgt gatgatcaca gct                                           23

<210> SEQ ID NO 57
<211> LENGTH: 20
<212> TYPE: DNA
<213> ORGANISM: Artificial
<220> FEATURE:
<223> OTHER INFORMATION: oligo hPLN-R173

<400> SEQUENCE: 57
caggacagga agtctgaagt                                               20

<210> SEQ ID NO 58
<211> LENGTH: 28
<212> TYPE: DNA
<213> ORGANISM: Artificial
<220> FEATURE:
<223> OTHER INFORMATION: oligo hPLN-PF119L

<400> SEQUENCE: 58
ctgccagctt tttatctttc tctcgacc                                      28

<210> SEQ ID NO 59
<211> LENGTH: 21
<212> TYPE: DNA
<213> ORGANISM: Artificial
<220> FEATURE:
<223> OTHER INFORMATION: oligo hGAPDH-Fo1

<400> SEQUENCE: 59
ccatgttcgt catgggtgtg a                                             21

<210> SEQ ID NO 60
<211> LENGTH: 20
<212> TYPE: DNA
<213> ORGANISM: Artificial
<220> FEATURE:
<223> OTHER INFORMATION: oligo hGAPDH-Re1

<400> SEQUENCE: 60
catggactgt ggtcatgagt                                               20

<210> SEQ ID NO 61
<211> LENGTH: 24
<212> TYPE: DNA
<213> ORGANISM: Artificial
<220> FEATURE:

<223> OTHER INFORMATION: oligo hGAPDH-Pr1

<400> SEQUENCE: 61
tcctgcacca ccaactgctt agca                                   24

<210> SEQ ID NO 62
<211> LENGTH: 20
<212> TYPE: DNA
<213> ORGANISM: Artificial
<220> FEATURE:
<223> OTHER INFORMATION: oligo koxFor2

<400> SEQUENCE: 62
ggttggagaa gggagaagag                                        20

<210> SEQ ID NO 63
<211> LENGTH: 22
<212> TYPE: DNA
<213> ORGANISM: Artificial
<220> FEATURE:
<223> OTHER INFORMATION: oligo FLAG-Rev

<400> SEQUENCE: 63
tacttgtcat cgtcgtcctt gt                                     22

<210> SEQ ID NO 64
<211> LENGTH: 25
<212> TYPE: DNA
<213> ORGANISM: Artificial
<220> FEATURE:
<223> OTHER INFORMATION: oligo Kox-Pro2

<400> SEQUENCE: 64
caccaagaga cccatcctga ttcag                                  25

<210> SEQ ID NO 65
<211> LENGTH: 22
<212> TYPE: DNA
<213> ORGANISM: Artificial
<220> FEATURE:
<223> OTHER INFORMATION: oligo 18S-For1

<400> SEQUENCE: 65
ttccgataac gaacgagact ct                                     22

<210> SEQ ID NO 66
<211> LENGTH: 19
<212> TYPE: DNA
<213> ORGANISM: Artificial
<220> FEATURE:
<223> OTHER INFORMATION: oligo 18S-Rev1

<400> SEQUENCE: 66
tggctgaacg ccacttgtc                                         19

<210> SEQ ID NO 67
<211> LENGTH: 23
<212> TYPE: DNA
<213> ORGANISM: Artificial
<220> FEATURE:
<223> OTHER INFORMATION: oligo 18S Pro1

<400> SEQUENCE: 67
taactagtta cgcgaccccc gag                                    23

```
<210> SEQ ID NO 68
<211> LENGTH: 305
<212> TYPE: PRT
<213> ORGANISM: Artificial
<220> FEATURE:
<223> OTHER INFORMATION: Fusion Protein Comprising SBS-6439

<400> SEQUENCE: 68

Met Ala Pro Lys Lys Arg Lys Val Gly Ile His Gly Val Pro Ala
1               5                   10                  15

Ala Met Ala Glu Arg Pro Tyr Ala Cys Pro Val Glu Ser Cys Asp Arg
            20                  25                  30

Arg Phe Ser Thr Ser Ala Asp Leu Thr Glu His Ile Arg Ile His Thr
                35                  40                  45

Gly Gln Lys Pro Phe Gln Cys Arg Ile Cys Met Arg Asn Phe Ser Ala
        50                  55                  60

Ser Ala Asn Leu Ser Arg His Ile Arg Thr His Thr Gly Gly Glu Arg
65                  70                  75                  80

Pro Phe Gln Cys Arg Ile Cys Met Arg Asn Phe Ser Arg Ser Asp Ala
                85                  90                  95

Leu Ser Thr His Ile Arg Thr His Thr Gly Glu Lys Pro Phe Ala Cys
            100                 105                 110

Asp Ile Cys Gly Arg Lys Phe Ala Asp Arg Ser Thr Arg Thr Lys His
            115                 120                 125

Thr Lys Ile His Thr Gly Ser Gln Lys Pro Phe Gln Cys Arg Ile Cys
    130                 135                 140

Met Arg Asn Phe Ser Arg Ser Asp Val Leu Ser Ala His Ile Arg Thr
145                 150                 155                 160

His Thr Gly Glu Lys Pro Phe Ala Cys Asp Ile Cys Gly Lys Lys Phe
                165                 170                 175

Ala Asp Arg Ser Asn Arg Ile Lys His Thr Lys Ile His Leu Arg Gln
            180                 185                 190

Lys Asp Ala Ala Arg Gly Ser Gly Met Asp Ala Lys Ser Leu Thr Ala
        195                 200                 205

Trp Ser Arg Thr Leu Val Thr Phe Lys Asp Val Phe Val Asp Phe Thr
210                 215                 220

Arg Glu Glu Trp Lys Leu Leu Asp Thr Ala Gln Gln Ile Val Tyr Arg
225                 230                 235                 240

Asn Val Met Leu Glu Asn Tyr Lys Asn Leu Val Ser Leu Gly Tyr Gln
                245                 250                 255

Leu Thr Lys Pro Asp Val Ile Leu Arg Leu Glu Lys Gly Glu Glu Pro
            260                 265                 270

Trp Leu Val Glu Arg Glu Ile His Gln Glu Thr His Pro Asp Ser Glu
        275                 280                 285

Thr Ala Phe Glu Ile Lys Ser Ser Val Asp Tyr Lys Asp Asp Asp Asp
    290                 295                 300

Lys
305

<210> SEQ ID NO 69
<211> LENGTH: 306
<212> TYPE: PRT
<213> ORGANISM: Artificial
<220> FEATURE:
<223> OTHER INFORMATION: Fusion Protein Comprising SBS-6576

<400> SEQUENCE: 69
```

```
Met Ala Pro Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp His Leu Ser Gln His Ile Arg Thr His Thr Gly Glu
        35                  40                  45

Lys Pro Phe Ala Cys Asp Ile Cys Gly Lys Lys Phe Ala Arg Ser Asp
    50                  55                  60

Val Arg Lys Asn His Thr Lys Ile His Thr Gly Gly Gly Ser Gln
65              70                  75                  80

Arg Pro Phe Gln Cys Arg Ile Cys Met Arg Asn Phe Ser Arg Ser Asp
                85                  90                  95

Ala Leu Ser Val His Ile Arg Thr His Thr Gly Glu Lys Pro Phe Ala
            100                 105                 110

Cys Asp Ile Cys Gly Arg Lys Phe Ala Asp Asn Ala Asn Arg Thr Lys
            115                 120                 125

His Thr Lys Ile His Thr Gly Ser Gln Lys Pro Phe Gln Cys Arg Ile
    130                 135                 140

Cys Met Arg Asn Phe Ser Arg Ser Asp His Leu Ser Thr His Ile Arg
145                 150                 155                 160

Thr His Thr Gly Glu Lys Pro Phe Ala Cys Asp Ile Cys Gly Arg Lys
                165                 170                 175

Phe Ala Thr Ser Ser Asn Arg Thr Lys His Thr Lys Ile His Leu Arg
            180                 185                 190

Gln Lys Asp Ala Ala Arg Gly Ser Gly Met Asp Ala Lys Ser Leu Thr
        195                 200                 205

Ala Trp Ser Arg Thr Leu Val Thr Phe Lys Asp Val Phe Val Asp Phe
    210                 215                 220

Thr Arg Glu Glu Trp Lys Leu Leu Asp Thr Ala Gln Gln Ile Val Tyr
225                 230                 235                 240

Arg Asn Val Met Leu Glu Asn Tyr Lys Asn Leu Val Ser Leu Gly Tyr
                245                 250                 255

Gln Leu Thr Lys Pro Asp Val Ile Leu Arg Leu Glu Lys Gly Glu Glu
            260                 265                 270

Pro Trp Leu Val Glu Arg Glu Ile His Gln Glu Thr His Pro Asp Ser
    275                 280                 285

Glu Thr Ala Phe Glu Ile Lys Ser Ser Val Asp Tyr Lys Asp Asp Asp
    290                 295                 300

Asp Lys
305

<210> SEQ ID NO 70
<211> LENGTH: 9
<212> TYPE: DNA
<213> ORGANISM: Artificial
<220> FEATURE:
<223> OTHER INFORMATION: target DNA

<400> SEQUENCE: 70 gaggcggcg                                                              9

<210> SEQ ID NO 71
<211> LENGTH: 7
<212> TYPE: PRT
<213> ORGANISM: Artificial
<220> FEATURE:
<223> OTHER INFORMATION: SBS-1563 F1
```

```
<400> SEQUENCE: 71

Arg Ser Asp Glu Leu Thr Arg
1               5

<210> SEQ ID NO 72
<211> LENGTH: 7
<212> TYPE: PRT
<213> ORGANISM: Artificial
<220> FEATURE:
<223> OTHER INFORMATION: SBS-1563 F2

<400> SEQUENCE: 72

Arg Ser Asp Glu Leu Gln Arg
1               5

<210> SEQ ID NO 73
<211> LENGTH: 7
<212> TYPE: PRT
<213> ORGANISM: Artificial
<220> FEATURE:
<223> OTHER INFORMATION: SBS-1563 F3

<400> SEQUENCE: 73

Arg Ser Asp Asn Leu Thr Arg
1               5

<210> SEQ ID NO 74
<211> LENGTH: 20
<212> TYPE: DNA
<213> ORGANISM: Artificial
<220> FEATURE:
<223> OTHER INFORMATION: target DNA

<400> SEQUENCE: 74
agattggtac aagagtgggg                                              20

<210> SEQ ID NO 75
<211> LENGTH: 19
<212> TYPE: DNA
<213> ORGANISM: Artificial
<220> FEATURE:
<223> OTHER INFORMATION: target DNA

<400> SEQUENCE: 75
gattggtaca agagtgggg                                               19

<210> SEQ ID NO 76
<211> LENGTH: 7
<212> TYPE: PRT
<213> ORGANISM: Artificial
<220> FEATURE:
<223> OTHER INFORMATION: SBS-6577 F1

<400> SEQUENCE: 76

Arg Ser Asp His Leu Ser Gln
1               5

<210> SEQ ID NO 77
<211> LENGTH: 7
<212> TYPE: PRT
<213> ORGANISM: Artificial
<220> FEATURE:
<223> OTHER INFORMATION: SBS-6577 F2

<400> SEQUENCE: 77
```

```
Arg Ser Asp Val Arg Lys Asn
1               5

<210> SEQ ID NO 78
<211> LENGTH: 7
<212> TYPE: PRT
<213> ORGANISM: Artificial
<220> FEATURE:
<223> OTHER INFORMATION: SBS-6577 F3

<400> SEQUENCE: 78

Arg Ser Asp Ala Leu Ser Val
1               5

<210> SEQ ID NO 79
<211> LENGTH: 7
<212> TYPE: PRT
<213> ORGANISM: Artificial
<220> FEATURE:
<223> OTHER INFORMATION: SBS-6577 F4

<400> SEQUENCE: 79

Asp Asn Ala Asn Arg Thr Lys
1               5

<210> SEQ ID NO 80
<211> LENGTH: 7
<212> TYPE: PRT
<213> ORGANISM: Artificial
<220> FEATURE:
<223> OTHER INFORMATION: SBS-6577 F5

<400> SEQUENCE: 80

Arg Ser Asp Ala Leu Ser Thr
1               5

<210> SEQ ID NO 81
<211> LENGTH: 7
<212> TYPE: PRT
<213> ORGANISM: Artificial
<220> FEATURE:
<223> OTHER INFORMATION: SBS-6577 F6

<400> SEQUENCE: 81

Gln Asn Ser His Arg Lys Thr
1               5

<210> SEQ ID NO 82
<211> LENGTH: 7
<212> TYPE: PRT
<213> ORGANISM: Artificial
<220> FEATURE:
<223> OTHER INFORMATION: SBS-6578 F1

<400> SEQUENCE: 82

Arg Ser Asp His Leu Ser Gln
1               5

<210> SEQ ID NO 83
<211> LENGTH: 7
<212> TYPE: PRT
<213> ORGANISM: Artificial
<220> FEATURE:
<223> OTHER INFORMATION: SBS-6578 F2

<400> SEQUENCE: 83

Arg Ser Asp Val Arg Lys Asn
```

```
1               5
```

<210> SEQ ID NO 84
<211> LENGTH: 7
<212> TYPE: PRT
<213> ORGANISM: Artificial
<220> FEATURE:
<223> OTHER INFORMATION: SBS-6578 F3

<400> SEQUENCE: 84

```
Arg Ser Asp Ala Leu Ser Val
1               5
```

<210> SEQ ID NO 85
<211> LENGTH: 7
<212> TYPE: PRT
<213> ORGANISM: Artificial
<220> FEATURE:
<223> OTHER INFORMATION: SBS-6578 F4

<400> SEQUENCE: 85

```
Asp Asn Ala Asn Arg Thr Lys
1               5
```

<210> SEQ ID NO 86
<211> LENGTH: 7
<212> TYPE: PRT
<213> ORGANISM: Artificial
<220> FEATURE:
<223> OTHER INFORMATION: SBS-6578 F5

<400> SEQUENCE: 86

```
Thr Lys Leu His Leu Ile Glu
1               5
```

<210> SEQ ID NO 87
<211> LENGTH: 7
<212> TYPE: PRT
<213> ORGANISM: Artificial
<220> FEATURE:
<223> OTHER INFORMATION: SBS-6578 F6

<400> SEQUENCE: 87

```
Gln Ser Ala Asn Leu Ser Arg
1               5
```

<210> SEQ ID NO 88
<211> LENGTH: 25
<212> TYPE: PRT
<213> ORGANISM: Artificial
<220> FEATURE:
<223> OTHER INFORMATION: zinc finger motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:

<221> NAME/KEY: MISC_FEATURE
<222> LOCATION: (23)..(24)
<223> OTHER INFORMATION: Xaa may be any amino acid, Xaa may be present
      or absent

<400> SEQUENCE: 88

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 89
<211> LENGTH: 179
<212> TYPE: PRT
<213> ORGANISM: Artificial
<220> FEATURE:
<223> OTHER INFORMATION: zinc finger protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (23)..(24)
<223> OTHER INFORMATION: Xaa may be any amino acid, Xaa may be present
      or absent
<220> FEATURE:
<221> NAME/KEY: misc_feature
<222> LOCATION: (26)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (36)..(37)
<223> OTHER INFORMATION: Xaa may be any amino acid, Xaa may be present
      or absent
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: Xaa may be any amino acid, Xaa may be present
      or absent
<220> FEATURE:
<221> NAME/KEY: misc_feature
<222> LOCATION: (58)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: MISC_FEATURE
<222> LOCATION: (68)..(69)

```
<223> OTHER INFORMATION: Xaa may be any amino acid, Xaa may be present
      or absent
<220> FEATURE:
<221> NAME/KEY: misc_feature
<222> LOCATION: (71)..(75)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: MISC_FEATURE
<222> LOCATION: (87)..(88)
<223> OTHER INFORMATION: Xaa may be any amino acid, Xaa may be present
      or absent
<220> FEATURE:
<221> NAME/KEY: misc_feature
<222> LOCATION: (90)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: MISC_FEATURE
<222> LOCATION: (100)..(101)
<223> OTHER INFORMATION: Xaa may be any amino acid, Xaa may be present
      or absent
<220> FEATURE:
<221> NAME/KEY: misc_feature
<222> LOCATION: (103)..(107)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: MISC_FEATURE
<222> LOCATION: (119)..(120)
<223> OTHER INFORMATION: Xaa may be any amino acid, Xaa may be present
      or absent
<220> FEATURE:
<221> NAME/KEY: misc_feature
<222> LOCATION: (122)..(128)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: MISC_FEATURE
<222> LOCATION: (132)..(133)
<223> OTHER INFORMATION: Xaa may be any amino acid, Xaa may be present
      or absent
<220> FEATURE:
<221> NAME/KEY: misc_feature
<222> LOCATION: (135)..(139)
<223> OTHER INFORMATION: Xaa can be any naturally occurring amino acid
<220> FEATURE:
<221> NAME/KEY: misc_feature
<222> LOCATION: (148)..(150)
<223> OTHER INFORMATION: Xaa can be any naturally occurring amino acid
<220> FEATURE:
<221> NAME/KEY: MISC_FEATURE
<222> LOCATION: (151)..(152)
<223> OTHER INFORMATION: Xaa may be any amino acid, Xaa may be present
      or absent
<220> FEATURE:
<221> NAME/KEY: misc_feature
<222> LOCATION: (154)..(160)
<223> OTHER INFORMATION: Xaa can be any naturally occurring amino acid
<220> FEATURE:
<221> NAME/KEY: misc_feature
<222> LOCATION: (162)..(163)
<223> OTHER INFORMATION: Xaa can be any naturally occurring amino acid
<220> FEATURE:
<221> NAME/KEY: MISC_FEATURE
<222> LOCATION: (164)..(165)
<223> OTHER INFORMATION: Xaa may be any amino acid, Xaa may be present
``` or absent
<220> FEATURE:
<221> NAME/KEY: misc_feature
<222> LOCATION: (167)..(171)
<223> OTHER INFORMATION: Xaa can be any naturally occurring amino acid

<400> SEQUENCE: 89

Cys Xaa Xaa Xaa Xaa Cys Xaa Xaa Xaa Xaa Arg Ser Asp His Leu
1               5                   10                  15

Ser Gln His Xaa Xaa Xaa Xaa Xaa His Xaa Xaa Xaa Xaa Xaa Xaa
                20                  25                  30

Cys Xaa Xaa Xaa Xaa Cys Xaa Xaa Xaa Xaa Arg Ser Asp Val Arg
                35                  40                  45

Lys Asn His Xaa Xaa Xaa Xaa Xaa His Xaa Xaa Xaa Xaa Xaa Xaa
            50                  55                  60

Cys Xaa Xaa Xaa Xaa Cys Xaa Xaa Xaa Xaa Arg Ser Asp Ala Leu
65                  70                  75                  80

Ser Val His Xaa Xaa Xaa Xaa Xaa His Xaa Xaa Xaa Xaa Xaa Xaa
                85                  90                  95

Cys Xaa Xaa Xaa Xaa Cys Xaa Xaa Xaa Xaa Asp Asn Ala Asn Arg
                100                 105                 110

Thr Lys His Xaa Xaa Xaa Xaa Xaa His Xaa Xaa Xaa Xaa Xaa Xaa
            115                 120                 125

Cys Xaa Xaa Xaa Xaa Cys Xaa Xaa Xaa Xaa Arg Ser Asp His Leu
            130                 135                 140

Ser Thr His Xaa Xaa Xaa Xaa Xaa His Xaa Xaa Xaa Xaa Xaa Xaa
145                 150                 155                 160

Cys Xaa Xaa Xaa Xaa Cys Xaa Xaa Xaa Xaa Thr Ser Ser Asn Arg
                165                 170                 175

Thr Lys His

<210> SEQ ID NO 90
<211> LENGTH: 7
<212> TYPE: PRT
<213> ORGANISM: Artificial
<220> FEATURE:
<223> OTHER INFORMATION: first finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 90

Arg Xaa Xaa His Xaa Xaa Gln
1               5

<210> SEQ ID NO 91
<211> LENGTH: 7
<212> TYPE: PRT
<213> ORGANISM: Artificial
<220> FEATURE:
<223> OTHER INFORMATION: second finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

```
<400> SEQUENCE: 91

Arg Xaa Xaa Val Xaa Xaa Asn
1               5

<210> SEQ ID NO 92
<211> LENGTH: 7
<212> TYPE: PRT
<213> ORGANISM: Artificial
<220> FEATURE:
<223> OTHER INFORMATION: third finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 92

Arg Xaa Xaa Ala Xaa Xaa Val
1               5

<210> SEQ ID NO 93
<211> LENGTH: 7
<212> TYPE: PRT
<213> ORGANISM: Artificial
<220> FEATURE:
<223> OTHER INFORMATION: fourth finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 93

Asp Xaa Xaa Asn Xaa Xaa Lys
1               5

<210> SEQ ID NO 94
<211> LENGTH: 7
<212> TYPE: PRT
<213> ORGANISM: Artificial
<220> FEATURE:
<223> OTHER INFORMATION: fifth finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 94

Arg Xaa Xaa His Xaa Xaa Thr
1               5

<210> SEQ ID NO 95
<211> LENGTH: 7
<212> TYPE: PRT
<213> ORGANISM: Artificial
<220> FEATURE:
<223> OTHER INFORMATION: sixth finger
<220> FEATURE:
<221> NAME/KEY: misc_feature
<222> LOCATION: (2)..(3)
```

```
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 95

Thr Xaa Xaa Asn Xaa Xaa Lys
1               5

<210> SEQ ID NO 96
<211> LENGTH: 185
<212> TYPE: PRT
<213> ORGANISM: Artificial
<220> FEATURE:
<223> OTHER INFORMATION: zinc finger protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (23)..(24)
<223> OTHER INFORMATION: Xaa may be any amino acid, Xaa may be present
      or absent
<220> FEATURE:
<221> NAME/KEY: misc_feature
<222> LOCATION: (26)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (36)..(37)
<223> OTHER INFORMATION: Xaa may be any amino acid, Xaa may be present
      or absent
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: MISC_FEATURE
```

-continued

```
<222> LOCATION: (55)..(56)
<223> OTHER INFORMATION: Xaa may be any amino acid, Xaa may be present
      or absent
<220> FEATURE:
<221> NAME/KEY: misc_feature
<222> LOCATION: (58)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: MISC_FEATURE
<222> LOCATION: (68)..(69)
<223> OTHER INFORMATION: Xaa may be any amino acid, Xaa may be present
      or absent
<220> FEATURE:
<221> NAME/KEY: misc_feature
<222> LOCATION: (71)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: MISC_FEATURE
<222> LOCATION: (87)..(88)
<223> OTHER INFORMATION: Xaa may be any amino acid, Xaa may be present
      or absent
<220> FEATURE:
<221> NAME/KEY: misc_feature
<222> LOCATION: (90)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: MISC_FEATURE
<222> LOCATION: (100)..(101)
<223> OTHER INFORMATION: Xaa may be any amino acid, Xaa may be present
      or absent
<220> FEATURE:
<221> NAME/KEY: misc_feature
<222> LOCATION: (103)..(107)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: MISC_FEATURE
<222> LOCATION: (119)..(120)
<223> OTHER INFORMATION: Xaa may be any amino acid, Xaa may be present
      or absent
<220> FEATURE:
<221> NAME/KEY: misc_feature
<222> LOCATION: (122)..(128)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
```

<220> FEATURE:
<221> NAME/KEY: MISC_FEATURE
<222> LOCATION: (132)..(133)
<223> OTHER INFORMATION: Xaa may be any amino acid, Xaa may be present
      or absent
<220> FEATURE:
<221> NAME/KEY: misc_feature
<222> LOCATION: (135)..(139)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (148)..(150)
<223> OTHER INFORMATION: Xaa can be any naturally occurring amino acid
<220> FEATURE:
<221> NAME/KEY: MISC_FEATURE
<222> LOCATION: (151)..(152)
<223> OTHER INFORMATION: Xaa may be any amino acid, Xaa may be present
      or absent
<220> FEATURE:
<221> NAME/KEY: misc_feature
<222> LOCATION: (154)..(160)
<223> OTHER INFORMATION: Xaa can be any naturally occurring amino acid
<220> FEATURE:
<221> NAME/KEY: misc_feature
<222> LOCATION: (162)..(163)
<223> OTHER INFORMATION: Xaa can be any naturally occurring amino acid
<220> FEATURE:
<221> NAME/KEY: MISC_FEATURE
<222> LOCATION: (164)..(165)
<223> OTHER INFORMATION: Xaa may be any amino acid, Xaa may be present
      or absent
<220> FEATURE:
<221> NAME/KEY: misc_feature
<222> LOCATION: (167)..(171)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (180)..(182)
<223> OTHER INFORMATION: Xaa can be any naturally occurring amino acid
<220> FEATURE:
<221> NAME/KEY: MISC_FEATURE
<222> LOCATION: (183)..(184)
<223> OTHER INFORMATION: Xaa may be any amino acid, Xaa may be present
      or absent

<400> SEQUENCE: 96

Cys Xaa Xaa Xaa Xaa Cys Xaa Xaa Xaa Xaa Arg Xaa Xaa His Xaa
1               5                   10                  15

Xaa Gln His Xaa Xaa Xaa Xaa Xaa His Xaa Xaa Xaa Xaa Xaa Xaa
            20                  25                  30

Cys Xaa Xaa Xaa Xaa Cys Xaa Xaa Xaa Xaa Arg Xaa Xaa Val Xaa
        35                  40                  45

Xaa Asn His Xaa Xaa Xaa Xaa Xaa His Xaa Xaa Xaa Xaa Xaa Xaa
        50                  55                  60

Cys Xaa Xaa Xaa Xaa Cys Xaa Xaa Xaa Xaa Arg Xaa Xaa Ala Xaa
65                  70                  75                  80

Xaa Val His Xaa Xaa Xaa Xaa Xaa His Xaa Xaa Xaa Xaa Xaa Xaa

```
                        85                  90                  95
Cys Xaa Xaa Xaa Xaa Cys Xaa Xaa Xaa Xaa Asp Xaa Xaa Asn Xaa
            100                 105                 110

Xaa Lys His Xaa Xaa Xaa Xaa Xaa His Xaa Xaa Xaa Xaa Xaa Xaa
            115                 120                 125

Cys Xaa Xaa Xaa Xaa Cys Xaa Xaa Xaa Xaa Arg Xaa Xaa His Xaa
            130                 135                 140

Xaa Thr His Xaa Xaa Xaa Xaa Xaa His Xaa Xaa Xaa Xaa Xaa Xaa
145                 150                 155                 160

Cys Xaa Xaa Xaa Xaa Cys Xaa Xaa Xaa Xaa Thr Xaa Xaa Asn Xaa
            165                 170                 175

Xaa Lys His Xaa Xaa Xaa Xaa Xaa His
            180                 185

<210> SEQ ID NO 97
<211> LENGTH: 179
<212> TYPE: PRT
<213> ORGANISM: Artificial
<220> FEATURE:
<223> OTHER INFORMATION: zinc finger protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (23)..(24)
<223> OTHER INFORMATION: Xaa may be any amino acid, Xaa may be present
      or absent
<220> FEATURE:
<221> NAME/KEY: misc_feature
<222> LOCATION: (26)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (36)..(37)
<223> OTHER INFORMATION: Xaa may be any amino acid, Xaa may be present
      or absent
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: Xaa may be any amino acid, Xaa may be present
      or absent
<220> FEATURE:
<221> NAME/KEY: misc_feature
<222> LOCATION: (58)..(64)
<223> OTHER INFORMATION: Xaa can be any naturally occurring amino acid
```

```
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: MISC_FEATURE
<222> LOCATION: (68)..(69)
<223> OTHER INFORMATION: Xaa may be any amino acid, Xaa may be present
      or absent
<220> FEATURE:
<221> NAME/KEY: misc_feature
<222> LOCATION: (71)..(75)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: MISC_FEATURE
<222> LOCATION: (87)..(88)
<223> OTHER INFORMATION: Xaa may be any amino acid, Xaa may be present
      or absent
<220> FEATURE:
<221> NAME/KEY: misc_feature
<222> LOCATION: (90)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: MISC_FEATURE
<222> LOCATION: (100)..(101)
<223> OTHER INFORMATION: Xaa may be any amino acid, Xaa may be present
      or absent
<220> FEATURE:
<221> NAME/KEY: misc_feature
<222> LOCATION: (103)..(107)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: MISC_FEATURE
<222> LOCATION: (119)..(120)
<223> OTHER INFORMATION: Xaa may be any amino acid, Xaa may be present
      or absent
<220> FEATURE:
<221> NAME/KEY: misc_feature
<222> LOCATION: (122)..(128)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: MISC_FEATURE
<222> LOCATION: (132)..(133)
<223> OTHER INFORMATION: Xaa may be any amino acid, Xaa may be present
      or absent
<220> FEATURE:
<221> NAME/KEY: misc_feature
<222> LOCATION: (135)..(139)
<223> OTHER INFORMATION: Xaa can be any naturally occurring amino acid
<220> FEATURE:
<221> NAME/KEY: misc_feature
<222> LOCATION: (148)..(150)
<223> OTHER INFORMATION: Xaa can be any naturally occurring amino acid
<220> FEATURE:
<221> NAME/KEY: MISC_FEATURE
<222> LOCATION: (151)..(152)
<223> OTHER INFORMATION: Xaa may be any amino acid, Xaa may be present
      or absent
<220> FEATURE:
<221> NAME/KEY: misc_feature
<222> LOCATION: (154)..(160)
<223> OTHER INFORMATION: Xaa can be any naturally occurring amino acid
<220> FEATURE:
```

```
<221> NAME/KEY: misc_feature
<222> LOCATION: (162)..(163)
<223> OTHER INFORMATION: Xaa can be any naturally occurring amino acid
<220> FEATURE:
<221> NAME/KEY: MISC_FEATURE
<222> LOCATION: (164)..(165)
<223> OTHER INFORMATION: Xaa may be any amino acid, Xaa may be present
     or absent
<220> FEATURE:
<221> NAME/KEY: misc_feature
<222> LOCATION: (167)..(171)
<223> OTHER INFORMATION: Xaa can be any naturally occurring amino acid

<400> SEQUENCE: 97

Cys Xaa Xaa Xaa Xaa Cys Xaa Xaa Xaa Xaa Arg Ser Asp Asn Leu
1               5                   10                  15

Ser Glu His Xaa Xaa Xaa Xaa Xaa His Xaa Xaa Xaa Xaa Xaa Xaa
            20                  25                  30

Cys Xaa Xaa Xaa Xaa Cys Xaa Xaa Xaa Xaa His Ser Arg Ser Arg
        35                  40                  45

Lys Thr His Xaa Xaa Xaa Xaa Xaa His Xaa Xaa Xaa Xaa Xaa Xaa
            50                  55                  60

Cys Xaa Xaa Xaa Xaa Cys Xaa Xaa Xaa Xaa Asp Ser Glu Ser Leu
65                  70                  75                  80

Asn Ala His Xaa Xaa Xaa Xaa Xaa His Xaa Xaa Xaa Xaa Xaa Xaa
                85                  90                  95

Cys Xaa Xaa Xaa Xaa Cys Xaa Xaa Xaa Xaa Thr Ser Ser Asn Leu
                100                 105                 110

Ser Arg His Xaa Xaa Xaa Xaa Xaa His Xaa Xaa Xaa Xaa Xaa Xaa
            115                 120                 125

Cys Xaa Xaa Xaa Xaa Cys Xaa Xaa Xaa Xaa Arg Ser Asp Asn Leu
        130                 135                 140

Ser Gln His Xaa Xaa Xaa Xaa Xaa His Xaa Xaa Xaa Xaa Xaa Xaa
145                 150                 155                 160

Cys Xaa Xaa Xaa Xaa Cys Xaa Xaa Xaa Xaa Gln Arg Gln His Arg
                165                 170                 175

Lys Thr His

<210> SEQ ID NO 98
<211> LENGTH: 7
<212> TYPE: PRT
<213> ORGANISM: Artificial
<220> FEATURE:
<223> OTHER INFORMATION: first finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 98

Arg Xaa Xaa Asn Xaa Xaa Glu
1               5

<210> SEQ ID NO 99
<211> LENGTH: 7
<212> TYPE: PRT
<213> ORGANISM: Artificial
<220> FEATURE:
<223> OTHER INFORMATION: second finger
<220> FEATURE:
```

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 99

His Xaa Xaa Ser Xaa Xaa Lys
1               5

<210> SEQ ID NO 100
<211> LENGTH: 7
<212> TYPE: PRT
<213> ORGANISM: Artificial
<220> FEATURE:
<223> OTHER INFORMATION: third finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 100

Asp Xaa Xaa Ser Xaa Xaa Ala
1               5

<210> SEQ ID NO 101
<211> LENGTH: 7
<212> TYPE: PRT
<213> ORGANISM: Artificial
<220> FEATURE:
<223> OTHER INFORMATION: fourth finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 101

Thr Xaa Xaa Asn Xaa Xaa Arg
1               5

<210> SEQ ID NO 102
<211> LENGTH: 7
<212> TYPE: PRT
<213> ORGANISM: Artificial
<220> FEATURE:
<223> OTHER INFORMATION: fifth finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 102

Arg Xaa Xaa Asn Xaa Xaa Gln
1               5

<210> SEQ ID NO 103
<211> LENGTH: 7
```

-continued

```
<212> TYPE: PRT
<213> ORGANISM: Artificial
<220> FEATURE:
<223> OTHER INFORMATION: sixth finger
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 103

Gln Xaa Xaa His Xaa Xaa Thr
1               5

<210> SEQ ID NO 104
<211> LENGTH: 185
<212> TYPE: PRT
<213> ORGANISM: Artificial
<220> FEATURE:
<223> OTHER INFORMATION: zinc finger protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa may be any amino acid, Xaa may be present
      or absent
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (23)..(24)
<223> OTHER INFORMATION: Xaa may be any amino acid, Xaa may be present
      or absent
<220> FEATURE:
<221> NAME/KEY: misc_feature
<222> LOCATION: (26)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (36)..(37)
<223> OTHER INFORMATION: Xaa may be any amino acid, Xaa may be present
      or absent
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (48)..(49)
```

```
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: Xaa may be any amino acid, Xaa may be present
      or absent
<220> FEATURE:
<221> NAME/KEY: misc_feature
<222> LOCATION: (58)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: MISC_FEATURE
<222> LOCATION: (68)..(69)
<223> OTHER INFORMATION: Xaa may be any amino acid, Xaa may be present
      or absent
<220> FEATURE:
<221> NAME/KEY: misc_feature
<222> LOCATION: (71)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: MISC_FEATURE
<222> LOCATION: (87)..(88)
<223> OTHER INFORMATION: Xaa may be any amino acid, Xaa may be present
      or absent
<220> FEATURE:
<221> NAME/KEY: misc_feature
<222> LOCATION: (90)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: MISC_FEATURE
<222> LOCATION: (100)..(101)
<223> OTHER INFORMATION: Xaa may be any amino acid, Xaa may be present
      or absent
<220> FEATURE:
<221> NAME/KEY: misc_feature
<222> LOCATION: (103)..(107)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: MISC_FEATURE
<222> LOCATION: (119)..(120)
<223> OTHER INFORMATION: Xaa may be any amino acid, Xaa may be present
      or absent
<220> FEATURE:
```

```
<221> NAME/KEY: misc_feature
<222> LOCATION: (122)..(128)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: MISC_FEATURE
<222> LOCATION: (132)..(133)
<223> OTHER INFORMATION: Xaa may be any amino acid, Xaa may be present
      or absent
<220> FEATURE:
<221> NAME/KEY: misc_feature
<222> LOCATION: (135)..(139)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (148)..(150)
<223> OTHER INFORMATION: Xaa can be any naturally occurring amino acid
<220> FEATURE:
<221> NAME/KEY: MISC_FEATURE
<222> LOCATION: (151)..(152)
<223> OTHER INFORMATION: Xaa may be any amino acid, Xaa may be present
      or absent
<220> FEATURE:
<221> NAME/KEY: misc_feature
<222> LOCATION: (154)..(160)
<223> OTHER INFORMATION: Xaa can be any naturally occurring amino acid
<220> FEATURE:
<221> NAME/KEY: misc_feature
<222> LOCATION: (162)..(163)
<223> OTHER INFORMATION: Xaa can be any naturally occurring amino acid
<220> FEATURE:
<221> NAME/KEY: MISC_FEATURE
<222> LOCATION: (164)..(165)
<223> OTHER INFORMATION: Xaa may be any amino acid, Xaa may be present
      or absent
<220> FEATURE:
<221> NAME/KEY: misc_feature
<222> LOCATION: (167)..(171)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (180)..(182)
<223> OTHER INFORMATION: Xaa can be any naturally occurring amino acid
<220> FEATURE:
<221> NAME/KEY: MISC_FEATURE
<222> LOCATION: (183)..(184)
<223> OTHER INFORMATION: Xaa may be any amino acid, Xaa may be present
      or absent

<400> SEQUENCE: 104

Cys Xaa Xaa Xaa Xaa Cys Xaa Xaa Xaa Xaa Arg Xaa Xaa Asn Xaa
1               5                   10                  15

Xaa Glu His Xaa Xaa Xaa Xaa Xaa His Xaa Xaa Xaa Xaa Xaa Xaa
            20                  25                  30

Cys Xaa Xaa Xaa Xaa Cys Xaa Xaa Xaa Xaa Xaa His Xaa Xaa Ser Xaa
        35                  40                  45
```

```
-continued

Xaa Lys His Xaa Xaa Xaa Xaa His Xaa Xaa Xaa Xaa Xaa Xaa
    50                  55              60

Cys Xaa Xaa Xaa Xaa Cys Xaa Xaa Xaa Xaa Asp Xaa Xaa Ser Xaa
65                  70              75              80

Xaa Ala His Xaa Xaa Xaa Xaa His Xaa Xaa Xaa Xaa Xaa Xaa
            85                  90              95

Cys Xaa Xaa Xaa Xaa Cys Xaa Xaa Xaa Xaa Thr Xaa Xaa Asn Xaa
                100             105             110

Xaa Arg His Xaa Xaa Xaa Xaa His Xaa Xaa Xaa Xaa Xaa Xaa
        115             120             125

Cys Xaa Xaa Xaa Xaa Cys Xaa Xaa Xaa Xaa Arg Xaa Xaa Asn Xaa
    130             135             140

Xaa Gln His Xaa Xaa Xaa Xaa His Xaa Xaa Xaa Xaa Xaa Xaa
145             150             155             160

Cys Xaa Xaa Xaa Xaa Cys Xaa Xaa Xaa Xaa Gln Xaa Xaa His Xaa
                165             170             175

Xaa Thr His Xaa Xaa Xaa Xaa His
            180             185
```

METHODS AND COMPOSITIONS FOR MODULATING CARDIAC CONTRACTILITY

CROSS REFERENCE TO RELATED APPLICATIONS

This application claims the benefit of U.S. provisional applications 60/560,529 (filed Apr. 8, 2004) and 60/574,039 (filed May 25, 2004); the disclosures of which are incorporated by reference in their entireties for all purposes.

BACKGROUND

Heart failure afflicts more than two million Americans, and congestive heart failure is recognized as the most common cause of hospitalization and mortality in Western society. Congestive heart failure is a syndrome characterized by left ventricular dysfunction, reduced exercise tolerance, impaired quality of life and dramatically shortened life expectancy. Decreased contractility of the left ventricle leads to reduced cardiac output with consequent systemic arterial and venous vasoconstriction.

Contractility appears to be regulated primarily by calcium flow. For the heart to contract, calcium must be released into the main body (sarcoplasm) of cardiac cells. The more calcium that flows in, the stronger the force of contraction. When the heart relaxes, calcium is pumped out of the sarcoplasm into the sarcoplasmic reticulum (SR). Thus, the heart muscle is triggered to contract and relax by a mechanism in which calcium ($Ca^{2+}$) is released from a reservoir into the muscle cell, or myocyte, and then rapidly pumped back into the reservoir, called the sarcoplasmic reticulum (SR) by the Sarco (endo)plasmic reticulum $Ca^{2+}$-ATPase 2a (SERCA2a).

The efficiency with which $Ca^{2+}$ is returned to SR determines the amount of $Ca^{2+}$ that is available for the next contraction. Phospholamban (PLN) is a regulatory phosphoprotein that modulates the active transport of Ca2+ by the cardiac sarcoplasmic reticular Ca(2+)-ATPase enzyme (SERCA2) into the lumen of the sarcoplasmic reticulum. Phospholamban, which is a reversible inhibitor of SERCA2, represses the enzyme's activity, and this inhibition is relieved upon phosphorylation of PLN in response to β-adrenergic stimulation.

The ratio of phospholamban to SERCA2 appears to be critical in regulating myocardial contractility, and alterations in this ratio may contribute to the functional deterioration observed during heart failure. (Koss et al. (1997) Basic Res Cardiol. 1997;92 Suppl 1:17-24). In particular, a decreased SERCA2a/PLN ratio, which is commonly observed in heart failure, leads to reduced SR $Ca^{2+}$ reserve and weakened contractility. The importance of the SERCA2a:PLN ratio to contractility has also been examined using PLN knockout mice; murine heart failure models (e.g., models that overexpress SERCA2a, as well as in isolated human cardiomyocytes (e.g., antisense-mediated PLN inhibition in myocytes that overexpress SERCA2a). See, e.g., MacLennan et al. (2003) *Nat Rev Mol Cell Biol.* 4(7):566-77; Eizema et al. (2000) *Circulation* 101(18):2193-9; del Monte et al. (2002) *Circulation* 105(8): 904-7; Minamisawa et al. (1999) *Cell* 99(3):313-22.

However, modulation of PLN expression so as to modulate cardiac contractility has not been previously described. Furthermore, the ability to alter cardiac contractility by modulating PLN expression may have utility in treating and/or preventing congestive heart failure and/or other cardiac diseases.

SUMMARY

A variety of zinc finger proteins (ZFPs) and methods utilizing such proteins are provided for use in treating heart failure. In particular, ZFPs that bind to a target site in a phospholamban (PLN) gene are described. The ZFPs can be fused to a regulatory domain as part of a fusion protein. By selecting either an activation domain or a repression domain for fusion with the ZFP, one can either activate or repress gene expression. Thus, by appropriate choice of the regulatory domain fused to the ZFP, one can selectively modulate the expression of PLN, and hence control various physiological processes correlated with contractility and calcium compartmentalization.

By engineering ZFPs that bind to (and modulate expression of) PLN to varying degrees, the extent to which a physiological process (e.g., contractility) is modulated can be varied, thereby enabling treatment to be tailored. This can be achieved because multiple target sites (e.g., 9, 12 or 18 base pair target sites) in the PLN gene, or indeed in any gene involved in contractility or calcium compartmentalization, can be acted upon by the ZFPs provided herein. Thus, in some methods, a plurality of ZFPs (or fusions comprising these ZFPs) is administered. These ZFPs can then bind to different target sites located in or around the PLN gene. Such ZFPs can in some instances have a synergistic effect. In certain methods, the plurality of fusion proteins includes different regulatory domains.

Also provided herein are polynucleotides and nucleic acids that encode the ZFPs disclosed herein. Additionally, pharmaceutical compositions containing the nucleic acids and/or ZFPs are also provided. For example, certain compositions include a nucleic acid that encodes one of the ZFPs described herein operably linked to a regulatory sequence, in combination with a pharmaceutically acceptable carrier or diluent, wherein the regulatory sequence allows for expression of the nucleic acid in a cell. Protein-based compositions include a ZFP as disclosed herein and a pharmaceutically acceptable carrier or diluent.

These and other embodiments will readily occur to those of ordinary skill in the art in view of the disclosure herein.

BRIEF DESCRIPTION OF THE DRAWINGS

FIG. 1, panels A and B, show the amino acid sequences of fusion proteins comprising exemplary ZFPs as described herein that repress expression of PLN. FIG. 1A shows the amino acid sequence of a fusion protein comprising the ZFP designated SBS-6439 (SEQ ID NO:68). FIG. 1B shows the amino acid sequence of a fusion protein comprising the ZFP designated SBS-6576 (SEQ ID NO:69).

FIG. 2, panels A-C, are graphs depicting repression of phospholamban (PLN) expression in rat cells transfected with plasmid or AAV vectors containing a PLN-targeted ZFP.

FIG. 3, panels A-D, are graphs depicting repression of phospholamban (PLN) expression in human cells transfected with plasmids containing a PLN-targeted ZFP. FIG. 3A depicts repression of PLN expression in UtSMC cells by 6576-KOX as compared to an empty plasmid control. FIG. 3B depicts repression of PLN expression in JRH30 cells by 6576-KOX as compared to an empty plasmid control. FIG. 3C depicts repression of PLN expression in UtSMC cells by 6576-KOX and 6624-KOX as compared to an empty plasmid control. FIG. 3D depicts repression of PLN expression in SJRH30 cells by 6576-KOX and 6624-KOX as compared to an empty plasmid control.

FIG. 5, panels A and B, depict PLN repression in rat cardiomyocytes using PLN-targeted ZFPs.

DETAILED DESCRIPTION

Figure 2A:
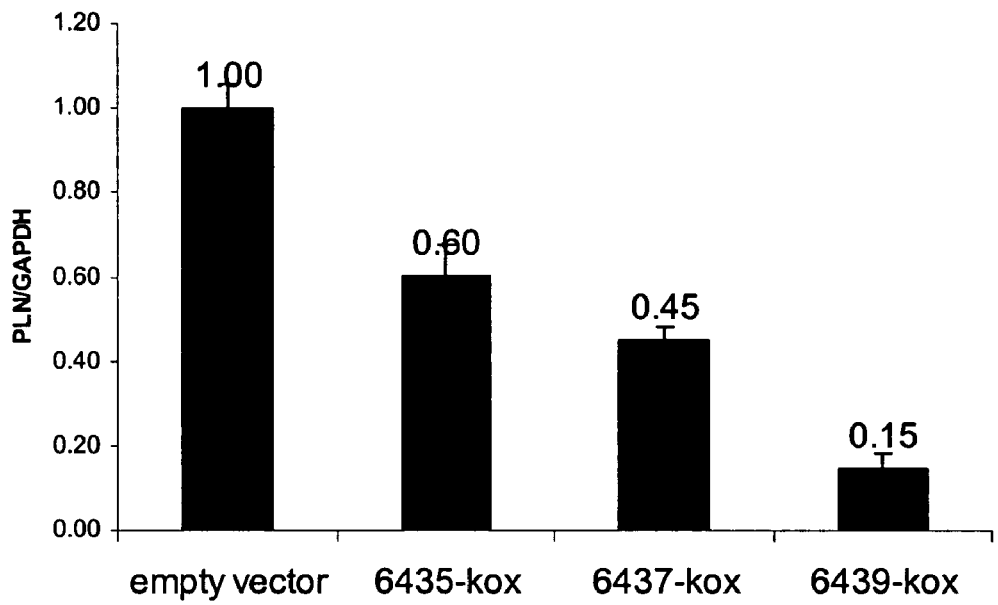
FIG. 2A shows repression of PLN by plasmids encoding fusion proteins comprising a KOX repression domain and PLN-targeted ZFP (SBS-6435, SBS-6437 or SBS-6439). The fusion proteins are designated 6435-KOX, SBS-6437-KOX or 6439-KOX.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

I. Definitions

The term "zinc finger protein" or "ZFP" refers to a protein having DNA binding domains that are stabilized by zinc. The individual DNA binding domains are typically referred to as "fingers." A ZFP has least one finger, typically two, three, four, five, six or more fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins (C2H2 class) is -Cys-(X)2-4-Cys-(X)12-His-(X)3-5-His (where X is any amino acid) (SEQ ID NO:1). Additional classes of zinc finger proteins are known and are useful in the practice of the methods, and in the manufacture and use of the compositions disclosed herein (see, e.g., Rhodes et al. (1993) Scientific American 268:56-65 and US Patent Application Publication No. 2003/0108880). Studies have demonstrated that a single zinc finger of this class consists of an alpha helix containing the two invariant histidine residues coordinated with zinc along with the two cysteine residues of a single beta turn (see, e.g., Berg & Shi, Science 271:1081-1085 (1996)).

A "target site" is the nucleic acid sequence recognized by a ZFP. A single target site typically has about four to about ten base pairs. Typically, a two-fingered ZFP recognizes a four to seven base pair target site, a three-fingered ZFP recognizes a six to ten base pair target site, a four-finger ZFP recognizes a 12-14 bp target sequence and a six-fingered ZFP recognizes an 18-20 bp target sequence, which can comprise two adjacent nine to ten base pair target sites or three adjacent 6-7 bp target sites.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (i.e., a "D-able subsite," see co-owned WO 00/42219) a subsite is four nucleotides in length and overlaps with another 3- or 4-nucleotide subsite.

"Kd" refers to the dissociation constant for a binding molecule, i.e., the concentration of a compound (e.g., a zinc finger protein) that gives half maximal binding of the compound to its target (i.e., half of the compound molecules are bound to the target) under given conditions (i.e., when [target]<<Kd), as measured using a given assay system (see, e.g., U.S. Pat. No. 5,789,538). The assay system used to measure the Kd should be chosen so that it gives the most accurate measure of the actual Kd of the ZFP. Any assay system can be used, as long is it gives an accurate measurement of the actual Kd of the ZFP. In one embodiment, the Kd for a ZFP is measured using an electrophoretic mobility shift assay ("EMSA"). Unless an adjustment is made for ZFP purity or activity, the Kd calculations may result in an overestimate of the true Kd of a given ZFP. Preferably, the Kd of a ZFP used to modulate transcription of a gene is less than about 100 nM, more preferably less than about 75 nM, more preferably less than about 50 nM, most preferably less than about 25 nM.

A "gene," for the purposes of the present disclosure, includes a DNA region encoding a gene product, as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Phospholamban (PLN) sequences from various species have been described and published. For example, promoter proximal regions of the human PLN (GenBank Accession No. AF177763), rat PLN (GenBank Accession No. AH002227), chicken PLN (GenBank Accession No. AH003051), pig PLN (GenBank Accession No. X15075), rabbit PLN (GenBank Accession No. AH001235), mouse PLN (GenBank Accession No. NM_023129) and dog PLN (AF037348) genes are available.

Furthermore, the term "gene" includes nucleic acids that are substantially identical to a native gene. The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987-1999, including supplements such as supplement 46 (April 1999)]. Use of these programs to conduct sequence comparisons are typically conducted using the default parameters specific for each program.

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. This is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For determining sequence similarity the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)). 11171 In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Hybridizes substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein that encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid that encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. See, e.g., Creighton (1984) Proteins, W. H. Freeman and Company. In addition, individual substitutions, deletions or additions which alter, add or delete a single amino acid or a small percentage of amino acids in an encoded sequence are also "conservatively modified variations."

A "functional fragment" or "functional equivalent" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid, binding to a regulatory molecule) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340: 245-246; U.S. Pat. No. 5,585,245 and PCT WO 98/44350.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. Thus, the term polynucleotide sequence is the alphabetical representation of a polynucleotide molecule. This alphabetical representation can be input into databases in a computer having a central processing unit and used for bioinformatics applications such as functional genomics and homology searching. The terms additionally encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). The nucleotide sequences are displayed herein in the conventional 5'-3' orientation.

"Chromatin" is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone HI is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. An exogenous molecule can comprise, for example, a functioning version of a malfunctioning endogenous molecule or a malfunctioning version of a normally functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions.

An "endogenous gene" is a gene that is present in its normal genomic and chromatin context. An endogenous gene can be present, e.g., in a chromosome, an episome, a bacterial genome or a viral genome.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

A "fusion molecule" is a molecule in which two or more subunit molecules are linked, typically covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" refers to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, in some instances an increase in production of a gene product by about 2-fold, in other instances from about 2- to about 5-fold or any integer therebetween, in still other instances between about 5- and about 10-fold or any integer therebetween, in yet other instances between about 10- and about 20-fold or any integer therebetween, sometimes between about 20- and about 50-fold or any integer therebetween, in other instances between about 50- and about 100-fold or any integer therebetween, and in yet other instances between 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, in some instances a decrease in production of a gene product by about 2-fold, in other instances from about 2- to about 5-fold or any integer therebetween, in yet other instances between about 5- and about 10-fold or any integer therebetween, in still other instances between about 10- and about 20-fold or any integer therebetween, sometimes between about 20- and about 50-fold or any integer therebetween, in other instances between about 50- and about 100-fold or any integer therebetween, in still other instances 100-fold or more. In yet other instances, gene repression results in complete inhibition of gene expression, such that no gene product is detectable.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene (e.g. PLN). Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and Ca2+), cell growth, and vascularization. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" or "functional domain" refers to a protein or a protein domain that has transcriptional modulation activity when tethered to a DNA binding domain, i.e., a ZFP. Typically, a regulatory domain is covalently or noncovalently linked to a ZFP (e.g., to form a fusion molecule) to effect transcription modulation. Regulatory domains can be activation domains or repression domains. Activation domains include, but are not limited to, VP16, VP64 and the p65 subunit of nuclear factor Kappa-B. Repression domains include, but are not limited to, KOX, KRAB MBD2B and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498-502 (1998)). Alternatively, a ZFP can act alone, without a regulatory domain, to effect transcription modulation.

The term "operably linked" or "operatively linked" is used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively linked to a coding sequence, even though they are not contiguous.

With respect to fusion polypeptides, the term "operably linked" or "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette," "expression cassette" or "expression construct" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV") thymidine kinase ("tk") promoter or a mutated HSV tk promoter, as described in Eisenberg & McKnight, Mol. Cell. Biol. 5:1940-1947 (1985).

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains an expression vector or nucleic acid, either of which optionally encodes a ZFP or a ZFP fusion protein. The host cell typically supports the replication or expression of the expression vector. Host cells can be prokaryotic cells such as, for example, $E.\ coli$, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

The term "naturally occurring," as applied to an object, means that the object can be found in nature, as distinct from being artificially produced by humans.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

By an "effective" amount (or "therapeutically effective" amount) of a pharmaceutical composition is meant a sufficient, but nontoxic amount of the agent to provide the desired effect. The term refers to an amount sufficient to treat a subject. Thus, the term therapeutic amount refers to an amount sufficient to remedy a disease state or symptoms, by preventing, hindering, retarding or reversing the progression of the disease or any other undesirable symptoms whatsoever. The term prophylactically effective amount refers to an amount given to a subject that does not yet have the disease, and thus is an amount effective to prevent, hinder or retard the onset of a disease.

II. Overview

A variety of compositions and methods are provided herein for modulating PLN expression, thereby treating various heart conditions. For example, zinc finger proteins that are capable of modulating PLN expression are provided. Also described are methods for modulating cardiac contractility by contacting a cell or population of cells such as in an organism, with one or more zinc finger proteins (ZFPs) that bind to specific sequences associated with the PLN gene. In certain methods, one ZFP is administered and is able to bind to a target site in the PLN gene. Other methods involve administering a plurality of different ZFPs that bind to multiple target sites in the PLN gene.

Thus, also provided herein are a variety of zinc finger proteins that are engineered to specifically recognize and bind to particular nucleic acid segments (target sites) in the PLN gene, modulate PLN expression and thereby modulate cardiac contractility and treat heart disease. In one embodiment, the ZFPs are linked to regulatory domains to create chimeric transcription factors to activate or repress transcription of the PLN gene.

With such ZFPs, expression of PLN can be enhanced; with certain other ZFPs, expression can be repressed. The target site can be adjacent to, upstream of, and/or downstream of the transcription start site (defined as nucleotide +1). As indicated above, one or more ZFPs can be used to modulate PLN expression. Thus, depending upon the particular ZFP(s) utilized, one can tailor the level at which the PLN gene is expressed.

By virtue of the ability of the ZFPs to bind to target sites and influence expression of PLN, the ZFPs provided herein can be used to treat a wide range of heart conditions. For example, repression of PLN expression can be achieved using the ZFPs described herein, thereby increasing contractility (e.g., by increasing SERCA2a:PLN ratio). Thus, in certain applications, the ZFPs can be used to repress expression of PLN, both in vitro and in vivo. Such repression can be utilized for example to alter the contractile activity of cardiac muscle and, accordingly, as treatment for congestive heart failure.

Other methods involve activation of PLN to reduce contractility, for example, in the treatment of tachycardia and arrhythmias.

In addition, inactivation of the phospholamban gene can be used for treatment of congestive heart failure and/or to stimulate cardiac contractility. In these embodiments, fusion proteins comprising an engineered zinc finger domain and a cleavage domain (or cleavage half-domain) are used for targeted cleavage of a DNA sequence in the endogenous phospholamban gene. Targeted cleavage can result in the subsequent introduction of a mutation into the cleaved gene by non-homologous end-joining; alternatively, one or more sequences can be inserted into a gene by homologous recombination following targeted cleavage. See U.S. Patent Application Publication Nos. 2003/0232410; 2005/0026157; 2005/0064474 and WO 03/87341 for additional details relating to targeted cleavage and recombination.

III. Zinc Finger Proteins for Regulating Phospholamban Gene Expression

A. General

The zinc finger proteins (ZFPs) disclosed herein are proteins that can bind to DNA in a sequence-specific manner. As indicated above, these ZFPs can be used to modulated PLN expression in vivo or in vitro and by so doing treat various heart conditions. An exemplary motif characterizing one class of these proteins, the $C_2H_2$ class, is -Cys-$(X)_{2-4}$-Cys-$(X)_{12}$-His-$(X)_{3-5}$-His (where X is any amino acid) (SEQ. ID. NO:1). Several structural studies have demonstrated that the finger domain contains an alpha helix containing the two invariant histidine residues and two invariant cysteine residues in a beta turn coordinated through zinc. However, the ZFPs provided herein are not limited to this particular class. Additional classes of zinc finger proteins are known and can also be used in the methods and compositions disclosed herein (see, e.g., Rhodes, et al. (1993) Scientific American 268:56-65 and US Patent Application Publication No. 2003/0108880). In certain ZFPs, a single finger domain is about 30 amino acids in length. Zinc finger domains are involved not only in DNA-recognition, but also in RNA binding and in protein-protein binding.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1, 2, 3 and 6 on each recognition helix making contacts with their respective DNA triplet subsites. The amino terminus of Zif268 is situated at the 3' end of the DNA strand with which it makes most contacts. Some zinc fingers can bind to a fourth base in a target segment. If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

B. Exemplary ZFPs

ZFPs that bind to particular target sites in the PLN gene are disclosed herein. The target sites can be located upstream or downstream of the transcription initiation site (defined as nucleotide +1) Target sites can include, for example, 9 nucleotides, 12 nucleotides or 18 nucleotides.

The target sites can be located adjacent the transcription initiation site or be located significantly upstream or downstream of the transcription start site. In certain embodiments, a single target site is recognized by the ZFP(s). In other instances, multiple ZFPs can be used, each recognizing different targets in a PLN gene.

The ZFPs that bind to these target sites typically include at least one zinc finger but can include a plurality of zinc fingers (e.g., 2, 3, 4, 5, 6 or more fingers). Usually, the ZFPs include at least three fingers. Certain of the ZFPs include four or six fingers. The ZFPs that include three fingers typically recognize a target site that includes 9 or 10 nucleotides; four-finger ZFPs recognize a 12-14-nucleotide target site, and ZFPs having six fingers can recognize target sites that include 18 to 21 nucleotides. The ZFPs can also be fusion proteins that include one or more regulatory domains, which domains can be transcriptional activation or repression domains.

Exemplary zinc finger proteins that bind to a target site in a PLN gene are described in detail in Example 1 and Tables 1, 2 and 3. Table 1 shows the nucleotide sequence of the target site for each zinc finger protein and the location of the target site relative to the transcription start site. Lower-case letters represent nucleotides not directly contacted by the constituent zinc fingers of the protein. See, e.g., WO 01/53480 and US 2003-0119023. Negative numbers refer to bp upstream of the transcription start site and positive numbers refer to bp downstream of the transcription start site, where the transcription start site is defined as nucleotide +1. The PLN sequences examined for target sites include the sequences from rat (GenBank Accession No. NW_043442) and human (GenBank Accession No. NT_033944) PLN genes.

TABLE 1

| ZFP Name | Target site (5'-3') | SEQ ID | Location of Target Site |
|---|---|---|---|
| SBS-6439 | GACATGGCCATGGATAGC | 15 | −2332 (rat) |
| SBS-6576 | GATTGGTACAAGaGTGGGG | 16 | −2090 (human) |
| SBS-6577 | AGATTGgTACAAGaGTGGGG | 74 | −2090 (human) |
| SBS-6578 | GATTGGTACAAGaGTGGGG | 75 | −2090 (human) |
| SBS-6435 | TCACTGGAGGCGGCTTTGG | 17 | −2172 (rat) |

TABLE 1-continued

| ZFP Name | Target site (5'-3') | SEQ ID | Location of Target Site |
|---|---|---|---|
| SBS-6437 | TTCAAGGATCTGAGCTGCG | 18 | −2351 (rat) |
| SBS-6624 | AGACAGGATTCAaATCCAG | 19 | −1650 (human) |
| SBS-1563 | GAGGCGGCG | 70 | −250 (human) |

Table 2 shows the amino acid sequences included in the recognition region of each finger (F1 through F6) of the various zinc finger proteins designed to bind to a target sequence in the rat PLN gene. The amino acid sequences shown depict residues −1 through +6, as numbered relative to the first amino acid residue in the alpha-helical portion of the zinc finger. The target subsite recognized by the amino acid sequence is shown in parentheses.

TABLE 2

| | SBS-6439 | Seq Id | SBS-6435 | Seq Id | SBS-6437 | Seq Id |
|---|---|---|---|---|---|---|
| F1 | TSADLTE (AGC) | 20 | RSDSLST (TGG) | 26 | RSDTLST (GCG) | 32 |
| F2 | ASANLSR (GAT) | 21 | ASANLSR (CTT) | 27 | RSDADRKR (GCT) | 33 |
| F3 | RSDALST (ATG) | 22 | RSDDLSR (GCG) | 28 | RSKTLSE (CTG) | 34 |
| F4 | DRSTRTK (GCC) | 23 | RNDNRTK (GAG) | 29 | ANSNRIK (GAT) | 35 |
| F5 | RSDVLSA (ATG) | 24 | RSDALSE (CTG) | 30 | RSDNLST (AAG) | 36 |
| F6 | DRSNRIK (GAC) | 25 | RSSDRTK (TCA) | 31 | DSSSRIK (TTC) | 37 |

Table 3 shows the amino acid sequences included in the recognition region of each finger (F1 through F6) of the various zinc finger proteins designed to bind to a target sequence in the human PLN gene. The amino acid sequences shown depict residues −1 through +6, as numbered relative to the first amino acid residue in the alpha-helical portion of the zinc finger. The target subsite recognized by the amino acid sequence is shown in parentheses.

TABLE 3

| | SBS-6576 | Seq ID | SBS-6624 | Seq ID | SBS-1563 | Seq ID | SBS-6577 | Seq ID | SBS-6578 | Seq ID |
|---|---|---|---|---|---|---|---|---|---|---|
| F1 | RSDHLSQ (GGG) | 38 | RSDNLSE (GAG) | 44 | RSDELTR (GCG) | 71 | RSDHLSQ (GGG) | 76 | RSDHLSQ (GGG) | 82 |
| F2 | RSDVRKN (GTG) | 39 | HSRSRKT (ATG) | 45 | RSDELQR (GCG) | 72 | RSDVRKN (GTG) | 77 | RSDVRKN (GTG) | 83 |
| F3 | RSDALSV (AAG) | 40 | DSESLNA (TCA) | 46 | RSDNLTR (GAG) | 73 | RSDALSV (AAG) | 78 | RSDALSV (AAG) | 84 |
| F4 | DNANRTK (TAG) | 41 | TSSNLSR (GAT) | 47 | | | DNANRTK (TAG) | 79 | DNANRTK (TAG) | 85 |
| F5 | RSDHLST (TGG) | 42 | RSDNLSQ (GAG) | 48 | | | RSDALST (TTG) | 80 | TKLHLIE (TGG) | 86 |
| F6 | TSSNRTK (GAT) | 43 | QRQHRKT (AGA) | 49 | | | QNSHRKT (AGA) | 81 | QSANLSR (GAT) | 87 |

As noted above, the target sites may be any length, but are preferably 9-10 nucleotides or 18-21 nucleotides in length. For the exemplary ZFPs described above, their selected target sites have been shown to exhibit enhanced sequence conservation as well as enhanced DNase I accessibility in both H9c2(2-1) cells and rat primary cardiac myocytes.

Thus, as indicated herein, one or more of the ZFPs described herein can be utilized to modulate cardiac contractility (and by so doing treat heart and other contractile diseases), by modulating the activity of PLN. By judicious selection of various ZFPs and/or combinations thereof, one can tailor PLN modulation and, accordingly, modulate contractility.

IV. Characteristics of ZFPs

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand. In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. For example, if a zinc finger protein comprises from N-terminal to C-terminal first, second and third fingers that individually bind, respectively, to triplets 5'GAC3', 5'GTA3' and 5'GGC3' then the zinc finger protein binds to the target segment 3'CAGATGCGG5' (SEQ ID NO:2). If the zinc finger protein comprises the fingers in another order, for example, second finger, first finger, third finger, then the zinc finger protein binds to a target segment comprising a different permutation of triplets, in this example, 3'ATGCAGCGG5' (SEQ ID NO:3). See Berg & Shi, Science 271, 1081-1086 (1996). The assessment of binding properties of a zinc finger protein as the aggregate of its component fingers may, in some cases, be influenced by context-dependent interactions of multiple fingers binding in the same protein.

Two or more zinc finger proteins can be linked to have a target specificity that is the aggregate of that of the component zinc finger proteins (see e.g., Kim & Pabo, Proc. Natl. Acad. Sci. U.S.A. 95, 2812-2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZ-Z_AAABBBCCC5', where the underline indicates a short intervening region (typically 0-5 bases of any type). In this situation, the target site can be viewed as comprising two target segments separated by an intervening segment.

Linkage can be accomplished using any of the following peptide linkers:

```
    T G E K P:                            (SEQ ID NO: 4)
(Liu et al., 1997, supra.);

(G4S)n                                    (SEQ ID NO: 5)

(Kim et al., Proc. Natl. Acad. Sci.
U.S.A. 93: 1156-1160 (1996.);

GGRRGGGS;                                 (SEQ ID NO: 6)

LRQRDGERP;                                (SEQ ID NO: 7)

LRQKDGGGSERP;                             (SEQ ID NO: 8)

LRQKD(G3S)2ERP.                           (SEQ ID NO: 9)
```

Alternatively, flexible linkers can be rationally designed using computer programs capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

Linkage of two zinc finger proteins is advantageous for conferring a unique binding specificity within a mammalian genome. A typical mammalian diploid genome consists of $3 \times 10^9$ bp. Assuming that the four nucleotides A, C, G, and T are randomly distributed, a given 9 bp sequence is present approximately 23,000 times. Thus a ZFP recognizing a 9 bp target with absolute specificity would have the potential to bind to about 23,000 sites within the genome. An 18 bp sequence is present about once in a random DNA sequence whose complexity is ten times that of a mammalian genome.

A component finger of zinc finger protein typically contains about 30 amino acids and, in one embodiment, has the following motif (N-C):

```
                                          (SEQ ID NO: 88)
Cys-(X)2-4-Cys-X.X.X.X.X.X.X.X.X.X.X-His-(X)3-5-
His
```

The two invariant histidine residues and two invariant cysteine residues in a single beta turn are coordinated through zinc atom (see, e.g., Berg & Shi, Science 271, 1081-1085 (1996)). The above motif shows a numbering convention that is standard in the field for the region of a zinc finger conferring binding specificity. The amino acid on the left (N-terminal side) of the first invariant His residue is assigned the number +6, and other amino acids further to the left are assigned successively decreasing numbers. The alpha helix begins at residue 1 and extends to the residue following the second conserved histidine. The entire helix is therefore of variable length, between 11 and 13 residues.

V. Design of ZFPs

The ZFPs provided herein are engineered to recognize a selected target site in a PLN gene. Non-limiting examples of ZFPs suitable for modulating PLN expression are described herein.

The process of designing or selecting a ZFP typically starts with a natural ZFP as a source of framework residues. The process of design or selection serves to define nonconserved positions (i.e., positions −1 to +6) so as to confer a desired binding specificity. One suitable ZFP is the DNA binding domain of the mouse transcription factor Zif268. The DNA binding domain of this protein has the amino acid sequence:

```
YACPVESCDRRFSRSDELTRHIRIHTGQKP    (SEQ ID NO: 10)
(F1)

FQCRICMRNFSRSDHLTTHIRTHTGEKP      (SEQ ID NO: 11)
(F2)

FACDICGRKFARSDERKRHTKIHLRQK       SEQ ID NO: 12)
(F3)

and binds to a target 5'          (SEQ ID NO: 13)
GCG TGG GCG 3'.
```

Another suitable natural zinc finger protein as a source of framework residues is Sp-1. The Sp-1 sequence used for construction of zinc finger proteins corresponds to amino acids 531 to 624 in the Sp-1 transcription factor. This sequence is 94 amino acids in length. See, e.g., U.S. Patent Application No. 20030021776 for the sequence of Sp1 and an alternate form of Sp-1, referred to as an Sp-1 consensus sequence.

```
    Sp-1 binds to a target site   (SEQ ID NO: 14)
    5'GGG GCG GGG3'.
```

There are a number of substitution rules that assist rational design of some zinc finger proteins. For example, ZFP DNA-binding domains can be designed and/or selected to recognize a particular target site as described in co-owned WO 00/42219; WO 00/41566; and U.S. Ser. No. 09/444,241 filed Nov. 19, 1999; Ser. No. 09/535,088 filed Mar. 23, 2000; as well as U.S. Pat. Nos. 5,789,538; 6,007,408; 6,013,453; 6,140,081; and 6,140,466; and PCT publications WO 95/19431, WO 98/54311, WO 00/23464 and WO 00/27878. In one embodiment, a target site for a zinc finger DNA-binding domain is identified according to site selection rules disclosed in co-owned WO 00/42219. In a preferred embodiment, a ZFP is selected as described in co-owned WO 02/077227; See also WO 96/06166; Desjarlais & Berg, PNAS 90, 2256-2260 (1993); Choo & Klug, PNAS 91, 11163-11167 (1994); Desjarlais & Berg, PNAS 89, 7345-7349 (1992); Jamieson et al., Biochemistry 33:5689-5695 (1994); and Choo et al., WO 98/53057, WO 98/53058; WO 98/53059; WO 98/53060.

Many of these rules are supported by site-directed mutagenesis of the three-finger domain of the ubiquitous transcription factor, Sp-1 (Desjarlais and Berg, 1992; 1993). One of these rules is that a 5' G in a DNA triplet can be bound by a zinc finger incorporating arginine at position 6 of the recognition helix. Another substitution rule is that a G in the middle of a subsite can be recognized by including a histidine residue at position 3 of a zinc finger. A further substitution rule is that asparagine can be incorporated to recognize A in the middle of a triplet, aspartic acid, glutamic acid, serine or threonine can be incorporated to recognize C in the middle of a triplet, and amino acids with small side chains such as alanine can be incorporated to recognize T in the middle of a triplet. A further substitution rule is that the 3' base of a triplet subsite can be recognized by incorporating the following amino acids at position −1 of the recognition helix: arginine to recognize G, glutamine to recognize A, glutamic acid (or aspartic acid) to recognize C, and threonine to recognize T. Although these substitution rules are useful in designing zinc finger proteins they do not take into account all possible target sites. Furthermore, the assumption underlying the rules, namely that a particular amino acid in a zinc finger is responsible for binding to a particular base in a subsite is only approximate. Context-dependent interactions between proximate amino acids in a finger or binding of multiple amino acids to a single base or vice versa can cause variation of the binding specificities predicted by the existing substitution rules. Accordingly, in certain embodiments, a ZFP DNA-binding domain of predetermined specificity is obtained according to the methods described in co-owned WO 02/077227.

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., PNAS 92:344-348 (1995); Jamieson et al., Biochemistry 33:5689-5695 (1994); Rebar & Pabo, Science 263:671-673 (1994); Choo & Klug, PNAS 91:11163-11167 (1994); Choo & Klug, PNAS 91: 11168-11172 (1994); Desjarlais & Berg, PNAS 90:2256-2260 (1993); Desjarlais & Berg, PNAS 89:7345-7349 (1992); Pomerantz et al., Science 267:93-96 (1995); Pomerantz et al., PNAS 92:9752-9756 (1995); and Liu et al., PNAS 94:5525-5530 (1997); Griesman & Pabo, Science 275: 657-661 (1997); Desjarlais & Berg, PNAS 91:11-99-11103 (1994)).

In certain preferred embodiments, the binding specificity of a DNA-binding domain (e.g., a ZFP DNA-binding domain) is determined by identifying accessible regions in the sequence in question (e.g., in cellular chromatin). Accessible regions can be determined as described in co-owned WO 01/83732. See, also, U.S. Patent Application No. 20030021776A1. A DNA-binding domain is then designed and/or selected as described herein to bind to a target site within the accessible region.

VI. Exemplary Zinc Finger Proteins and Equivalents

Disclosed herein are compositions and methods for regulation of transcription and/or for targeted DNA cleavage which are useful, for example, in the treatment of congestive heart failure and other deficiencies of cardiac contractility. These include fusion proteins comprising an engineered zinc finger protein and a functional domain such as, for example, a transcriptional repression domain, a transcriptional activation domain, a nuclease domain or a nuclease half-domain. Suitable functional domains are known in the art and include, without limitation, transcriptional activation domains such as, for example, VP16, VP64 and p65; transcriptional repression domains such as, for example, KOX and v-erbA, cleavage domains such as, for example, HO and cleavage half-domains such as, for example, the cleavage domain of FokI. One or more of the same or different functional domains can be present in a given fusion protein. See co-owned U.S. Patent Application Publication No. 2002/0160940, incorporated by reference, for disclosure of exemplary transcriptional activation and repression domains. Co-owned U.S. Patent Application Publication No. 2005/0064474, incorporated by reference, discloses exemplary cleavage domains and cleavage half-domains.

In certain embodiments, a zinc finger protein is engineered to bind to a sequence comprising the target sequence GAT-TGGTACAAGaGTGGGG (SEQ ID NO:16), present upstream of the human phospholamban gene (Table 1).

An exemplary six-finger zinc finger protein, SBS-6576, that has been engineered to bind to SEQ ID NO:16 has the amino acid sequence:

MAPKKKRKVGIHGVPAAMAERPFQCRICMRNFS<u>RSDHLSQ</u>HIRTHTGEKPFACD (SEQ ID NO: 69)

ICGKKFA<u>RSDVRKN</u>HTKIHTGGGGSQRPFQCRICMRNFS<u>RSDALSV</u>HIRTHTGEKPFAC

DICGRKFA<u>DNANRT</u>KHTKIHTGSQKPFQCRICMRNFS<u>RSDHLST</u>HIRTHTGEKPFACDI

CGRKFA<u>TSSNRT</u>KHTKIHLRQKDAARGSGMDAKSLTAWSRTLVTFKDVFVDFTREEWKL

LDTAQQIVYRNVMLENYKNLVSLGYQLTKPDVILRLEKGEEPWLVEREIHQETHPDSET

AFEIKSSVDYKDDDDK.

The underlined amino acid residues in SEQ ID NO:69 correspond to residues −1 through +6 with respect to the start of the helical portion of a zinc finger and are denoted the "recognition regions" because one or more of these residues participate in sequence specificity of nucleic acid binding. Accordingly, proteins comprising the same three recognition regions in a different polypeptide backbone sequence are considered equivalents to the protein identified as SEQ ID NO:69, since they will have the same DNA-binding specificity.

Thus, in certain embodiments, the six recognition regions (underlined in SEQ ID NO:69 above) can be placed in any zinc finger backbone (see, e.g., U.S. Pat. Nos. 6,453,242 and 6,534,261) and the resulting protein can be used to regulate transcription, e.g., to modulate cardiac contractility in the treatment of congestive heart failure and other cardiac disorders. Accordingly, engineered zinc finger proteins comprising the following sequence can be used in the disclosed methods:

$C-X_{2-4}-C-X_5-R-S-D-H-L-S-Q-$
$H-X_{3-5}-H-X_7-C-X_{2-4}-C-X_5-R-S-D-V-R-$
$K-N-H-X_{3-5}-H-X_7-C-X_{2-4}-C-X_5-R-S-D-$
$A-L-S-V-H-X_{3-5}-H-X_7-C-X_{2-4}-C-X_5-$
$D-N-A-N-R-T-K-H-X_{3-5}-H-X_7-C-X_{2-4}-$
$C-X_5-R-S-D-H-L-S-T-H-X_{3-5}-H-X_7-C-$
$X_{2-4}-C-X_5-T-S-S-N-R-T-K-H.$  (SEQ ID NO: 89)

Within the recognition region, residues −1, +3 and +6 are primarily responsible for protein-nucleotide contacts. Accordingly, non-limiting examples of additional equivalents include proteins comprising six zinc fingers wherein the first finger contains a R residue at −1, a H residue at +3 and a Q residue at +6 (RXXHXXQ, SEQ ID NO:90); the second finger contains a R residue at −1, a V residue at +3 and a N residue at +6 (RXXVXXN, SEQ ID NO:91); the third finger contains a R residue at −1, an A residue at +3 and a V residue at +6 (RXXAXXV, SEQ ID NO:92); the fourth finger contains a D residue at −1, a N residue at +3 and a K residue at +6 (DXXNXXK, SEQ ID NO:93); the fifth finger contains a R residue at −1, a H residue at +3 and a T residue at +6 (RXXHXXT, SEQ ID NO:94); and the sixth finger contains a T residue at −1, a N residue at +3 and a K residue at +6 (TXXNXXK, SEQ ID NO:95). Thus, for example, proteins comprising SEQ ID NO:96 are considered equivalents for use in the disclosed methods.

$C-X_{2-4}-C-X_5-R-X-X-H-X-X-Q-$
$H-X_{3-5}-H-X_7-C-X_{2-4}-C-X_5-R-X-X-V-X-$
$X-N-H-X_{3-5}-H-X_7-C-X_{2-4}-C-X_5-R-X-X-$
$A-X-X-V-H-X_{3-5}-H-X_7-C-X_{2-4}-C-X_5-D-$
$X-X-N-X-X-K-H-X_{3-5}-H-X_7-C-X_{2-4}-C-$
$X_5-R-X-X-H-X-X-T-H-X_{3-5}-H-X_7-C-$
$X_{2-4}-C-X_5-T-X-X-N-X-X-K-H-X_{3-5}-H$  (SEQ ID NO: 96)

Additional equivalents comprise any ZFP that binds to a sequence comprising the target sequence GATTGGTACAA-GaGTGGGG (SEQ ID NO:16).

Correspondences between amino acids at the −1, +3 and +6 contact residues of the recognition region of a zinc finger, and nucleotides in a target site, have been described. See, for example, U.S. Pat. Nos. 6,007,988; 6,013,453; 6,746,838 and 6,866,997; as well as PCT Publications WO 96/06166; WO 98/53058; WO 98/53059 and WO 98/53060. Accordingly, also to be considered equivalents are six-finger zinc finger proteins in which the first finger contains R at −1; H at +3 and R, K, S or T at +6 (and if S or T, also contains D at position +2 of the adjacent C-terminal zinc finger); the second finger contains R at −1; A, S or V at +3 and R, K, S or T at +6 (and if S or T, also contains D at position +2 of the adjacent C-terminal zinc finger); the third finger contains R at −1; N at +3 and E, N, Q or V at +6 (and if Q, does not contain D at position +2 of the adjacent C-terminal zinc finger); the fourth finger contains D or H at −1; N at +3 and S, T, V or K at +6; the fifth finger contains R at −1; H at +3 and S, T, V or K at +6; and the sixth finger contains N, H, T or Q at −1; N at +3 and R, K, S or T at +6 (and if S or T, also contains D at position +2 of the adjacent C-terminal zinc finger).

In certain additional embodiments, a zinc finger protein is engineered to bind to a sequence comprising the target sequence AGACAGGATTCAaATCCAG (SEQ ID NO:19), present upstream of the human phospholamban gene (Table 1). An exemplary six-finger zinc finger protein, SBS-6624 (Table 3), has been engineered to bind to SEQ ID NO:19.

The amino acid residues shown in Table 3 for the 6624 zinc finger protein correspond to residues −1 through +6 with respect to the start of the helical portion of a zinc finger and are denoted the "recognition regions" because one or more of these residues participate in sequence specificity of nucleic acid binding. Accordingly, proteins comprising the same three recognition regions in a different polypeptide backbone sequence are considered equivalents to the SBS-6624 protein, since they will have the same DNA-binding specificity.

Thus, in certain embodiments, the six recognition regions of the SBS-6624 protein (Table 3) can be present in any zinc finger backbone (see, e.g., U.S. Pat. Nos. 6,453,242 and 6,534,261) and the resulting protein can be used to regulate transcription, e.g., for modulation of cardiac contractility. Accordingly, engineered zinc finger proteins comprising the following sequence can be used in the disclosed methods:

$C-X_{2-4}-C-X_5-R-S-D-N-L-S-E-H-$
$X_{3-5}-H-X_7-C-X_{2-4}-C-X_5-H-S-R-S-R-K-$
$T-H-X_{3-5}-H-X_7-C-X_{2-4}-X_5-D-S-E-S-L-$
$N-A-H-X_{3-5}-H-X_7-C-X_{2-4}-C-X_5-T-S-S-$
$N-L-S-R-H-X_{3-5}-H-X_7-C-X_{2-4}-C-X_5-R-$
$S-D-N-L-S-Q-H-X_{3-5}-H-X_7-C-X_{2-4}-C-$
$X_5-Q-R-Q-H-R-K-T-H.$  (SEQ ID NO: 97)

Within the recognition region, residues −1, +3 and +6 are primarily responsible for protein-nucleotide contacts. Accordingly, non-limiting examples of additional equivalents of SBS-6624 include proteins comprising six zinc fingers wherein the first finger contains a R residue at −1, a N residue at +3 and an E residue at +6 (RXXNXXE, SEQ ID NO:98); the second finger contains a H residue at −1, a S residue at +3 and a K residue at +6 (HXXSXXK, SEQ ID NO:99); the third finger contains a D residue at −1, a S residue at +3 and an A residue at +6 (DXXSXXA, SEQ ID NO:100); the fourth finger contains a T residue at −1, a N residue at +3 and a R residue at +6 (TXXNXXR, SEQ ID NO:101); the fifth finger contains a R residue at −1, a N residue at +3 and a Q residue at +6 (RXXNXXQ, SEQ ID NO:102); and the sixth finger contains a Q residue at −1, a H residue at +3 and a T residue at +6 (QXXHXXT, SEQ ID NO:103). Thus, for example, proteins comprising SEQ ID NO:104 are considered equivalents for use in the disclosed methods.

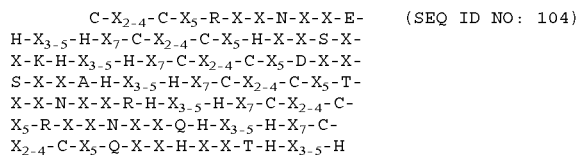
(SEQ ID NO: 104)

Additional equivalents of SBS-6624 comprise any ZFP that binds to a sequence comprising the target sequence AGA-CAGGATTCAaATCCAG (SEQ ID NO:19).

Correspondences between amino acids at the −1, +3 and +6 (and optionally +2) contact residues of the recognition region of a zinc finger, and nucleotides in a target site, have been described. See, for example, U.S. Pat. Nos. 6,007,988; 6,013,453; 6,746,838 and 6,866,997; as well as PCT Publications WO 96/06166; WO 98/53058; WO 98/53059 and WO 98/53060. Accordingly, also to be considered equivalents of SBS-6624 are six-finger zinc finger proteins in which the first finger contains R at −1; N at +3 and S, T, V, A, E or N at +6; the second finger contains D or H at −1; A, S or V at +3 and E, N V or Q at +6 (and if Q, does not contain D at position +2 of the adjacent C-terminal zinc finger); the third finger contains Q at −1; S, D, E, L, T, or V at +3 and S, T, V, or K at +6 (and if S or T, also contains D at position +2 of the adjacent C-terminal zinc finger); the fourth finger contains H, T, N or Q at −1; N at +3 and R, K, S or T at +6 (and if S or T, also contains D at position +2 of the adjacent C-terminal zinc finger); the fifth finger contains R at −1; N at +3 and S, T, V, A, E or N at +6; and the sixth finger contains Q at −1; H at +3 and E, N, V or Q at +6 (and if Q, does not contain D at position +2 of the adjacent C-terminal zinc finger).

VII. Production of Zinc Finger Proteins

A. Synthesis and Cloning

ZFP polypeptides and nucleic acids encoding the same can be made using routine techniques in the field of recombinant genetics. Basic texts disclosing general methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). In addition, nucleic acids less than about 100 bases can be custom ordered from any of a variety of commercial sources, such as The Midland Certified Reagent Company, The Great American Gene Company, ExpressGen Inc., Operon Technologies Inc. (Alameda, Calif.). Similarly, peptides can be custom ordered from any of a variety of sources, such as PeptidoGenic, HTI Bio-products, Inc., BMA Biomedicals Ltd (U.K.), Bio.Synthesis, Inc. Information regarding these commercial sources can be found on the internet.

Oligonucleotides can be chemically synthesized according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., Gene 16:21-26 (1981).

Two alternative methods are typically used to create the coding sequences required to express newly designed DNA-binding peptides. One protocol is a PCR-based assembly procedure that utilizes six overlapping oligonucleotides. Three oligonucleotides correspond to "universal" sequences that encode portions of the DNA-binding domain between the recognition helices. These oligonucleotides typically remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region that was previously filled in by polymerase in the above-mentioned protocol. Oligonucleotides complementary to oligos 1 and 6 are engineered to leave overhanging sequences specific for the restriction sites used in cloning into the vector of choice in the following step. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created using conventional site-directed mutagenesis methods.

Both assembly methods require that the resulting fragment encoding the newly designed ZFP be ligated into a vector.

Ultimately, the ZFP-encoding sequence is cloned into an expression vector. Expression vectors that are commonly utilized include, but are not limited to, a modified pMAL-c2 bacterial expression vector (New England BioLabs, Beverly, Mass.) or an eukaryotic expression vector, pcDNA (Promega, Madison, Wis.). The final constructs are verified by sequence analysis.

Any suitable method of protein purification known to those of skill in the art can be used to purify ZFPs (see, Ausubel, supra, Sambrook, supra). In addition, any suitable host can be used for expression, e.g., bacterial cells, insect cells, yeast cells, mammalian cells, and the like.

Expression of a zinc finger protein fused to a maltose binding protein (MBP-ZFP) in bacterial strain JM109 allows for straightforward purification through an amylose column (New England BioLabs, Beverly, Mass.). High expression levels of the zinc finger chimeric protein can be obtained by induction with IPTG since the MBP-ZFP fusion in the pMal-c2 expression plasmid is under the control of the tac promoter (New England BioLabs, Beverly, Mass.). Bacteria containing the MBP-ZFP fusion plasmids are inoculated into 2×YT medium containing 10 μM $ZnCl_2$, 0.02% glucose, plus 50 μg/ml ampicillin and shaken at 37° C. At mid-exponential growth IPTG is added to 0.3 mM and the cultures are allowed to shake. After 3 hours the bacteria are harvested by centrifugation, disrupted by sonication or by passage through a pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 .mu.M $ZnCl_2$, then eluted with maltose in essentially the same buffer (purification is based on a standard protocol from New England BioLabs. Purified proteins are quantitated and stored for biochemical analysis.

The dissociation constant of a purified protein, e.g., Kd, is typically characterized via electrophoretic mobility shift assays (EMSA) (Buratowski & Chodosh, in Current Protocols in Molecular Biology pp. 12.2.1-12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2.times.9 bp+intervening bases for a six finger ZFP. The annealed oligonucleotide targets possess a 1 base 5' overhang that allows for efficient labeling of the target with T4 phage polynucleotide kinase. For the assay the target is added at a concentration of 1 nM or lower (the actual concentration is kept at least 10-fold lower than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA.

The equilibrated reactions are loaded onto a 10% polyacrylamide gel, which has been pre-run for 45 min in Tris/glycine buffer, then bound and unbound labeled target is resolved by electrophoresis at 150V. Alternatively, 10-20% gradient Tris-HCl gels, containing a 4% polyacrylamide stacking gel, can be used. The dried gels are visualized by autoradiography or phosphorimaging and the apparent Kd is determined by calculating the protein concentration that yields half-maximal binding.

The assays can also include a determination of the active fraction in the protein preparations. Active fraction is determined by stoichiometric gel shifts in which protein is titrated against a high concentration of target DNA. Titrations are done at 100, 50, and 25% of target (usually at micromolar levels).

B. Phage Display

The technique of phage display provides a largely empirical means of generating zinc finger proteins with desired target specificity (see e.g., Rebar, U.S. Pat. No. 5,789,538; Choo et al., WO 96/06166; Barbas et al., WO 95/19431 and WO 98/543111; Jamieson et al., supra). The method can be used in conjunction with, or as an alternative to rational design. The method involves the generation of diverse libraries of mutagenized zinc finger proteins, followed by the isolation of proteins with desired DNA-binding properties using affinity selection methods. To use this method, the experimenter typically proceeds as follows. First, a gene for a zinc finger protein is mutagenized to introduce diversity into regions important for binding specificity and/or affinity. In a typical application, this is accomplished via randomization of a single finger at positions −1, +2, +3, and +6, and sometimes accessory positions such as +1, +5, +8 and +10. Next, the mutagenized gene is cloned into a phage or phagemid vector as a fusion with gene III of a filamentous phage, which encodes the coat protein pIII. The zinc finger gene is inserted between segments of gene III encoding the membrane export signal peptide and the remainder of pill, so that the zinc finger protein is expressed as an amino-terminal fusion with pIII or in the mature, processed protein.

When using phagemid vectors, the mutagenized zinc finger gene may also be fused to a truncated version of gene III encoding, minimally, the C-terminal region required for assembly of pIII into the phage particle. The resultant vector library is transformed into *E. coli* and used to produce filamentous phage that express variant zinc finger proteins on their surface as fusions with the coat protein pIII. If a phagemid vector is used, then this step requires superinfection with helper phage. The phage library is then incubated with a target DNA site, and affinity selection methods are used to isolate phage that bind target with high affinity from bulk phage. Typically, the DNA target is immobilized on a solid support, which is then washed under conditions sufficient to remove all but the tightest binding phage. After washing, any phage remaining on the support are recovered via elution under conditions which disrupt zinc finger—DNA binding. Recovered phage are used to infect fresh *E. coli*, which is then amplified and used to produce a new batch of phage particles. Selection and amplification are then repeated as many times as is necessary to enrich the phage pool for tight binders such that these may be identified using sequencing and/or screening methods. Although the method is illustrated for pIII fusions, analogous principles can be used to screen ZFP variants as pVIII fusions.

In certain embodiments, the sequence bound by a particular zinc finger protein is determined by conducting binding reactions (see, e.g., conditions for determination of Kd, supra) between the protein and a pool of randomized double-stranded oligonucleotide sequences. The binding reaction is analyzed by an electrophoretic mobility shift assay (EMSA), in which protein-DNA complexes undergo retarded migration in a gel and can be separated from unbound nucleic acid. Oligonucleotides that have bound the finger are purified from the gel and amplified, for example, by a polymerase chain reaction. The selection (i.e. binding reaction and EMSA analysis) is then repeated as many times as desired, with the selected oligonucleotide sequences. In this way, the binding specificity of a zinc finger protein having a particular amino acid sequence is determined.

C. Regulatory Domains

Zinc finger proteins are often expressed with an exogenous domain (or functional fragment thereof) as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is a KRAB repression domain from the human KOX-1 protein (Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Preferred domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

The identification of novel sequences and accessible regions (e.g., DNase I hypersensitive sites) in PLN genes allows for the design of fusion molecules for the treatment of heart conditions. Thus, in certain embodiments, the compositions and methods disclosed herein involve fusions between a DNA-binding domain specifically targeted to one or more regulatory regions of a PLN gene and a functional (e.g., repression or activation) domain (or a polynucleotide encoding such a fusion). In this way, the repression or activation domain is brought into proximity with a sequence in the gene that is bound by the DNA-binding domain. The transcriptional regulatory function of the functional domain is then able to act on the selected regulatory sequences.

In additional embodiments, targeted remodeling of chromatin, as disclosed in co-owned WO 01/83793 can be used to generate one or more sites in cellular chromatin that are accessible to the binding of a DNA binding molecule.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) Proc. Natl. Acad. Sci. USA 97:3930-3935.

FIG. 1 shows the amino acid sequences of fusion proteins comprising ZFPs as described herein that bind to a PLN gene and modulate PLN expression. Table 4 shows the locations of various functional domains within these fusion proteins, numbered by amino acid residue relative to the N-terminus of the amino acid sequences shown in FIG. 1. "NLS" refers to a nuclear localization signal derived for example from SV40 large T-antigen. A "Kox" domain refers to a regulatory domain that acts as a transcriptional repressor and is derived from KRAB-A/B boxes in human KOX1, as described above. "FLAG" is a synthetic epitope tag.

TABLE 4

|  | NLS | SBS-6439 | Kox | FLAG |
| --- | --- | --- | --- | --- |
| Fusion comprising SBS-6439 | 3-9 | 19-197 | 211-297 | 298-305 |
| Fusion comprising SBS-6576 | 3-9 | 18-198 | 212-298 | 299-306 |

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) Cell 48:261-270; Pina et al. (1990) Cell 60:719-731; and Cirillo et al. (1998) EMBO J. 17:244-254.

For such applications, the fusion molecule is typically formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

An exemplary functional domain for fusing with a DNA-binding domain such as, for example, a ZFP, to be used for repressing expression of a gene is a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Another suitable repression domain is methyl binding domain protein 2B (MBD-2B) (see, also Hendrich et al. (1999) Mamm Genome 10:906-912 for description of MBD proteins). Another useful repression domain is that associated with the v-ErbA protein. See, for example, Damm, et al. (1989) Nature 339:593-597; Evans (1989) Int. J. Cancer Suppl. 4:26-28; Pain et al. (1990)

New Biol. 2:284-294; Sap et al. (1989) Nature 340:242-244; Zenke et al. (1988) Cell 52:107-119; and Zenke et al. (1990) Cell 61:1035-1049.

Suitable domains for achieving activation include the HSV VP16 activation domain (see, e.g., Hagrnann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)). Additional exemplary activation domains include, but are not limited to, VP16, VP64, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5,-6,-7, and -8, CPRF 1, CPRF4, MYC-RP/GP, and TRAB 1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

Additional exemplary repression domains include, but are not limited to, KRAB (also referred to as "KOX"), SID, MBD2, MBD3, members of the DNMT family (e.g., DNMT1, DNMT3A, DNMT3B), Rb, and MeCP2. See, for example, Bird et al. (1999) Cell 99:451-454; Tyler et al. (1999) Cell 99:443-446; Knoepfler et al. (1999) Cell 99:447-450; and Robertson et al. (2000) Nature Genet. 25:338-342. Additional exemplary repression domains include, but are not limited to, ROM2 and AtHD2A. See, for example, Chem et al. (1996) Plant Cell 8:305-321; and Wu et al. (2000) Plant J. 22:19-27.

Additional exemplary functional domains are disclosed, for example, in co-owned U.S. Pat. No. 6,534,261 and US Patent Application Publication No. 2002/0160940.

D. Expression Vectors

The nucleic acid encoding the ZFP of choice is typically cloned into intermediate vectors for transformation into prokaryotic or eukaryotic cells for replication and/or expression, e.g., for determination of Kd. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994). Bacterial expression systems for expressing the ZFP are available in, e.g., E. coli, Bacillus sp., and Salmonella (Palva et al., Gene 22:229-235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and exogenous spliced intronic signals.

The particular expression vector used to transport the genetic information into the cell is selected with regard to the intended use of the ZFP. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

VIII. Assays

Once a ZFP has been designed and prepared according to the procedures just set forth, an initial assessment of the activity of the designed ZFP is undertaken. ZFP proteins showing the ability to modulate the expression of a gene of interest can then be further assayed for more specific activities depending upon the particular application for which the ZFPs have been designed. Thus, for example, the ZFPs provided herein can be initially assayed for their ability to modulate PLN expression. More specific assays of the ability of the ZFP to modulate expression of the target PLN gene to treat heart disease(s) are then typically undertaken. A description of these more specific assays are set forth infra in section IX.

The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, Ca2+); cytokine and hormone production levels; and neovascularization, using, e.g., immunoassays (e.g., ELISA and immunohistochemical assays with antibodies), hybridization assays (e.g., RNase protection, Northerns, in situ hybridization, oligonucleotide array studies), colorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to untreated control samples, to examine the extent of modulation. As described above, for regulation of endogenous gene expression, the ZFP typically has a Kd of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as intracellular calcium compartmentalization, cell contractility, transcriptional changes to both known and uncharacterized genetic markers (e.g., Northern blots or oligonucleotide array studies), changes in cell metabolism such as cell growth or pH changes, and changes in intracellular second messengers such as camp or cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with a vector lacking ZFP-encoding sequences or a vector encoding an unrelated ZFP that is targeted to another gene.

In another embodiment, ZFP regulation of endogenous gene expression is determined in vitro by measuring the level of gene mRNA expression (e.g., expression level of target PLN gene). The level of gene expression is measured using amplification, e.g., using PCR, LCR, or hybridization assays, e.g., Northern hybridization, dot blotting and RNase protection. The use of quantitative RT-PCR techniques (i.e., the so-called TaqMan® assays) can also be utilized to quantitate the level of transcript. The level of protein or mRNA is detected using directly or indirectly labeled detection agents, e.g., fluorescently or radioactively labeled nucleic acids, radioactively or enzymatically labeled antibodies, and the like, as described herein. Such methods are also described in U.S. Pat No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety.

Alternatively, a reporter gene system can be devised using a gene promoter from the selected target gene (e.g., PLN) operably linked to a reporter gene such as luciferase, green fluorescent protein, CAT, GAPDH, β-gal, etc. The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining genes involved in contractility. In this assay, the ZFP of choice is administered (e.g., intramuscular or intracardiac injection) into an animal exhibiting aberrant heart function (e.g., aberrant contractility). After a suitable length of time, preferably 4-8 weeks, heart function and/or gene expression are compared to control animals that also have aberrant contractility but did not receive a ZFP. Contractility that is significantly different as between control and test animals (using, e.g., Student's T test) are said to have been affected by the ZFP.

IX. Pharmaceutical Compositions

The ZFPs provided herein, and more typically the nucleic acids encoding them, can optionally be formulated with a pharmaceutically acceptable carrier as a pharmaceutical composition.

A. Nucleic Acid Based Compositions

Conventional viral and non-viral based gene transfer methods can be used to introduce nucleic acids encoding the present ZFPs in mammalian cells or target tissues. Such methods can be used to administer nucleic acids encoding ZFPs to cells in vitro. In some instances, the nucleic acids encoding ZFPs are administered for in vivo or ex vivo gene therapy uses. Non-viral vector delivery systems include DNA plasmids, naked nucleic acid, and nucleic acid complexed with a delivery vehicle such as poloxamers or liposomes. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11: 167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids encoding the ZFPs provided herein include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., TRANSFECTAM™ and LIPOFECTIN™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs can include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long-term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system can therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). See, e.g., Examples 1.

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) is another alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome that are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

As stated above, various viral delivery vehicles, as are known in the art, can be used to introduce a nucleic acid (e.g., a nucleic acid encoding a zinc finger protein) into a cell. The choice of delivery vehicle depends upon a number of factors, including but not limited to the size of the nucleic acid to be delivered and the desired target cell.

In certain embodiments, adenoviruses are used as delivery vehicles. Exemplary adenovirus vehicles include Adenovirus Types 2, 5, 12 and 35. For example, vehicles useful for introduction of transgenes into hematopoietic stem cells, e.g., CD34+ cells, include adenovirus Type 35. Additional adenoviral vehicles include the so-called "gutless" adenoviruses. See, for example, Kochanek et al. (1996) Proc. Natl. Acad. Sci. USA 93:5,731-5,736.

Adeno-associated virus vehicles include AAV serotypes 1, 2, 5, 6, 7, 8 and 9; as well as chimeric AAV serotypes, e.g., AAV 2/1 and AAV 2/5 Both single- and double-stranded AAV vectors can be used.

Lentivirus delivery vehicles have been described, for example, in U.S. Pat. Nos. 6,312,682 and 6,669,936 and in U.S. Patent Application Publication No. 2002/0173030 and can be used, e.g., to introduce transgenes into immune cells (e.g., T-cells). Lentiviruses are capable of integrating a DNA copy of their RNA genome into the genome of a host cell. See, for example, Ory et al. (1996) Proc. Natl. Acad. Sci. USA 93:11382-11388; Miyoshi et al. (1998) J. Virology 72:8150-8157; Dull et al. (1998) J. Virol. 72:8463-8471; Zuffery et al. (1998) J. Virol. 72:9873-9880; Follenzi et al. (2000) Nature Genetics 25:217-222 and Delenda (2004) J. Gene Medicine 6:S125-S138. In certain lentiviral vehicles, this integration function has been disabled to generate non-integrating lentivirus vehicles. See, for example, Poon et al. (2003) J. Virology 77:3962-3972 and Vargas et al. (2004) Human Gene Therapy 15:361-372. The use of both integrating and non-integrating lentivirus vectors for transduction of hematopoietic stem cells has been described by Haas et al. (2000) Mol. Therapy 2:71-80. Transduction of CD4+ T-cells with integrating lentivirus vectors has been described by Humeau et al. (2004) Mol. Therapy 9:902-913.

Herpes simplex virus vehicles, which are capable of long-term expression in neurons and ganglia, have been described. See, for example, Krisky et al. (1998) Gene Therapy 5(11): 1517-1530; Krisky et al. (1998) Gene Therapy 5(12):1593-1603; Burton et al. (2001) Stem Cells 19:358-377; Lilley et al. (2001) J. Virology 75(9):4343-4356

Methods for improving the efficiency of retroviral transduction of hematopoietic stem cells are disclosed, for example, in U.S. Pat. No. 5,928,638.

The tropism of retroviral and lentiviral delivery vehicles can be altered by the process of pseudotyping, thereby enabling viral delivery of a nucleic acid to a particular cell type. See, for example, U.S. Pat. No. 5,817,491.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some instances, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+cells in vitro into clinically important immune cell types using cytokines such a GM-CSF, IFN-Y and TNF-α are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., J. Exp. Med. 176:1693-1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below (see, e.g., Remington's Pharmaceutical Sciences, 17th ed., 1989).

B. Protein Compositions

An important factor in the administration of polypeptide compounds, such as the present ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270:14255-14258 (1995)).

Examples of peptide sequences which can be linked to a ZFP, for facilitating uptake of ZFP into cells, include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) Molecular Therapy 7(5): S461, Abstract #1191.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including Clostridium perfringens iota toxin, diphtheria toxin (DT), Pseudomonas exotoxin A (PE), pertussis toxin (PT), Bacillus anthracis toxin, and pertussis adenylate cyclase (CYA), have been used in attempts to deliver peptides to the cell cytosol as internal or amino-terminal fusions (Arora et al., J. Biol. Chem., 268:3334-3341 (1993); Perelle et al., Infect. Immun., 61:5147-5156 (1993); Stemnark et al., J. Cell Biol. 113:1025-1032 (1991); Donnelly et al., PNAS 90:3530-3534 (1993); Carbonetti et al., Abstr. Annu. Meet. Am. Soc. Microbiol. 95:295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP. The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., PNAS 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217, 344, 4,235,871, 4,261,975, 4,485,054, 4,501,728, 4,774,085, 4,837,028, 4,235,871, 4,261,975, 4,485,054, 4,501,728, 4,774,085, 4,837,028,4,946,787, PCT Publication No. WO 91.backslash.17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858: 161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In some instances, liposomes are targeted using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265: 16337-16342 (1990) and Leonetti et al., PNAS 87:2448-2451 (1990).

C. Dosage

For therapeutic applications of ZFPs, the dose administered to a patient should be sufficient to affect a beneficial therapeutic response in the patient over time. The dose will be determined by the efficacy and Kd of the particular ZFP employed, the nuclear volume of the target cell, and the condition of the patient, as well as the body weight or surface area of the patient to be treated. The size of the dose also will be determined by the existence, nature, and extent of any adverse side effects that accompany the administration of a particular compound or vector in a particular patient.

In determining the effective amount of the ZFP to be administered in the treatment or prophylaxis of heart disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

D. Compositions and Modes of Administration

1. General

ZFPs and the nucleic acids encoding the ZFPs can be administered directly to a subject (e.g., patient) for modulation of gene expression and for therapeutic or prophylactic applications. In general, and in view of the discussion herein, phrases referring to introducing a ZFP into an animal or patient can mean that a ZFP or ZFP fusion protein is introduced and/or that a nucleic acid encoding a ZFP or ZFP fusion protein is introduced in a form that can be expressed in the animal. For example, as described in greater detail in the following section, the ZFPs and/or nucleic acids can be used in the treatment of one or more heart conditions.

Administration of therapeutically effective amounts is by any of the routes normally used for introducing ZFP into ultimate contact with the tissue to be treated. The ZFPs are administered in any suitable manner, preferably with pharmaceutically acceptable carriers (e.g., poloxamer and/or buffer). Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions (see, e.g., Remington's Pharmaceutical Sciences, 17th ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the disclosed methods, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

2. Exemplary Delivery Options

A variety of delivery options are available for the delivery of the pharmaceutical compositions provided herein so as to modulate PLN expression. Depending upon the particular indication (e.g., heart failure), the compositions can be targeted to specific areas or tissues of a subject. For example, in some methods, one delivers compositions to specific regions of the heart to treat congestive heart failure. Other treatments, in contrast, involve administering the composition in a general manner without seeking to target delivery to specific regions.

A number of approaches can be utilized to localize the delivery of agents to particular regions. Certain of these methods involve delivery to the body lumen or to a tissue (see, e.g., U.S. Pat. Nos. 5,941,868; 6,067,988; 6,050,986; and 5,997, 509; as well as PCT Publications WO 00/25850; WO 00/04928; 99/59666; and 99/38559). Delivery can also be effectuated by intramyocardial injection or administration. Examples of such approaches include those discussed in U.S. Pat. Nos. 6,086,582; 6,045,565; 6,056,969; and 5,997,525; and in PCT Publications WO 00/16848; WO 00/18462; WO 00/24452; WO 99/49773 and WO 99/49926. Other options for local delivery include intrapericardial injection (see, e.g., U.S. Pat. Nos. 5,931,810; 5,968,010; and 5,972,013) and perivascular delivery. Various transmyocardial revascular (TMR) channel delivery approaches can be utilized as well. Many of these methods utilize a laser to conduct the revascularization. A discussion of such approaches is set forth in U.S. Pat. Nos. 5,925,012; 5,976,164; 5,993,443; and 5,999,678, for example. Other options include intraarterial and/or intracoronary delivery, for example coronary artery injection (see, e.g., WO 99/29251) and endovascular administration (see, e.g., U.S. Pat. Nos. 6,001,350; 6,066,123; and 6,048,332; and PCT Publications WO 99/31982; WO 99/33500; and WO 00/15285). Thus, for example, one can inject a composition as described herein directly into the myocardium.

Additional options for the delivery of compositions to modulate PLN gene expression include systemic administration using intravenous or subcutaneous administration, cardiac chamber access (see, e.g., U.S. Pat. No. 5,924,424) and tissue engineering (U.S. Pat. No. 5,944,754).

Other delivery methods known by those skilled in the art include the methods disclosed in U.S. Pat. Nos. 5,698,531; 5,893,839; 5,797,870; 5,693,622; 5,674,722; 5,328,470; and 5,707,969.

X. Applications

A. General

ZFPs engineered to bind a chosen target site in a gene of interest, and nucleic acids encoding them, can be utilized to modulate PLN expression in any subject and by so doing, treat contractility-related disorders such as congestive heart failure. Generally, a target site of a nucleic acid within a cell or population of cells is contacted with a ZFP that has binding specificity for that target site. Methods can be performed in vitro with cell cultures or in vivo. Certain methods are performed such that congestive heart failure is treated by repressing PLN gene expression.

B. Transgenic/Knockout Animals

Using the compositions and methods described herein, transgenic animals can be generated using standard techniques. In addition, PLN knockouts or knockdowns can also be generated. For example, a PLN-targeted ZFP as described herein that represses PLN expression is administered to any animal in order to create a knockout or knockdown animal. These animals are useful as models for disease and for drug testing. Currently, only PLN knockout mice are available. Thus, ZFP repressors as described herein make it possible to reduce or eliminate PLN activity in any animal model, for which no feasible ways currently exist to generate knockouts.

Furthermore, as many accepted animal models for studying heart disease and evaluating candidate drugs are non-mouse models, the ability to create PLN knockouts/knockdowns in any animal using the PLN-targeted ZFPs described herein represents an important advance in the field.

C. Therapeutic Applications

The ZFPs provided herein and the nucleic acids encoding them such as in the pharmaceutical compositions described herein can be utilized to modulate (e.g., activate or repress) expression of PLN, thereby modulating cardiac contractility. Modulation of cardiac contractility can result in the amelioration or elimination of various heart conditions. For example, PLN can be repressed using PLN-targeted ZFPs both in cell cultures (i.e., in in vitro applications) and in vivo to improve cardiac contractility. Because ZFP repressors for PLN do not significantly change the expression levels of any other genes (see, Examples), they are likely to be more specific than antisense methods. Unlike the antisense approach, which needs to target a large number of copies of PLN mRNA, there are only two binding sites in each cell to be targeted by a ZFP (i.e., the two copies of the target gene), therefore, a ZFP can function at a relatively low expression level.

Hence, certain methods for treating heart disease involve introducing a PLN-targeted ZFP into an animal. Binding of the ZFP bearing a repression domain to PLN results in increased cardiac contractility and amelioration (or elimination) of congestive heart failure. A repression domain fused to the ZFP represses the expression of PLN.

A variety of assays for assessing PLN expression as it relates to cardiac contractility are known. For example, echocardiograms and other real-time imaging techniques can be used in vivo. See, e.g., Santana et al. (1997) *Heart Vessels Suppl* 12:44-9. The ability of the PLN-targeted ZFPs and/or nucleic acids encoding these ZFPs to modulate cardiac contractility can be evaluated, for example, in calcium transient assays as described in the Examples as well as Fujii et al. (1990) FEBS Lett. 273(1-2):232-4; Nakayama et al. (2002) *FASEB J* 17(1):61-3; Zhao et al. (2003) Cardiovasc Res. 57(1):71-81. Another option is to measure ATP-dependent oxalate-facilitated Ca(2+) uptake of myocyte homogenates, as discussed in Chossat et al. (2001) Cardiovasc Res. 49(2): 288-97. Additional exemplary assays for contractility include hemodynamic assessment of ventricular performance as maximal dP/dt at baseline or in response to increasing dose of β-agonist dobutamine; measurement of fractional shortening (FS) by echocardiography; and measurement of calcium transients in cardiomyocytes using calcium-sensitive dyes such as fluo-3-AM. See, for example, Minamisawa et al. (1999) *Cell* 99(3):313-322 and Braz et al. (2004) *Nature Med.* 10(3): 248-254. Other assays are disclosed in U.S. Pat. No. 6,569, 862. In addition, microscopic examination of tissue sections can be performed, as well as video imaging of isolated cells subjected to electrical stimulation to measure contractile properties. These and other methods are accepted assays and the results can also be extrapolated to other systems.

The following examples are provided solely to illustrate in greater detail particular aspects of the disclosed methods and compositions and should not be construed to be limiting in any way.

EXAMPLE 1

Materials and Methods

A. Cell Culture and Transfection

Rat H9C2(2-1) cells were cultured in DMEM with 10% FBS. Cells were seeded into 6-well plates at the density of ~1.5×10$^5$ cells/well 16 to 24 hours prior to transfection. Duplicate transfections were performed for each construct using FuGENE 6 transfection reagents (Roche, Indianapolis, Ind.). 1-1.2 µg of the ZFP-TF expression plasmid or control plasmid were transfected into each well using 6 µl of Fugene 6 reagent. Transfection reagent-containing media was removed after 8 hours and fresh media was added. Cells were harvested 48 to 72 hours post-transfection for RNA isolation.

Human SJRH30 cells were cultured in RPMI1640 medium supplemented with 10% FBS. Cells were seeded in 6-well plates at the density of ~2×10$^5$ cells/well 16 to 24 hours prior to transfection. Duplicate transfections were performed for each construct using FuGENE 6 transfection reagents (Roche, Indianapolis, Ind.). For each well, 1.2 μg ZFP repressor plasmids were mixed with 6 μl of FuGENE 6 transfection reagents for 30 minutes. The complex was then added into the culture with serum-free medium. Transfection reagent-containing media was removed after 8 hours and fresh media was added. Cells were harvested 48 to 72 hours post-transfection.

Human UtSMC cells were cultured with the SmGM-2 Bulletkit medium (Cambrex, Rockland, Me.). Nucleofection was carried out according the manufacture's protocol (Amaxa Biosystems, Cologne, Germany). In brief, 5×10$^5$ cells and 5 μg plasmid DNA were mixed with 100 μl Nucleofector Solution V. After electroporation with the Nucleofector program T-30, the cells were plated into 6-well plates. Cells were harvested 48 to 72 hours post-transfection.

Primary cardiomyocytes were isolated from 1-day old rat neonates (Strain: Sprague Dawley), and infected with Adenoviruses expressing either ZFP 6439-kox or kox domain alone.

B. Drug Selection to Enrich for Transgene-Positive Cells

To enrich the transfected cell population, a drug selection protocol was performed to kill untransfected cells. 1.2 μg of the ZFP-TF expression plasmid or control plasmid were co-transfected with 0.3 μg of puromycin resistance vector. At 24 hours post-transfection, puromycin was added to the media (at a fmal concentration of 1.5 μg/ml for H9C2(2-1) cells, and 1.0 μg/ml for SJRH30 cells). After 60 hours of puromycin selection, most untransfected cells were killed. The resistant cells were harvested for subsequent RNA analysis.

C. Taqman Analysis

RNA was isolated using either the High Pure RNA Isolation Kit (Roche) or the RNeasy Kit (Qiagen, Valencia, Calif.). Taqman assays were performed as previously described (J. Biol. Chem. 275:33850). In brief, TaqMan was performed in 96-well plate format on ABI 7700 SDS machine (Perkin Elmer, Boston, Mass.) and analyzed with SDS version 1.6.3 software. RNA samples (25 ng) were mixed with 0.1 μM of probe and optimal amount of each primer, 5.5 mM MgCl$_2$ and 0.3 mM (each) dNTP, 0.625 unit of AmpliTaq Gold DNA Polymerase, 6.25 units of MultiScribe Reverse Transcriptase, and 5 units of RNase Inhibitor in 1× TaqMan buffer A from PE. The reverse transcription reactions were performed at 48° C. for 30 minutes. After denaturing at 95° C. for 10 minutes, PCR amplification reactions were conducted for 40 cycles at 95° C. for 15 seconds and at 60° C. for 1 minute. The levels of PLN and GAPDH mRNA were quantified using standard curves spanning a 125-fold concentration range (relative levels of 0.2 to 25; five-fold dilution series). Each RNA sample was assayed in duplicate Taqman reactions. The ratio of PLN/GAPDH was used to determine the relative levels of PLN in various samples. Sequences and concentrations of primers and probes are provided in Table A.

TABLE A

TAQMAN REAGENTS

| Gene Target | Oligonucleotide name | Sequence (5' -->3') | μM/rxn | Seq Id |
|---|---|---|---|---|
| rat PLN | rPLN-57F | AGTCTGCATTGTGACGATCACAG | 0.3 | 50 |
| | rPLN-125R | GCAGGCAGCCAAACGC | 0.9 | 51 |
| | rPLN-81T** | AGCCAAGGCCTCCTAAAAGGAGACAGCT | 0.1 | 52 |

TABLE A-continued

TAQMAN REAGENTS

| Gene Target | Oligonucleotide name | Sequence (5' -->3') | μM/rxn | Seq Id |
|---|---|---|---|---|
| rat GAPDH | mGAPDH-F1 | CCCATGTTTGTGATGGGTGTG | 0.1 | 53 |
| | mGAPDH-R1 | CATGGACTGTGGTCATGA | 0.3 | 54 |
| | mGAPDH-P1** | ATCCTGCACCACCAACTGCTTAGC | 0.1 | 55 |
| human PLN | hPLN-F56 | TCTATACTGTGATGATCACAGCT | 0.3 | 56 |
| | hPLN-R173 | CAGGACAGGAAGTCTGAAGT | 0.3 | 57 |
| | hPLN-PF119L** | CTGCCAGCTTTTTATCTTTCTCTCGACC | 0.1 | 58 |
| human GAPDH | hGAPDH-Fo1 | CCATGTTCGTCATGGGTGTGA | 0.1 | 59 |
| | hGAPDH-Re1 | CATGGACTGTGGTCATGAGT | 0.1 | 60 |
| | hGAPDH-Pr1** | TCCTGCACCACCAACTGCTTAGCA | 0.1 | 61 |
| kox | koxFor2 | GGTTGGAGAAGGGAGAAGAG | 0.1 | 62 |
| | FLAG-Rev | TACTTGTCATCGTCGTCCTTGT | 0.1 | 63 |
| | Kox-Pro2** | CACCAAGAGACCCATCCTGATTCAG | 0.1 | 64 |
| rat 18S | 18S-For1 | TTCCGATAACGAACGAGACTCT | 0.1 | 65 |
| | 18S-Rev1 | TGGCTGAACGCCACTTGTC | 0.1 | 66 |
| | 18S-Pro1** | TAACTAGTTACGCGACCCCCGAG | 0.1 | 67 |

Note:
Asterisks (**) denote probes. Probe ends are labeled with: 5' -- 6FAM; and 3' -- BHQ1 ("Black Hole Quencher 1" ® -- Biosearch).

D. RNA Rat Primary Cardiomyocytes: Isolation and Infection

Fifty 1-day-old Sprague Dawley rats were sacrificed and their hearts dissected out for enzymatic digestion (115 unit/ml Collagenase (Worthington) and 0.8 mg/ml Pancreatin (Sigma) in Ads buffer). The digestion was performed with 15 ml of enzyme solution, in a spinner flask with 37° C. circulating water bath. After 30 minutes of digestion, heart pieces were allowed to settle briefly and the enzyme solution (containing mostly red blood cells and cell debris) were removed and discarded. Fresh enzyme solution was added to heart pieces. Every 20 minutes, dissociated cells were collected, and fresh enzyme solution was added to the remaining heart pieces. This process was repeated 4 times, and collected cells were pooled. Cells were then layered onto the top of a Percoll gradient. Each Percoll gradient consisted of 4 ml top Percoll (density of 1.059 mg/ml) and 3 ml bottom Percoll (density of 1.082 mg/ml); cells from ~10 hearts were loaded onto each gradient. After 30 minutes of centrifugation at 3,000 rpm, cardiomyocytes at the interface between the top and bottom Percoll were collected, washed and plated onto culture dishes that were pretreated with 1% Gelatin (Sigma). The plating media was a mixture of DMEM (68%, Invitrogen), M199 (17%, Invitrogene), fetal calf serum (5%, Hyclone) and horse serum (10%, Hyclone). Two days after plating, plating media was replaced with growth media, which consisted of 80% DMEM and 20% M199.

For adenovirus infection, neonatal rat cardiomyocytes were plated at 60,000 cells/well in a 24-well cell culture plate. Two days later, roughly half of the plated cells were estimated to have attached onto the plate. These cells were infected with recombinant adenoviruses at a multiplicity of infection (MOI) of 100, 200 and 400 for 24 h at 37. At 48 h post-infection, cells were collected for RNA analyses.

E. Adenovirus Production and Infection

Recombinant adenoviral vectors, Ad-Kox1 and Ad-6439Kox1, were created as follows: the Mlu I-Afl II fragment of the plasmid pcDNA4/TO (Invitrogen) which consists of the human cytomegalovirus immediate early promoter/enhancer (CMV) and two tetracycline operator sequences (TetO$_2$), and the Afl II-Xho I fragment of the plasmid pcDNA3-Kox1 or pcDNA3-6439Kox1 which contains the ZFP expression cassette, were simultaneously cloned into the Mlu I and Xba I restriction sites upstream of a bovine growth hormone polyadenylation signal (BGH polyA) in the plasmid pShuttle (Clontech). The CMV-TetO$_2$-ZFP-BGH polyA cassette was then excised via the unique I-Ceu I and PI-Sce I restriction sites in the pShuttle and ligated to the Adeno-X viral DNA previously digested with I-Ceu I and PI-Sce I (Clontech). All cloned sequences were verified by DNA sequencing.

Recombinant adenoviral vectors were packaged by transfecting T-REX™-293 cells (Invitrogen), and adenoviruses were harvested from transfected T-REX™-293 cells lysed with three consecutive freeze-thaw cycles. Recombinant adenoviruses were further amplified in T- REX™-293 cells and purified by double cesium chloride gradient centrifugation (Qiagene). Purified recombinant adenoviruses were dialyzed against three changes of 10 mM Tris pH8.0-2 mM MgCl2-4% sucrose, and stored in aliquots at −80° C. Adenoviral particle numbers were determined by absorbance at 260 nm and infectious titers were determined using the Adeno-X Rapid Titer Kit (Clontech).

EXAMPLE 2

Repression of Phospholamban Expression in Cell Lines Using Designed Zinc Finger Proteins Fusion proteins comprising 6-fingered zinc finger proteins designed to recognize a target site in PLN and a repression domain were designed as described above in and U.S. Pat. No. 6,607,882. The designed ZFPs and the target sites recognized by these ZFPs are shown in Tables 2-4.

A. Fusion Proteins Comprising Rat PLN-Targeted ZFPs

In order to test the ability of ZFPs designed as above and shown in Tables 2-4, the following experiments were conducted. Sequences encoding a fusion protein comprising a PLN-targeted ZFP (SBS-6439, SBS-6435 or SBS-6437) and a repression domain (KOX) were introduced into a pcDNA3.1 plasmid backbone (Invitrogen, Carlsbad, Calif.) to create PLN-targeted ZFP expression plasmids. Empty pcDNA3.1 plasmid vectors were also prepared for use as controls. PLN-targeted ZFP AAV-vectors were also prepared as described in Example 1. The fusion proteins were designated 6439-KOX, 6437-KOX and 6435-KOX.

Plasmids or AAV-based vectors including one of 6439-KOX, 6437-KOX or 6435-KOX were transfected into cultured Rat H9c2(2-1) cells as described in Example 1. Empty vectors were used as controls. For drug selection assays, a puromycin-resistant plasmid was co-transfected with either PLN-ZFP-containing plasmid or the control vector to enrich the transfected population. Cells were selected with 1 μg/ml puromycin to kill untransfected cells. ZFP expression was measured by Taqman assay as described in Example 1.

Figure 2B:
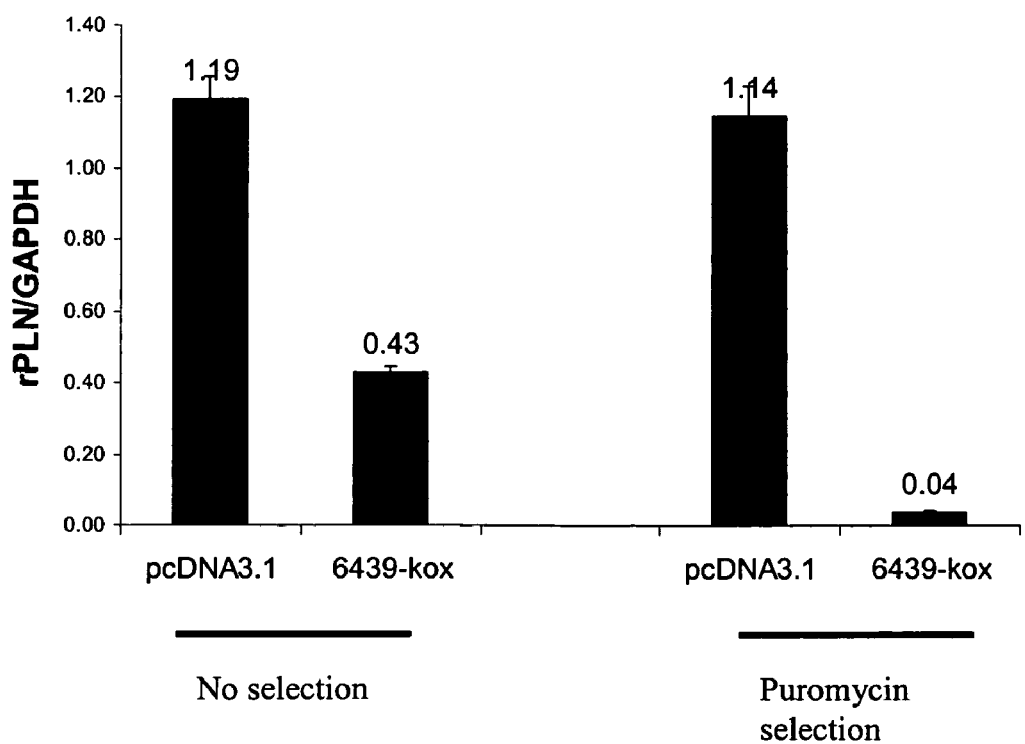
FIG. 2B shows repression of PLN by plasmids encoding 6439-KOX in unselected cells and cells subject to puromycin selection.
Figure 2C:
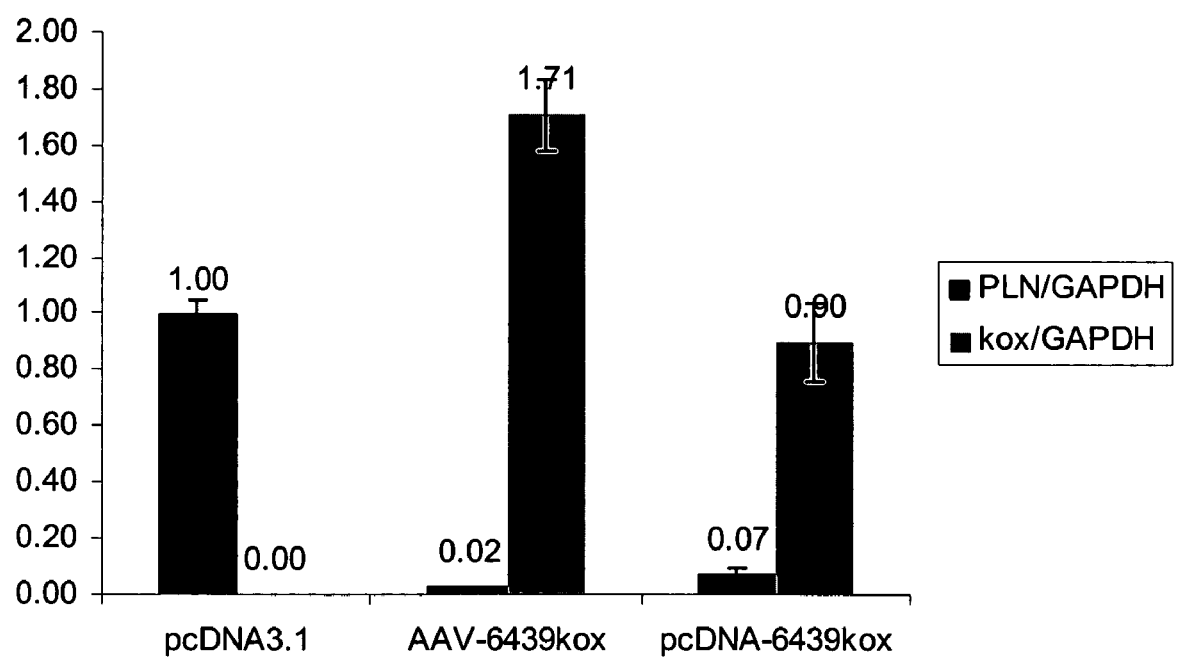
FIG. 2C depicts repression of rat PLN when 6439-KOX is administered using plasmid or AAV vectors.

FIG. 2A shows the results of repression of rat PLN expression using 6439-KOX, 6437-KOX or 6435-KOX in plasmid vectors. FIG. 2B shows PLN repression in unselected and puromycin selected cells transfected with 6439-KOX in a plasmid vector. In unselected cells, 6439-KOX represses PLN expression by approximately 75% as compared to empty vector transfected cells. In puromycin-selected cells, 6439-KOX represses rat PLN expression by approximately 97% as compared to empty vector transfected cells. FIG. 2C shows PLN repression by 6439-KOX when administered using either plasmid (pcDNA) or AAV vectors. AAV delivery of 6439-KOX repressed rat PLN expression by approximately 98%. (FIG. 2C). Furthermore, the enhanced PLN repression is correlated with a higher level of ZFP expression from the AAV-MCS vector (Stratagene, La Jolla, Calif.) compared to the pcDNA3.1 vector (Invitrogen, Carlsbad, Calif.).

B. Fusion Proteins Comprising Humans PLN-Targeted ZFPs

Repression of human PLN gene expression was also tested using fusion proteins comprising ZFPs targeted to human PLN (SBS-6576 and SBS-6624) and a KOX repression domain. ZFP-KOX fusions were designated 6576-KOX and 6624-KOX.

SJRH30 cells were cultured and subjected to the puromycin selection as described above in Example 1. Puromycin selection resulted in greater than 85% transfection efficiency, as measured by determining transgene positive cells.

UtSMC cells were cultured as described in Example 1. The cells were subjected to the nucleofection protocol, essentially as described in the manufacturer's instructions (Amaxa, Germany).

As shown in FIG. 3, 6576-KOX and 6624-KOX repressed human PLN by approximately 75% in SJRH30 cells. (FIGS. 3B and 3D). In UtSMC cells, 6576-KOX repressed PLN expression by approximately 75% while 6624-KOX repressed human PLN expression by approximately 60%. (FIG. 3A and FIG. 3C).

Thus, PLN-targeted ZFPs are capable of repressing expression of PLN.

EXAMPLE 3

Repression of Phospholamban Expression in Cardiomyocytes Using Designed Zinc Finger Proteins A. Adult Rat Cardiomyocytes Fusion protein 6439-KOX was also tested for its ability to modulate Ca$^{2+}$ transients in adult rat myocytes. Briefly, plasmids encoding 6439-KOX were co-injected into adult rat myocardium with a green fluorescent GFP-encoding plasmid.

Cardiomyocytes were isolated 3 days after injection, and incubated with Ca$^{2+}$ sensitive dye fluo-3-AM. Changes in fluorescence were monitored by a microfluorimeter. See Minamisawa et al., supra.

Figure 4:
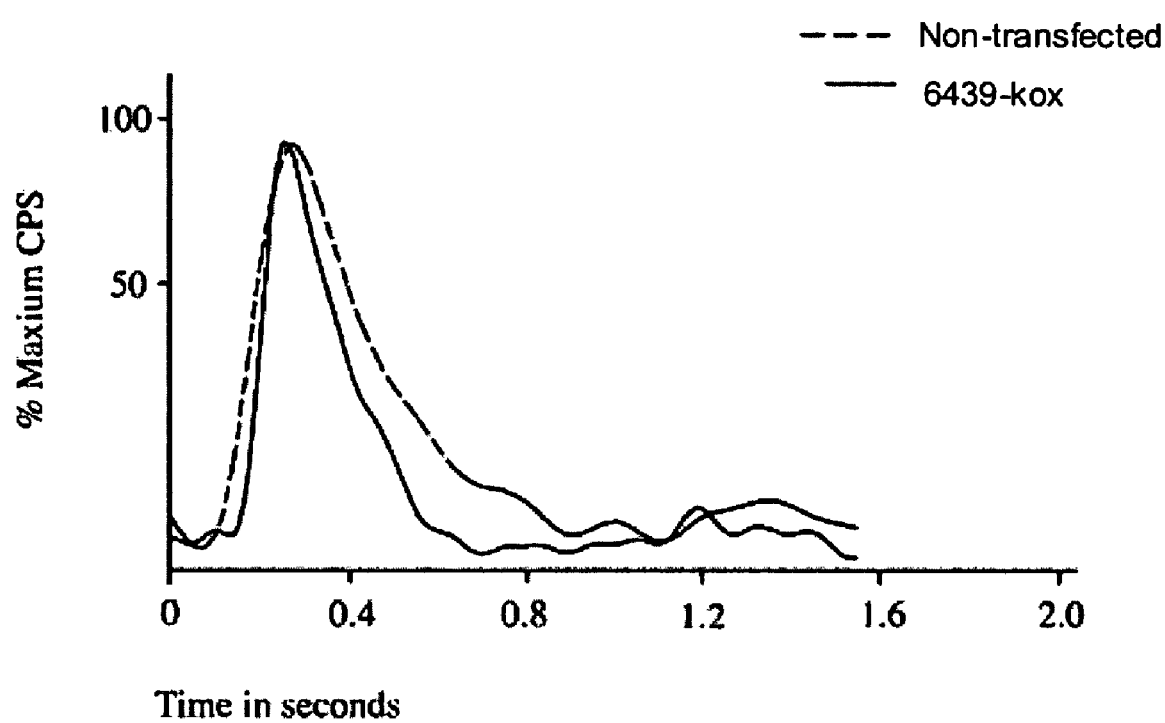
FIG. 4 is a graph depicting the effect of PLN-targeted ZFPs on $Ca^{2+}$ transients in adult rat cardiomyocytes.

As shown in FIG. 4, 6439-KOX increases Ca$^{2+}$ transients in adult rat cardiomyocytes. Compared to untransfected cells, 6439-KOX-containing cells displayed Ca$^{2+}$ transients with a shortened duration and faster decay, indicating that ZFP-mediated repression of PLN is sufficient to change the Ca$^{2+}$. Analysis of video images also showed that isolated cardiomyocytes contraction transfected with a plasmid encoding 6439-KOX-tranfected had accelerated rates of shortening and relaxation as compared to untransfected cells.

B. Primary Cardiomyocytes

Figure 5A:
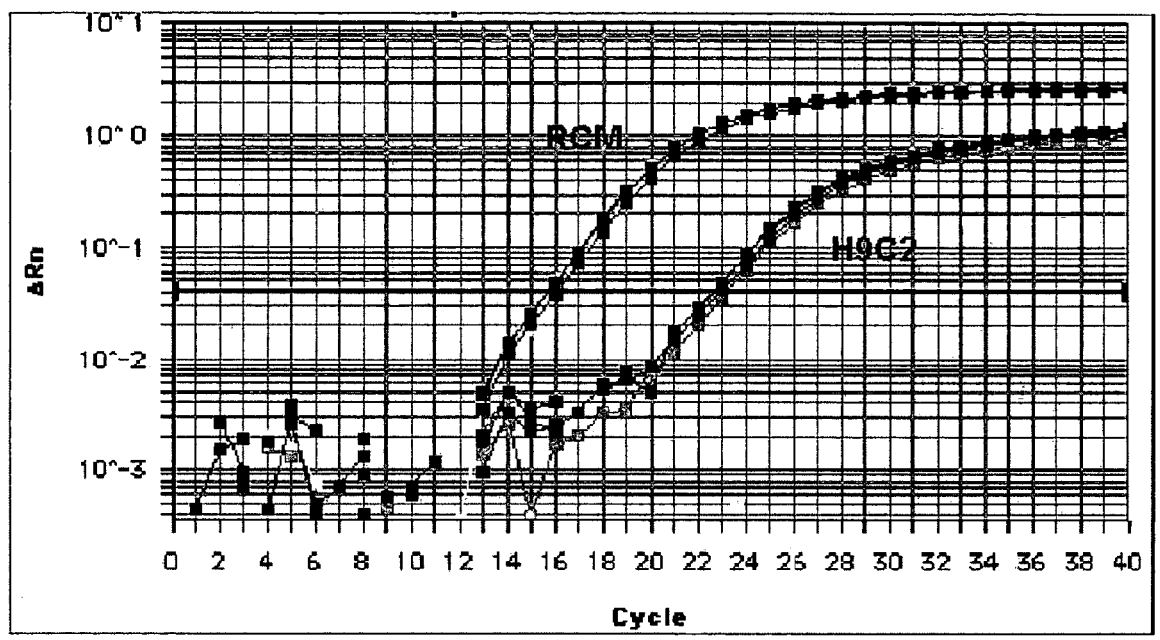
FIG. 5A depicts a Taqman amplification plot of PLN mRNA from rat cardiomyocytes (RCM) and H9C2(2-1) cells. The Ct value for RCM PLN is ~16 and the Ct value for H9C2(2-1) PLN is ~22. Each Ct cycle difference represents a 2-fold difference in RNA level.

To test the activity of 6439-KOX, the following experiments were conducted. Primary cardiomyocytes were isolated from 1-day-old neonatal rats. The expression level of PLN in these cells were ~50 times higher than that of H9C2 (2-1) cells (FIG. 5A).

6439-KOX was administered to the primary cardiomyocytes using plasmid or AAV vectors as described above. We observed that transfection efficiency into cardiomyocytes cells is typically very low (<10%) using plasmid vectors; accordingly, ZFPs were delivered using adenoviruses, which can infect >85% of the cells.

Figure 5B:
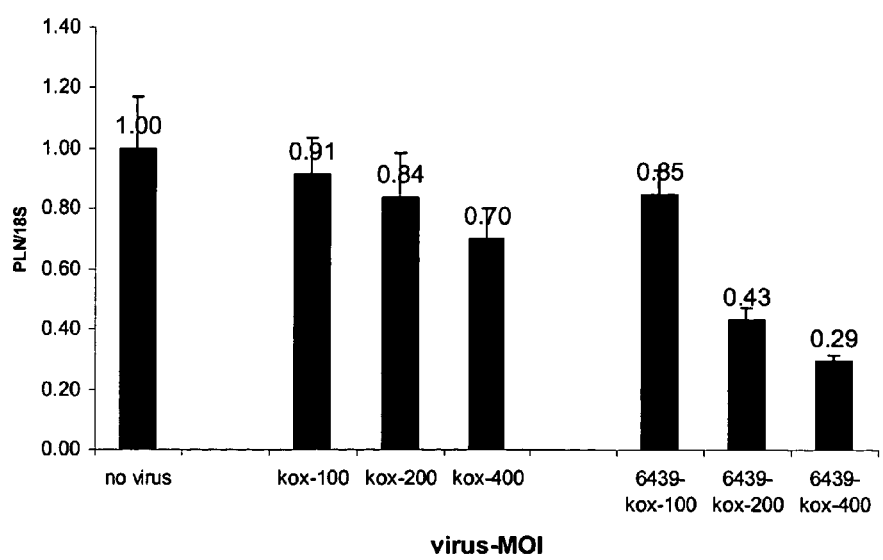
FIG. 5B shows levels of PLN mRNA in adenovirus-infected rat cardiomyocytes. Adenoviruses expressing either 6439-kox or the kox repression domain alone were used to infect cardiomyocytes at indicated the MOI (100, 200 and 400).

6439-KOX repressed PLN expression in a dose-dependent manner in primary rat cardiomyocytes (FIG. 5B), indicating that PLN-targeted ZFPs effectively block the transcription of PLN.

EXAMPLE 4

Specificity

To test the specificity of PLN-targeted ZFPs, the following microarray experiments were conducted.

A. Fusion Proteins Comprising SBS-6573 (Human)

To test the specificity of 6573-KOX, total RNA from UtSMC cells was isolated using RNeasy mini kit (QIAGEN) according to manufacturer's recommendations. RNA samples for hybridization were prepared according to Affymetrix GeneChip Small Sample Labeling protocol using 200 ng of total RNA. Changes in gene expression were analyzed using Affymetrix human U-133A array, which contains 22,283 probes representing roughly 16,000 genes. Affymetrix Microarray Suite 5.0 and Data Mining Tool 3.0 software were used for data analysis. Criteria for differentially expressed genes were: >2-fold change, 100% confidence call, and p-value <0.05.

B. Fusion Proteins Comprising SBS-6439 (Rat)

For 6439-KOX, H9C2(2-1) cells were seeded in p100 plates (~1×106 cells/plate). 7 µg of 6439-kox or pcDNA3 empty vector were transfected into each plate using 30 µl of Lipofectamine 2000 reagent. Transfection reagent-containing media was removed after 8 hours and fresh media was added. Cells were harvested 60 hours after transfection.

Total RNA was isolated using TRIzol reagent (Invitrogen) according to manufacturer's recommendations. RNA samples for hybridization were prepared according to standard Affymetrix protocol using 10 µg of total RNA. Changes in gene expression were analyzed using rat RAE-230A array, which contains 15,923 probes representing roughly 14,000 genes. Data analysis was carried out using Affymetrix Microarray Suite 5.0 and Data Mining Tool 3.0 software.

Criteria for differentially expressed genes were: >2-fold change, 100% confidence call, and p-value <0.05.

C. Results

Approximately 14,000 and 16,000 transcripts were monitored by the rat and human microarrays described above. In both rat and human cells tested, PLN was the only gene whose change in expression level met the following criteria: 1) a 2-fold or more repression as assayed by Affymetrix analysis, 2) a 100% confidence call made by Affymetrix analysis, 3) a p-value <0.05% and 4) a 2-fold or more repression when the RNA level was confirmed using Taqman assays.

Thus, PLN-targeted ZFPs described herein exhibit specificity for PLN genes.

EXAMPLE 5

Use of Adeno-Associated Virus (AAV) Vectors for Delivery of Phospholamban-Regulating Engineered Transcription Factors to Cultured Uterine Smooth Muscle Cells Sequences encoding the three-finger SBS-1563 zinc finger protein (see Tables 1 and 3) fused to a KOX repression domain (1563-KOX) were cloned into a pAAV-MCS vector (Strategene, La Jolla, Calif.). This construct was co-transfected into HEK 293 cells along with pAAV-RC and pHelper plasmids (both from Strategene, La Jolla, Calif.). Three days later, crude lysates were obtained and used as a source of ZFP-encoding virus.

Figure 6:
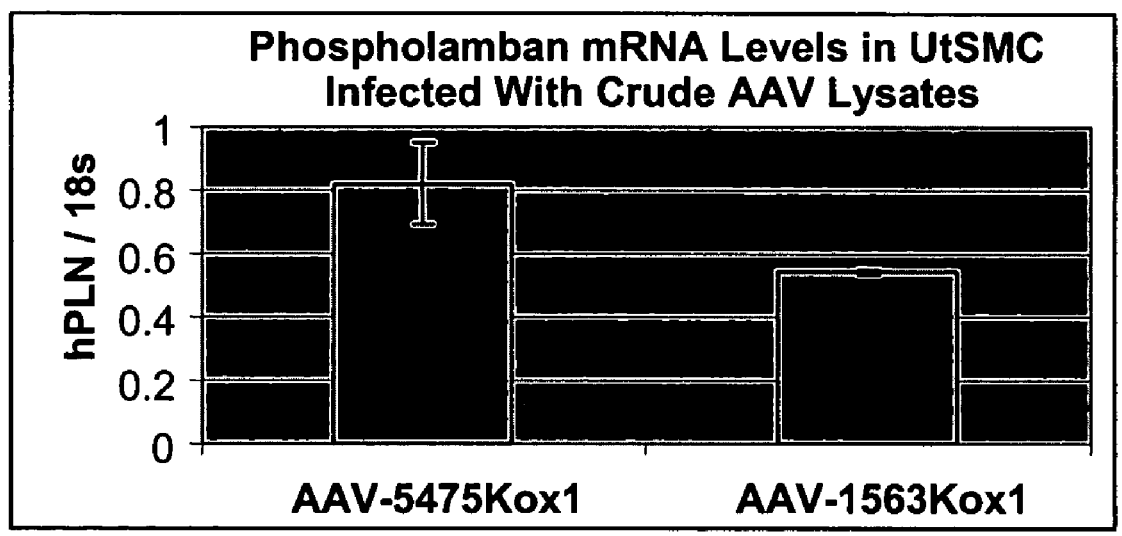
FIG. 6 shows levels of phospholamban mRNA (normalized to 18S rRNA) in UtSMC cells infected with AAV encoding the 1563-KOX phospholamban repressor protein (right bar). As a control (left bar), another culture of UtSMC cells were infected with AAV encoding the 5475-KOX protein, a repressor protein targeted to the CHK2 gene.

UtSMC cells, a human primary uterine smooth muscle cell line, were infected with the crude AAV lysate at a MOI of $2 \times 10^4$ vector genomes per cell. At 72 hours post-infection, cells were collected, their RNA was extracted and the amount of phospholamban mRNA was measured by real-time PCR (Taqman®). The results, shown in FIG. 6, indicate an approximately two-fold reduction in phospholamban mRNA following infection with AAV encoding the 1563-KOX phospholamban repressor.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entireties for all purposes to the same extent as if each individual publication, patent or patent application were specifically and individually indicated to be so incorporated by reference.

What is claimed is:

1. A method for increasing cardiac contractility in a subject, the method comprising:
   introducing a nucleic acid into the subject, wherein the nucleic acid encodes a polypeptide, wherein the polypeptide comprises:
   (i) a zinc finger DNA-binding domain that is engineered to bind to a target site in the phospholamban gene; and
   (ii) a transcriptional repression domain;
   such that the nucleic acid is expressed in one or more cardiac cells of the subject, whereby the polypeptide binds to the target site and represses transcription of the phospholamban gene.

2. The method of claim 1, wherein the zinc finger DNA-binding domain comprises six zinc fingers and the amino acid sequence of the recognition regions of the zinc fingers is as follows:

| F1: | RSDHLSQ | (SEQ ID: 38) |
| F2: | RSDVRKN | (SEQ ID: 39) |
| F3: | RSDALSV | (SEQ ID: 40) |
| F4: | DNANRTK | (SEQ ID: 41) |
| F5: | RSDHLST | (SEQ ID: 42) |
| F6: | TSSNRTK | (SEQ ID: 43). |

3. The method of claim 1, wherein the zinc finger DNA-binding domain comprises six zinc fingers and the amino acid sequence of the recognition regions of the zinc fingers is as follows:

| F1: | RSDNLSE | (SEQ ID: 44) |
| F2: | HSRSRKT | (SEQ ID: 45) |
| F3: | DSESLNA | (SEQ ID: 46) |
| F4: | TSSNLSR | (SEQ ID: 47) |
| F5: | RSDNLSQ | (SEQ ID: 48) |
| F6: | QRQHRKT | (SEQ ID: 49). |

4. A polynucleotide encoding a protein comprising an engineered zinc finger DNA-binding domain, wherein the DNA-binding domain comprises six zinc fingers and the amino acid sequence of the recognition regions of the zinc fingers is as follows:

| F1: | RSDHLSQ | (SEQ ID: 38) |
| F2: | RSDVRKN | (SEQ ID: 39) |
| F3: | RSDALSV | (SEQ ID: 40) |
| F4: | DNANRTK | (SEQ ID: 41) |
| F5: | RSDHLST | (SEQ ID: 42) |
| F6: | TSSNRTK | (SEQ ID: 43). |

5. A polynucleotide encoding a protein comprising an engineered zinc finger DNA-binding domain, wherein the DNA-binding domain comprises six zinc fingers and the amino acid sequence of the recognition regions of the zinc fingers is as follows:

| F1: | RSDNLSE | (SEQ ID: 44) |
| F2: | HSRSRKT | (SEQ ID: 45) |
| F3: | DSESLNA | (SEQ ID: 46) |
| F4: | TSSNLSR | (SEQ ID: 47) |
| F5: | RSDNLSQ | (SEQ ID: 48) |
| F6: | QRQHRKT | (SEQ ID: 49). |

6. The method of claim 1, wherein the transcriptional repression domain is a KOX domain.

* * * * *